US011179331B1

(12) United States Patent
Espinoza et al.

(10) Patent No.: US 11,179,331 B1
(45) Date of Patent: Nov. 23, 2021

(54) ORAL SOLUBLE FILM CONTAINING SILDENAFIL CITRATE

(71) Applicant: CURE Pharmaceutical Holding Corp., Oxnard, CA (US)

(72) Inventors: Maribel Espinoza, Oxnard, CA (US); Vered Gigi, Oxnard, CA (US)

(73) Assignee: CURE PHARMACEUTCAI HOLDING CORP, Oxnard, CA (US)

( * ) Notice: Subject to any disclaimer, the term of this patent is extended or adjusted under 35 U.S.C. 154(b) by 0 days.

(21) Appl. No.: 17/236,054

(22) Filed: Apr. 21, 2021

Related U.S. Application Data

(60) Provisional application No. 63/012,988, filed on Apr. 21, 2020.

(51) Int. Cl.
| | |
|---|---|
| *A61K 47/32* | (2006.01) |
| *A61K 47/14* | (2017.01) |
| *A61K 47/26* | (2006.01) |
| *A61K 47/02* | (2006.01) |
| *A61K 47/10* | (2017.01) |
| *A61K 47/38* | (2006.01) |
| *A61K 47/22* | (2006.01) |
| *A61K 47/46* | (2006.01) |
| *A61K 31/519* | (2006.01) |
| *A61K 9/00* | (2006.01) |

(52) U.S. Cl.
CPC ............ *A61K 9/006* (2013.01); *A61K 31/519* (2013.01); *A61K 47/02* (2013.01); *A61K 47/10* (2013.01); *A61K 47/14* (2013.01); *A61K 47/22* (2013.01); *A61K 47/26* (2013.01); *A61K 47/32* (2013.01); *A61K 47/38* (2013.01); *A61K 47/46* (2013.01)

(58) Field of Classification Search
CPC ........ A61K 9/006; A61K 47/32; A61K 47/14; A61K 47/26; A61K 47/02; A61K 47/10; A61K 47/38; A61K 47/22; A61K 47/46; A61K 31/519
See application file for complete search history.

(56) References Cited

U.S. PATENT DOCUMENTS

| | | |
|---|---|---|
| 6,552,024 B1 | 4/2003 | Chen et al. |
| 7,579,019 B2 | 8/2009 | Tapolsky et al. |
| 7,585,493 B2 | 9/2009 | Hale et al. |
| 7,897,080 B2 | 3/2011 | Yang et al. |
| 8,017,150 B2 | 9/2011 | Yang et al. |
| 8,147,866 B2 | 4/2012 | Finn et al. |
| 8,414,922 B2 | 4/2013 | Bryson et al. |
| 8,475,832 B2 | 7/2013 | Myers et al. |
| 8,580,830 B2 | 11/2013 | Leichs et al. |
| 8,603,514 B2 | 12/2013 | Yang et al. |
| 8,652,378 B1 | 2/2014 | Yang et al. |
| 8,663,687 B2 | 3/2014 | Myers et al. |
| 8,703,177 B2 | 4/2014 | Finn et al. |
| 8,765,167 B2 | 7/2014 | Myers et al. |
| 8,771,736 B2 | 7/2014 | Ryoo et al. |
| 8,846,074 B2 | 9/2014 | Bryson et al. |
| 8,900,497 B2 | 12/2014 | Yan et al. |
| 8,900,498 B2 | 12/2014 | Yan et al. |
| 8,906,277 B2 | 12/2014 | Yang et al. |
| 9,044,475 B2 | 6/2015 | Giovinazzo et al. |
| 9,095,577 B2 | 8/2015 | Myers et al. |
| 9,108,340 B2 | 8/2015 | Yang et al. |
| 9,283,219 B2 | 3/2016 | Bryson et al. |
| 9,326,981 B2 | 5/2016 | Giovinazzo et al. |
| 9,492,379 B2 | 11/2016 | Park et al. |
| 9,522,188 B2 | 12/2016 | Finn et al. |
| 9,655,843 B2 | 5/2017 | Finn et al. |
| 9,669,019 B2 | 6/2017 | Giovinazzo et al. |
| 9,669,021 B2 | 6/2017 | Giovinazzo et al. |
| 9,687,454 B2 | 6/2017 | Myers et al. |
| 9,789,112 B2 | 10/2017 | Kohr et al. |
| 9,855,221 B2 | 1/2018 | Myers et al. |
| 9,901,539 B2 | 2/2018 | Finn et al. |
| 9,907,759 B2 | 3/2018 | Jeon et al. |
| 9,931,305 B2 | 4/2018 | Yang et al. |
| 10,092,651 B2 | 10/2018 | Jeon et al. |
| 2003/0068378 A1 | 4/2003 | Chen et al. |
| 2003/0118653 A1 | 6/2003 | Chen et al. |
| 2006/0110478 A1 | 5/2006 | McCleary et al. |
| 2007/0031340 A1 | 2/2007 | Hale et al. |
| 2008/0014228 A1 | 1/2008 | Darmuzey et al. |
| 2008/0026040 A1 | 1/2008 | Farr et al. |
| 2008/0286343 A1 | 11/2008 | Cengic et al. |
| 2008/0311162 A1 | 12/2008 | Darmuzey et al. |
| 2009/0047330 A1 | 2/2009 | Bangalore |
| 2009/0047350 A1 | 2/2009 | Bangalore |
| 2010/0092545 A1 | 4/2010 | Yang et al. |
| 2010/0105783 A1 | 4/2010 | Lee et al. |
| 2010/0178349 A1* | 7/2010 | Kolter .................. A61K 9/2027 424/489 |
| 2010/0184722 A1 | 7/2010 | Swart et al. |
| 2010/0240724 A1 | 9/2010 | Chang et al. |
| 2011/0237563 A1 | 9/2011 | Costantini |
| 2012/0110957 A1 | 5/2012 | Lee et al. |
| 2012/0156229 A1 | 6/2012 | Park et al. |
| 2013/0039932 A1 | 2/2013 | Park et al. |
| 2013/0059854 A1 | 3/2013 | Ryoo et al. |
| 2013/0216594 A1 | 8/2013 | Krekeler et al. |

(Continued)

FOREIGN PATENT DOCUMENTS

| | | |
|---|---|---|
| EP | 660056 A1 | 6/1995 |
| EP | 1143940 A2 | 7/2000 |

(Continued)

OTHER PUBLICATIONS

PEG-PVA Wikipedia, Nov. 30, 2015.*

*Primary Examiner* — Zohreh A Fay
(74) *Attorney, Agent, or Firm* — Carlson Caspers

(57) ABSTRACT

The present invention relates to an oral soluble film (OSF), methods of orally administering the same, and methods of manufacturing the same. The oral soluble film includes sildenafil citrate, and can further include a binder, filler, flavoring agent, plasticizer, sweetening agent, preservative, solvent, and optionally coloring agent. The active ingredient and excipients can be provided and present in an amount effective to achieve desired physical and performance characteristics of the OSF.

25 Claims, No Drawings

(56) References Cited

U.S. PATENT DOCUMENTS

| | | |
|---|---|---|
| 2013/0217697 A1 | 8/2013 | Kohr et al. |
| 2013/0220526 A1 | 8/2013 | Yang et al. |
| 2013/0323307 A1 | 12/2013 | Jeon et al. |
| 2013/0333831 A1 | 12/2013 | Yang et al. |
| 2013/0337148 A1 | 12/2013 | Yang et al. |
| 2014/0000800 A1 | 1/2014 | Yang et al. |
| 2014/0008830 A1 | 1/2014 | Yang et al. |
| 2014/0008831 A1 | 1/2014 | Yang et al. |
| 2014/0008832 A1 | 1/2014 | Yang et al. |
| 2014/0070440 A1 | 3/2014 | Yang et al. |
| 2014/0179653 A1 | 6/2014 | Leichs et al. |
| 2014/0335153 A1 | 11/2014 | Allen et al. |
| 2014/0371210 A1 | 12/2014 | Battaglia |
| 2014/0377328 A1 | 12/2014 | Ishise et al. |
| 2015/0025084 A1 | 1/2015 | Jeon et al. |
| 2016/0022574 A1 | 1/2016 | Leichs et al. |
| 2016/0095818 A1 | 4/2016 | Hugerth et al. |
| 2016/0206639 A9 | 7/2016 | Yang et al. |
| 2016/0279071 A1 | 9/2016 | Park et al. |
| 2016/0279134 A1 | 9/2016 | Kohr et al. |
| 2017/0100327 A1 | 4/2017 | Allen |
| 2017/0119660 A1 | 5/2017 | Temtsin-Krayz et al. |
| 2017/0143623 A1 | 5/2017 | Cilurzo et al. |
| 2017/0360942 A1 | 12/2017 | Myers et al. |
| 2018/0280518 A1 | 10/2018 | Myers et al. |

FOREIGN PATENT DOCUMENTS

| | | |
|---|---|---|
| EP | 1301186 A1 | 1/2002 |
| EP | 1343481 A2 | 6/2002 |
| EP | 1143940 B1 | 4/2006 |
| EP | 2043613 A1 | 1/2008 |
| EP | 2076251 A2 | 7/2009 |
| EP | 2170282 A2 | 4/2010 |
| EP | 2214478 A1 | 8/2010 |
| EP | 2442793 A1 | 12/2010 |
| EP | 2377526 A1 | 10/2011 |
| EP | 2566467 A1 | 11/2011 |
| EP | 2431028 A2 | 3/2012 |
| EP | 2549988 A1 | 1/2013 |
| EP | 2632429 A1 | 9/2013 |
| EP | 2632443 A2 | 9/2013 |
| EP | 2674154 A2 | 12/2013 |
| EP | 2765989 A1 | 8/2014 |
| EP | 2632443 B1 | 9/2014 |
| EP | 2674154 A4 | 4/2015 |
| EP | 2821066 A2 | 7/2015 |
| EP | 2821066 A4 | 10/2015 |
| EP | 2765989 B1 | 4/2016 |
| EP | 3003285 A1 | 4/2016 |
| EP | 3069716 A1 | 9/2016 |
| EP | 3108876 A1 | 12/2016 |
| EP | 3368084 A1 | 5/2017 |
| EP | 3229778 A1 | 10/2017 |
| EP | 2431028 B1 | 12/2017 |
| EP | 2674154 B1 | 1/2018 |
| EP | 2821066 B1 | 4/2018 |
| WO | 2000/042992 A2 | 7/2000 |
| WO | 2002/005820 A1 | 1/2002 |
| WO | 2002/047607 A2 | 6/2002 |
| WO | 2003/003957 A1 | 1/2003 |
| WO | 2003/086345 A1 | 10/2003 |
| WO | 2004/087111 A1 | 10/2004 |
| WO | 2005/016321 A1 | 2/2005 |
| WO | 2007/093305 A2 | 8/2007 |
| WO | 2007/093305 A3 | 8/2007 |
| WO | 2008/008120 A1 | 1/2008 |
| WO | 2008/040534 A2 | 4/2008 |
| WO | 2008/040534 A3 | 4/2008 |
| WO | 2008/140459 A1 | 11/2008 |
| WO | 2008/140460 A1 | 11/2008 |
| WO | 2008/140461 A1 | 11/2008 |
| WO | 2009/002084 A3 | 12/2008 |
| WO | 2009/045022 A2 | 4/2009 |
| WO | 2009/052421 A1 | 4/2009 |
| WO | 2009/074995 A1 | 6/2009 |
| WO | 2010/044736 A1 | 4/2010 |
| WO | 2010/070617 A1 | 6/2010 |
| WO | 2010/146407 A9 | 12/2010 |
| WO | 2010/150930 A1 | 12/2010 |
| WO | 2010/151020 A2 | 12/2010 |
| WO | 2011/117313 A1 | 9/2011 |
| WO | 2011/138049 A1 | 11/2011 |
| WO | 2012/055944 A1 | 5/2012 |
| WO | 2012/055947 A2 | 5/2012 |
| WO | 2012/108738 A2 | 8/2012 |
| WO | 2012/108738 A3 | 8/2012 |
| WO | 2012/121461 A1 | 9/2012 |
| WO | 2013/056159 A1 | 4/2013 |
| WO | 2013/085224 A1 | 6/2013 |
| WO | 2013/129889 A3 | 6/2013 |
| WO | 2013/129889 A9 | 6/2013 |
| WO | 2013/129889 A2 | 9/2013 |
| WO | 2014/027975 A2 | 2/2014 |
| WO | 2014/137189 A1 | 12/2014 |
| WO | 2014/196916 A1 | 12/2014 |
| WO | 2015/026054 A1 | 2/2015 |
| WO | 2015/072684 A1 | 5/2015 |
| WO | 2015/184317 A1 | 12/2015 |
| WO | 2016/094567 A1 | 6/2016 |
| WO | 2017/072774 A1 | 5/2017 |
| WO | 2018/127938 A1 | 7/2018 |

\* cited by examiner

ORAL SOLUBLE FILM CONTAINING SILDENAFIL CITRATE

RELATED U.S. APPLICATION DATA

This application claims priority to U.S. provisional patent application No. 63/012,988 filed on Apr. 21, 2020; the contents of which are incorporated by reference herein in its entirety.

BACKGROUND OF THE INVENTION

Sildenafil, sold under the brand name Viagra® among others, is a medication used to treat erectile dysfunction (ED) and pulmonary arterial hypertension (PAH). It is taken by mouth, or injection into a vein. Sildenafil acts by blocking phosphodiesterase 5 (PDE5), an enzyme that promotes breakdown of cGMP, which regulates blood flow in the penis. It requires sexual arousal, however, to work for ED. It also results in dilation of the blood vessels in the lungs.

Pfizer originally discovered the medication in 1989 while looking for a treatment for heart-related chest pain. It was approved for medical use in the United States and in the European Union in 1998. In 2017, it was the 217th most commonly prescribed medication in the United States, with more than two million prescriptions. In 2017, it became available as a generic medication after final patents by Pfizer expired. In the United Kingdom, it is available over the counter.

The primary indication of sildenafil is the treatment of erectile dysfunction (inability to sustain a satisfactory erection to complete sexual intercourse). Its use is now one of the standard treatments for erectile dysfunction, including for men with diabetes mellitus.

Across multiple dosage forms, drawbacks exist with the use of sildenafil. For example, with Viagra® oral tablets (and generic versions thereof), patients often risk the shame and embarrassment of being seen administering the drug. That is, often times the drug cannot be taken in a discreet manner (within a short window of time), without the sexual partner(s) becoming aware of the need for the treatment of erectile dysfunction by the patient. In addition to the social stigma of erectile dysfunction, the oral tablets are not convenient to carry on the patient's possession, e.g., in a pocket or wallet. While transported by the patient, risks exist with the dosage form inadvertently being crushed and/or contaminated. Many patients also experience difficulties in swallowing oral tablets (e.g., dysphagia), especially in the absence of a liquid beverage. Understandably, the fear of choking can contribute to the level of anxiety with patients, especially within the context and circumstances of a romantic encounter.

As an alternative to tablets and pills, oral soluble films may be used to deliver active ingredients. The films can be formulated to disintegrate upon oral administration to rapidly (e.g., on the order of seconds) release the active ingredient. Examples of rapidly disintegrating films include films based on hydroxypropyl cellulose, hydroxypropylmethyl cellulose, and polyvinylpyrrolidone.

The following products have been approved by the FDA: BELBUCA® (buprenorphine hydrochloride) buccal film; BUNAVAIL™ (buprenorphine hydrochloride; naloxone hydrochloride) buccal film; SUBOXONE® (buprenorphine hydrochloride; naloxone hydrochloride) sublingual buccal film; SYMPAZAN® (clobazam) oral film; ZUPLENZ® (ondansetron) oral film; EXSERVAN™ (riluzole) oral film; and KYNIIVIOBI™ (apomorphine hydrochloride) sublingual film.

Significant limitations generally exist with OSFs. First, to date the amount of API (drug loading) included in OSFs has been limited. Typically, the API is dissolved within the film. However, an increase in drug load often leads to an increase in brittleness and longer disintegration times. Second, bitter tasting APIs present challenges when formulating the OSF. The order of addition of the formulation might be sufficient to mask the bitter taste of the API. Alternatively, bitter tasting APIs can be masked before incorporating into the OSF. To enhance the taste, different techniques can be used, but the simplest method includes mixing and co-processing of a bitter tasting API with excipient(s) having a good or pleasant taste (the method is referred to as the obscuration technique, and the excipient can include, e.g., a flavoring agent and/or taste masking agent). Selection of the appropriate flavoring agent or taste masking agent is challenging, as it is not readily apparent which ones will be effective, given a desired (bitter tasting) API and the corresponding remaining excipients. Additionally, the flavoring agent or taste masking agent can inadvertently alter the physical and/or performance characteristics of the OSF, which can regrettably lead to the need to reformulate.

OSFs containing sildenafil citrate are currently known, and several are commercially available. However, it is currently believed that no OSF containing sildenafil citrate has received approval from the United States Food and Drug Administration (FDA), to be marketed and sold in the United States, for the safe and effective treatment of ED or PAH.

SUMMARY OF THE INVENTION

An aspect of the present invention relates to an oral soluble film for releasing the active ingredient sildenafil (as the free base, or as a pharmaceutically acceptable salt thereof, e.g., sildenafil citrate) into the oral cavity and delivering, e.g., enterally via ingestion. Another aspect of the present invention relates to an oral soluble film that can be used to administer the active ingredient, at an amount sufficient and effective to (1) obtain a desired result, such as the treatment of the subject, and to (2) obtain a desired level of the active ingredient in the subject (as evidenced by, e.g., plasma levels of the active ingredient). The composition of the oral soluble film includes the active ingredient, in combination with multiple excipients (e.g., binder, filler, flavoring agent, plasticizer, sweetening agent, coloring agent, preservative, and solvent), present in an amount effective to achieve desired physical and performance characteristics of the oral soluble film, both in vitro and in vivo.

Across multiple embodiments, the OSF described herein can independently possess one or more advantages relative to other OSFs and/or traditional dosage forms (e.g., tablets and capsules). The one or more advantages can relate to, e.g., physical characteristics and/or performance characteristics of the oral soluble film. For example, in specific embodiments, the OSF can be in the form of a unit dose having a requisite drug load, while having acceptable physical dimensions (e.g., length, width, and thickness), mass, and water content; and while also exhibiting a desired disintegration time and pharmacokinetic (PK) profile. In specific embodiments, the variation of active ingredient between two equally sized unit dosages is relatively small. In specific embodiments, accuracy in the administered dose can be assured from every strip or film. In specific embodiments, the unit dose has a suitable breaking strength, elongation strength, loss on drying (LOD), surface area, and/or density. In specific embodiments, the OSF is flexible, compliant, and not brittle. In specific embodiments, the OSF does not have an unpleasant taste (e.g., the bitter taste of the active ingredient is effectively masked). In specific embodiments, the OSF does not have an unpleasant mouth feel. In specific embodiments, upon administration to the subject, the oral soluble film exhibits a suitable pharmacokinetic (PK) profile that includes, e.g., AUC, $C_{max}$, $t_{max}$, and/or $t_{1/2}$. In specific embodiments, relative to an oral tablet having an equivalent amount of sildenafil citrate (e.g., Viagra®), administration of the oral soluble film results in a lower incidence, severity, and/or duration of one or more adverse reactions. In specific embodiments, a single dose of the oral soluble film is individually packaged and sealed with a primary packaging material. In specific embodiments, a single dose of strip can be individually packaged without requiring a secondary container. Individually packaged OSFs are typically more difficult to tamper with, compared to traditional packages for tablets and capsules, such as bottles or foil blister packs. Additionally, many consumers may prefer the convenience to carry individually packaged OSFs. In specific embodiments, the individually packaged OSF can be easily handled, stored, and transported. In further specific embodiments, the primary packaging material forms a primary package that protects the oral soluble film from light, protects the oral soluble film from microbial contamination, is child resistant, is a barrier to moisture and vapor, is airtight, and/or mitigates leachable(s) into the oral soluble film. In specific embodiments, the OSF can easily be titrated. In specific embodiments, the OSF can be discretely administered. In specific embodiments, the OSF can be administered in the absence of water or beverage. This makes the dosage form acceptable among pediatric and geriatric patients, as well as patients with a fear of choking (e.g., those suffering from dysphagia).

The present invention provides for an oral soluble film that includes: (a) sildenafil citrate, (b) binder, (c) filler, (d) flavoring agent, (e) plasticizer, (f) sweetening agent, (g) preservative, (h) solvent, and (i) optionally coloring agent.

The present invention provides for an oral soluble film that includes: (a) sildenafil citrate; (b) binder that includes: (i) polyvinyl alcohol (PVA); (ii) polyvinyl alcohol (PVA)-polyethylene glycol (PEG) graft copolymer; and (iii) silicon dioxide; (c) filler; (d) flavoring agent that includes peppermint flavoring; (e) plasticizer; (f) sweetening agent; (g) preservative; (h) solvent that includes water; and (i) coloring agent.

The present invention also provides for an oral soluble film that includes: (a) sildenafil citrate; (b) binder that includes: (i) polyvinyl alcohol (PVA); (ii) polyvinyl alcohol (PVA)-polyethylene glycol (PEG) graft copolymer; and (iii) silicon dioxide; (c) filler that includes microcrystalline cellulose; (d) flavoring agent; (e) plasticizer that includes glycerin; (f) sweetening agent; (g) preservative; (h) solvent that includes water; and (g) optionally coloring agent.

The present invention also provides for an oral soluble film that includes: (a) sildenafil citrate; (b) binder that includes: (i) polyvinyl alcohol (PVA); (ii) polyvinyl alcohol (PVA)-polyethylene glycol (PEG) graft copolymer; and (iii) silicon dioxide; (c) filler that includes microcrystalline cellulose; (d) flavoring agent that includes peppermint flavoring; (e) plasticizer; (f) sweetening agent; (g) preservative; (h) solvent that includes water; and (i) coloring agent.

The present invention also provides for an oral soluble film that includes: (a) sildenafil citrate; (b) binder that includes: (i) polyvinyl alcohol (PVA); (ii) polyvinyl alcohol (PVA)-polyethylene glycol (PEG) graft copolymer; and (iii) silicon dioxide; (c) filler that includes microcrystalline cellulose; (d) flavoring agent that includes peppermint flavoring; (e) plasticizer that includes glycerin; (f) sweetening agent that includes sucralose and acesulfame potassium (ACE-K); (g) preservative that includes sodium benzoate; (h) solvent that includes water; and (i) optionally coloring agent.

The present invention also provides for an oral soluble film that includes: (a) sildenafil citrate; (b) binder that includes: (i) polyvinyl alcohol (PVA); (ii) polyvinyl alcohol (PVA)-polyethylene glycol (PEG) graft copolymer; and (iii) silicon dioxide; (c) filler that includes microcrystalline cellulose; (d) flavoring agent that includes peppermint flavoring; (e) plasticizer that includes glycerin; (f) sweetening agent that includes sucralose and acesulfame potassium (ACE-K); (g) coloring agent that includes FD&C Blue 1; (h) preservative that includes sodium benzoate; and (i) solvent that includes water.

The present invention also provides for an oral soluble film that includes: (a) 36±7 wt. % sildenafil citrate; (b) 30±6 wt. % binder that includes: (i) polyvinyl alcohol (PVA); (ii) polyvinyl alcohol (PVA)-polyethylene glycol (PEG) graft copolymer; and (iii) silicon dioxide; (c) 5.45±1 wt. % filler that includes microcrystalline cellulose; (d) 6.44±1.25 wt. % flavoring agent that includes peppermint flavoring; (e) 12±2.5 wt. % plasticizer that includes glycerin; (f) 10±2 wt. % sweetening agent that includes sucralose and acesulfame potassium (ACE-K); (g) 0.01±0.002 wt. % coloring agent that includes FD&C Blue 1; and (h) 0.10±0.02 wt. % preservative that includes sodium benzoate.

The present invention also provides for an oral soluble film configured as a unit dose, wherein the unit dose of the oral soluble film includes: (a) 70.24±7 mg sildenafil citrate; (b) 58.53±12 mg binder that includes: (i) polyvinyl alcohol (PVA); (ii) polyvinyl alcohol (PVA)-polyethylene glycol (PEG) graft copolymer; and (iii) silicon dioxide; (c) 10.63±2 mg filler that includes microcrystalline cellulose; (d) 12.56±2.5 mg flavoring agent that includes peppermint flavoring; (e) 23.41±5 mg plasticizer that includes glycerin; (f) 19.5±4 mg sweetening agent that includes sucralose and acesulfame potassium (ACE-K); (g) 0.02±0.004 mg coloring agent that includes FD&C Blue 1; (h) 0.20±0.04 mg preservative that includes sodium benzoate; and (i) 9.76±2.25 mg solvent that includes water.

The present invention also provides for an oral soluble film that includes: sildenafil citrate, polyvinyl alcohol (PVA), polyvinyl alcohol (PVA)-polyethylene glycol (PEG) graft copolymer, silicon dioxide, microcrystalline cellulose, peppermint flavoring, glycerin, sucralose, acesulfame potassium (ACE-K), FD&C Blue 1, sodium benzoate, and water.

The present invention also provides for an oral soluble film that includes: 36±7 wt. % sildenafil citrate; 30±6 wt. % in the aggregate of polyvinyl alcohol (PVA), polyvinyl alcohol (PVA)-polyethylene glycol (PEG) graft copolymer, and silicon dioxide; 5.45±1 wt. % microcrystalline cellulose; 6.44±1.25 wt. % peppermint flavoring; 12±2.5 wt. % glycerin; 10±2 wt. % in the aggregate sucralose and acesulfame potassium (ACE-K); 0.01±0.002 wt. % FD&C Blue 1; and 0.10±0.02 wt. % sodium benzoate.

The present invention also provides for an oral soluble film that includes (based on an anhydrous oral soluble film):

| Amount (w/w) | Material/Component | Specification |
|---|---|---|
| 36.00 | Sildenafil Citrate | USP |
| 30.00 | Kollicoat ® Protect: | |
| | Kollicoat ® IR | USP/NF |
| | Polyvinylalcohol | USP/NF |
| | Silicon Dioxide | USP/NF |
| 5.45 | Microcrystalline Cellulose - Avicel ® PH-101 | NF, Ph. Eur., JP |
| 6.44 | Peppermint Flavor | Natural Flavor |
| 12.00 | Glycerin | USP |
| 6.00 | Sucralose | NF |
| 4.00 | Acesulfame Potassium | USP/NF, Ph. Eur., JP |
| 0.01 | Blue 1 colorant | FDC |
| 0.10 | Sodium Benzoate | NF |
| TOTAL | | |
| 100.00 | | |

The present invention also provides for an oral soluble film configured as a unit dose, wherein each unit dose of the oral soluble film includes (based on an anhydrous oral soluble film):

| Amount per unit (mg) | Material/Component | Primary Function(s) |
|---|---|---|
| 70.24 | Sildenafil Citrate | Active |
| 58.53 | Kollicoat ® Protect: | |
| | Kollicoat ® IR | Binder |
| | Polyvinylalcohol | |
| | Silicon Dioxide | |
| 10.63 | Microcrystalline Cellulose - Avicel ® PH-101 | Filler/Binder |
| 12.56 | Peppermint Flavor | Flavor |
| 23.41 | Glycerin | Plasticizer |
| 11.70 | Sucralose | Sweetener |
| 7.80 | Acesulfame Potassium | Sweetener |
| 0.02 | FD&C Blue 1 | Color |
| 0.20 | Sodium Benzoate | Preservative |
| TOTAL | | |
| 195.10 | | |

The present invention also provides for a slurry, suitable for forming an oral soluble film. The slurry includes: 16.8±2 wt. % sildenafil citrate; 14.1±3 wt. % in the aggregate of polyvinyl alcohol (PVA), polyvinyl alcohol (PVA)-polyethylene glycol (PEG) graft copolymer, and silicon dioxide; 2.5±0.5 wt. % microcrystalline cellulose; 3.0±0.75 wt. % peppermint flavoring; 5.6±1.25 wt. % glycerin; 4.66±1 wt. % in the aggregate sucralose and acesulfame potassium (ACE-K); 0.005±0.001 wt. % FD&C Blue 1; 0.05±0.01 wt. % sodium benzoate; and 53.3±10 wt. % water.

The present invention also provides for a single dose of the oral soluble film described herein, that is individually packaged and sealed with a primary packaging material. The primary packaging material includes multiple layers, wherein at least one layer is manufactured from metalized polyester. The primary packaging material forms a primary package that (i) protects the oral soluble film from light, (ii) protects the oral soluble film from microbial contamination, (iii) is child resistant, (iv) is a barrier to moisture and vapor, (v) is airtight, (vi) mitigates leachable(s) into the oral soluble film, (vii) identifies a logo and/or includes printed indicia, or (viii) any combination thereof.

The present invention also provides for a kit that includes an enclosure that contains (a) multiple doses of the oral soluble film described herein, each individually packaged and sealed with a primary packaging material, and (b) prescribing information. The primary packaging material includes multiple layers, wherein at least one layer is manufactured from metalized polyester. The primary packaging material forms a primary package that (i) protects the oral soluble film from light, (ii) protects the oral soluble film from microbial contamination, (iii) is child resistant, (iv) is a barrier to moisture and vapor, (v) is airtight, (vi) mitigates leachable(s) into the oral soluble film, (vii) identifies a logo and/or includes printed indicia, or (viii) any combination thereof.

The present invention also provides for a method of medical treatment that includes orally administering to a subject in need thereof, the oral soluble film described herein.

The present invention also provides for a method of treating a disease or disorder ameliorated by sildenafil citrate, the method includes orally administering to a subject in need thereof, the oral soluble film described herein.

The present invention also provides for a method of treating erectile dysfunction (ED) in a male subject, the method includes orally administering to the male subject in need thereof an oral soluble film described herein.

The present invention also provides for a method of treating antidepressant-induced erectile dysfunction in a male subject, the method includes orally administering to the male subject in need thereof an oral soluble film described herein.

The present invention also provides for a method of treating pulmonary arterial hypertension (PAH) in a subject, the method includes orally administering to the subject in need thereof an oral soluble film described herein.

DETAILED DESCRIPTION OF THE INVENTION

An aspect of the present invention relates to an oral soluble film for releasing the active ingredient sildenafil (as the free base, or as a pharmaceutically acceptable salt thereof, e.g., sildenafil citrate) into the oral cavity and delivering, e.g., enterally via ingestion. Another aspect of the present invention relates to an oral soluble film that can be used to administer the active ingredient, at an amount sufficient and effective to (1) obtain a desired result, such as the treatment of the subject, and/or to (2) obtain a desired level of the active ingredient in the subject (as evidenced by, e.g., plasma levels of the active ingredient). The composition of the oral soluble film includes the active ingredient, in combination with multiple excipients (e.g., binder, filler, flavoring agent, plasticizer, sweetening agent, coloring agent, preservative, and solvent), present in an amount effective to achieve the desired physical and performance characteristics of the oral soluble film, both in vitro and in vivo. This includes, e.g., effectively masking the taste of the active ingredient, which is highly bitter. This is accomplished while employing only those excipients (in amounts) that will be permitted by FDA. This may be further accomplished by obtaining an oral soluble film that is suitable for regulatory approval, as well as improving medication adherence and compliance by the subject. Likewise, this in turn may be accomplished by providing for an oral soluble film having the requisite physical and performance characteristics. These characteristics can include, e.g., the desired and targeted: in vitro disintegration time, in vitro dissolution time, loss on drying (LOD), breaking strength, minimal foreign body sensation, elongation strength, PK parameters (e.g., $C_{max}$, $T_{max}$, $t_{1/2}$, AUC), mass/weight, thickness, moisture content, density, pH, drug load (content of API), elongation, and/or drug content uniformity (CU).

The present invention can be more readily understood by reading the following detailed description of the invention and study of the included examples.

As used herein, the following terms have the meanings ascribed to them unless specified otherwise.

The terms "comprise," "comprising," "include," "including," and "includes" when used in this specification and claims are intended to specify the presence of stated substances, features, integers, components, or steps, but they do not preclude the presence or addition of one or more other substances, features, integers, components, steps, or combinations thereof.

The term "about" modifies the subject values, such that they are within an acceptable error range, as determined by one of ordinary skill in the art, which will depend in part on the limitations of the measurement system.

The articles "a" and "an" as used herein refers to "one or more" or "at least one," unless otherwise indicated. That is, reference to any element or component of an embodiment by the indefinite article "a" or "an" does not exclude the possibility that more than one element or component is present.

The term "excipient" refers to a pharmacologically inactive substance used in the pharmaceutical preparation of oral solid dosage forms (e.g., oral soluble film). An excipient is a substance formulated alongside the active pharmaceutical ingredient (API), and can include agents for stabilizing, bulking/filling, disintegrating, dissolving, flavoring, facilitating drug absorption, reducing viscosity, and/or enhancing solubility. Excipients can also be useful in the manufacturing process, to aid in the handling of the API, such as by facilitating powder flowability or non-stick properties, and/or aiding in vitro stability such as prevention or mitigation of degradation of the API over the expected shelf life. The selection of appropriate excipients also depends upon the route of administration and the dosage form, as well as the API and other factors. Pharmaceutical regulations and standards require that all ingredients in drug products, as well as their chemical decomposition products, be identified and shown to be safe. The Federation of International Pharmaceutical Excipients Council (IPEC), a pharmaceutical regulatory non-profit, develops, implements, and promotes global use of appropriate quality, safety, and functionality standards for pharmaceutical excipients and excipient delivery systems.

Excipients useful in the formulations described herein (e.g., slurry and OSF) include, e.g., binder, filler, preservative, sweetening agent, solvent, co-solvent, plasticizer, flavoring agent, taste masking agent, colorant, anti-caking agent, coating agent, emulsifier, solubilizing agent, lipid, humectant, thickening agent, lubricant, adsorbent, suspending agent, disintegrating agent, permeation enhancer, saliva stimulating agent, release modifier, adjuvant, fragrance, surfactant, pH adjusting agent, buffering agent, stabilizer, and antioxidant. Excipients that can be used in the formulation of oral soluble films are described in, e.g., Lachman, et al., "The Theory and Practice of Industrial Pharmacy," $4^{th}$ Edition (2013); Sheskey et al., "Handbook of Pharmaceutical Excipients," 9th Edition (2020); and Remington, "The Science and Practice of Pharmacy," 22nd Edition (2015). All excipients used in the formulation of the oral soluble film described herein, in the desired amounts, should preferably be approved by the FDA for use in oral pharmaceutical dosage forms. See, e.g., the FDA Inactive Ingredient Database (IID), https://www.accessdata.fda.gov/scripts/cder/iig/index.cfm (accessed Apr. 15, 2021). Additionally, the excipients will preferably be commercially available in acceptable grade, physiologically inert, and physically and chemically stable by themselves, as well as in combination with the desired API.

Sildenafil (as the free base, or as a pharmaceutically acceptable salt thereof, e.g., sildenafil citrate) functions as an active ingredient in the oral soluble film described herein. In specific embodiments, the sildenafil functions as the sole active ingredient. Likewise, one or more excipients used in the pharmaceutical preparation of the oral soluble films described herein can possess a single use or function. In specific embodiments, when present in the oral soluble film described herein, each of sucralose and acesulfame potassium (ACE-K) function as a sweetener. In specific embodiments, when present in the oral soluble film described herein, FD&C Blue 1 functions as a colorant. Additionally, in specific embodiments, when present in the oral soluble film described herein, sodium benzoate functions as a preservative. Without being limited or bound to any particular theory, it is believed that across multiple specific embodiments, these substances provide little or no additional function(s) than those ascribed above.

In contrast, in specific embodiments, one or more excipients employed in the oral soluble film described herein can have multiple uses or functions. For example, when present in the oral soluble film described herein, Kollicoat® Protect is employed as a binder, but in specific embodiments can further function as an anti-caking agent, disintegrating agent, coating agent, taste masking agent, emulsifier, to increase tensile strength of the OSF, to increase elongation of the OSF, or any combination thereof. When present in the oral soluble film described herein, natural peppermint flavor is employed as a flavoring agent, but in specific embodiments can further function as a taste masking agent, permeation enhancer, or combination thereof. When present in the oral soluble film described herein, glycerin is employed as a plasticizer, but in specific embodiments can further function as a sweetener, humectant, co-solvent, thickening agent, lubricant, or any combination thereof. When present in the oral soluble film described herein, microcrystalline cellulose is employed as a filler, but in specific embodiments can further function as an anti-caking agent, emulsifier, bulking agent, binder, viscosity increasing agent, or any combination thereof.

In specific embodiments, the present invention provides for an oral soluble film that includes (i) sildenafil citrate, (ii) binder, (iii) filler, (iv) flavoring agent, (v) plasticizer, (vi) sweetener, (vii) coloring agent, and (viii) preservative. It is contemplated that in specific embodiments, one or more excipients can be employed in the oral soluble film, each to effectively serve multiple functions. For example, in specific embodiments, a single excipient (e.g., Kollicoat® Protect) can function as a binder, as well as an anti-caking agent, disintegrating agent, coating agent, taste masking agent, binder, emulsifier, to increase tensile strength of the OSF, and/or to increase elongation of the OSF. In specific embodiments, a single excipient (e.g., Peppermint Flavor) can function as a flavoring agent, as well as a permeation enhancer and/or taste masking agent. In specific embodiments, a single excipient (e.g., glycerin) can function as a plasticizer, as well as a sweetener, humectant, co-solvent, thickening agent, and/or lubricant. Excipients useful in the oral soluble film described herein, having multiple functions, are described, e.g., in Handbook of Pharmaceutical Excipients, Sheskey et al., Eds., 9th Edition, Pharmaceutical Press (2020).

The OSF may be prepared by first forming a slurry. In forming a slurry, any one or more of the ingredients (including the API) employed can effectively be dissolved or dispersed therein (e.g., in the solvent). This includes, e.g., salts, such as sodium benzoate and acesulfame potassium. This also extends to the drug substance, sildenafil citrate. In doing so, the salt can dissociate into the respective anion and cation; and would therefore no longer necessarily exist in the salt form—benzoic acid, acesulfame free base, and sildenafil free base. However, within the context of the present invention, it is appreciated that those of skill in the art understand and agree that reference to the slurry (and resulting oral soluble film) as containing substances in the salt form is otherwise acceptable and appropriate.

Additionally, in specific embodiments, the inactive ingredient microcrystalline cellulose can be employed in the manufacture of the drug product, oral soluble film. In forming the slurry, the microcrystalline cellulose present can effectively be dissolved or dispersed therein (e.g., in the solvent). In doing so, the cellulose would therefore no longer necessarily retain the microcrystalline form. However, within the context of the present invention, it is appreciated that those of skill in the art understand and agree that reference to the slurry (and resulting oral soluble film) as containing microcrystalline cellulose (e.g., cellulose in the microcrystalline form) is otherwise acceptable and appropriate.

Likewise, in specific embodiments, the drug substance sildenafil citrate, having a specified bulk density or particle size distribution (PSD), can be employed in the manufacture of the drug product, oral soluble film. In forming the slurry, the sildenafil citrate present can effectively be dissolved or dispersed therein (e.g., in the solvent). In doing so, the sildenafil citrate would therefore no longer necessarily retain the drug substance PSD or bulk density. However, within the context of the present invention, it is appreciated that those of skill in the art understand and agree that reference to the slurry (and resulting oral soluble film) as containing the sildenafil citrate having a specified bulk density or PSD (based on the drug substance sildenafil citrate employed) is otherwise acceptable and appropriate.

Additionally, in specific embodiments, the inactive ingredient microcrystalline cellulose (MCC), having a specified bulk density or particle size distribution (PSD), can be employed in the manufacture of the drug product, oral soluble film. In forming the slurry, the MCC present can effectively be dissolved or dispersed therein (e.g., in the solvent). In doing so, the MCC would therefore no longer necessarily retain the PSD. However, within the context of the present invention, it is appreciated that those of skill in the art understand and agree that reference to the slurry (and resulting oral soluble film) as containing the MCC having a specified PSD (based on the MCC employed) is otherwise acceptable and appropriate.

Reference can therefore be made to the slurry (and the resulting oral soluble film) as containing (or as being manufactured from, or as being formed from) various substances, such as the active ingredient (e.g., sildenafil citrate) and multiple excipients (e.g., binder, filler, flavoring agent, plasticizer, sweetening agent, coloring agent, preservative, and/or solvent). As described herein, within the context of the present invention, it is appreciated that those of skill in the art understand and agree that reference to the slurry (and the resulting oral soluble film) as containing the active ingredient and excipients is acceptable and appropriate. This is so, even though those substances may no longer necessarily exist in the same state as when introduced into the slurry, as specifically indicated. Likewise, within the context of the present invention, reference can also be made to the slurry (and the resulting oral soluble film) as being manufactured from (or as being formed from) the active ingredient and excipients, as specifically indicated. It is appreciated that those of skill in the art understand and agree that each of the above characterizations of the slurry (and the resulting oral soluble film) are acceptable and appropriate.

The term "inactive ingredient" (and equivalent terms such as "inactive component") refers to a substance that is pharmacologically and biologically inactive. The inactive ingredients are usually called excipients in pharmaceutical contexts.

The term "slurry" refers to a mixture of solids that is dispersed, suspended, solubilized, and/or dissolved in liquid. Together, the solids and liquid will include those substances used to manufacture the oral soluble film. The solid substances employed in the manufacture of the oral soluble film can essentially be dissolved in the liquid, can essentially be suspended in the liquid, can essentially be dispersed in the liquid, can essentially be solubilized in the liquid, or a combination thereof. An oral soluble film can be formed by curing a cast slurry. The curing can be carried out, e.g., at an elevated temperature, for a period of time. In doing so, a significant amount of the solvent (e.g., water) will be removed. The remaining water will contribute to the moisture content in the oral soluble film (in addition to any moisture from the surrounding environment that is picked up by any hygroscopic polymers employed).

The term "binder" (and equivalent terms such as "binding agent") refers to a substance, typically a polymer, used in the pharmaceutical preparation of oral solid dosage forms (e.g., oral soluble film) to hold the ingredients together. Binders ensure that the oral soluble films can be formed with the requisite mechanical strength. The binders also provide the requisite volume to low amount of active present in soluble films. The presence of the binder can also facilitate the formation of the cured film. As such, the binder includes those substances, which when present in the cast slurry and upon curing, will effectively provide for a cured film. In designing of an oral soluble film formulation, consideration should be given to the target product and drug release profile. A primary component of an oral film is the binder, which may be a polymer blend. Selection of the binder may be guided by the desired strength and stability of the oral soluble film, as well as mucoadhesiveness, pliability, dissolution rate, and moisture content. The binder may also be referred to as a "film forming agent," or more specifically a "film forming polymer" (or equivalent terms, such as "strip-forming polymer" and "mucoadhesive polymer") when it is a polymer. Polymeric binders (film forming agents) can be natural or a synthetic. Employing a binder can allow for, and promote, the formation of a "film matrix" (also referred to as a polymeric matrix). A film matrix is typically obtained by curing the cast slurry, which contains the binder(s). Examples of binders for use in an OSF described herein include polyacrylic acid (PAA) (alternatively referred to as poly(acrylic acid) or Carbomer®); 1-polyacrylic acid; methyl methacrylate copolymer; carboxyvinyl polymer; polyethylene glycol (PEG) (alternatively referred to as polyethylene oxide or PEO); acacia; agar; alginic acid (alternatively referred to as algin); sodium alginate (Na alginate); calcium carbonate; calcium lactate; carboxymethyl cellulose (CMC) (alternatively referred to as cellulose gum or carboxy methylcellulose or carboxymethylcellulose); carrageenan; cellulose acetate; chitosan; copovidone; starch (e.g., corn starch or pregelatinized starch); cottonseed oil; dextrates;

dextrin; dextrose (alternatively referred to as corn sugar and D-glucose); ethylcellulose; (alternatively referred to as ethyl cellulose); gelatin; guar gum; hydroxyethyl cellulose (HEC); hydroxyethyl methyl cellulose (MEMC); hydroxypropyl methylcellulose (HPMC) (alternatively referred to as hydroxypropyl methyl cellulose, hypromellose, or INN) (e.g., Vivapharm® HPMC E3, Methocel™ HPMC K3, Vivapharm® HPMC E5, Vivapharm® HPMC E15, or Methocel™ E15); hydroxypropyl cellulose (HPC); low substituted hydroxypropyl cellulose (L-HPC); hydroxypropyl starch; inulin; lactose; maltodextrin; maltose; methylcellulose (MC) (e.g., Methocel® A15); microcrystalline cellulose (MCC) (e.g., Avicel® PH-101); pectin; poloxamer (e.g., Pluronic®, Kolliphor®, and Synperonic®); polycarbophil; polydextrose; polymethacrylates; polyvinyl alcohol (PVA) (alternatively referred to as poly(vinyl alcohol), polyvinylalcohol or PVOH or PVAl); polyvinylpyrrolidone (PVP) (alternatively referred to as polyvidone or povidone) (e.g., Kollidon® K90, Kollidon® 12 PF, Kollidon® 17 PF, Kollidon® 25 PF, or Kollidon® 30 PF); pullulan; sodium carboxymethylcellulose (CMC-Na) (alternatively referred to as sodium carboxymethyl cellulose) (e.g., Cekol® 30); sucrose; sunflower oil; zein; vinylpyrrolidone-vinyl acetate copolymer (e.g., Kollidon® VA64); polyvinyl acetate/polyvinylpyrrolidone (e.g., Kollidon® SR); polyvinyl alcohol-polyethylene glycol copolymer and polyvinyl alcohol (PVA) (e.g., Kollicoat® Protect); polyvinyl alcohol/polyethylene glycol graft copolymer (e.g., Kollicoat® IR); polyvinyl caprolactampolyvinyl acetate-polyethylene glycol graft copolymer (e.g., Soluplus®); poly(ethyl acrylate-co-methyl methacrylate-co-trimethylammonioethyl methacrylate chloride) (e.g., Eudragit® RL100); amino methacrylate copolymer (e.g., Eudragit® E PO); and xanthan gum.

The term "filler" (and equivalent terms such as "diluent" and "bulking agent") refers to substances used in the pharmaceutical preparation of oral solid dosage forms (e.g., oral soluble film) to add bulk to the pharmaceutical dosage form, improving the consistency in dose metering and/or making the active ingredient easier for consumer to take. Fillers can also help with the manufacturing and stabilization of these products. Fillers can also bind and stabilize the dosage form. They are employed in the manufacture of an OSF to increase weight/mass and/or to improve content uniformity. Fillers can provide properties such as improved cohesion and/or to promote flow. Examples of fillers for use in an OSF described herein include anhydrous lactose, calcium carbonate, calcium lactate, calcium phosphate (dibasic anhydrous, dibasic dihydrate, or tribasic), calcium silicate, calcium sulfate, cellulose (powdered or silicified microcrystalline), cellulose acetate, corn starch and pregelatinized starch, dextrates, dextrin, dextrose, erythritol, ethylcellulose, fructose, fumaric acid, glucose, glyceryl palmitostearate, glycine, hydrolyzed starch, lactose, lactose monohydrate, isomalt, kaolin, lactitol, magnesium carbonate, magnesium oxide, maltodextrin, maltose, mannitol, medium-chain triglycerides, microcrystalline cellulose (MCC), partially pregelatinized starches, plant cellulose, polydextrose, polymethacrylates, simethicone, sodium alginate, sodium chloride, sorbitol, pregelatinized starch, sterilizable maize, sucrose, sugar spheres, sulfobutylether β-cyclodextrin, talc, tragacanth, trehalose, and xylitol.

The term "preservative" refers to a substance used in the pharmaceutical preparation of oral solid dosage forms (e.g., oral soluble film), to prevent or mitigate microbial growth or by undesirable chemical changes. In general, preservation is implemented in two modes, chemical and physical. Examples of preservatives for use in an OSF described herein include ethanol, benzoic acid, benzyl alcohol, butylated hydroxyanisole (BHA), butylated hydroxytoluene (BHT), butylparaben, calcium acetate, calcium chloride, calcium lactate, cetylpyridinium chloride, chlorhexidine, chlorobutanol, citric acid monohydrate, ethylparaben, glycerin, lactic acid, methylparaben, parabens, potassium benzoate, potassium sorbate, propyl gallate, propylene glycol, propylparaben, propylparaben sodium, sodium acetate, sodium benzoate, sodium lactate, sodium propionate, sorbic acid, sulfobutyl ether ß-cyclodextrin, edetic acid, xanthan, and xylitol.

The term "sweetening agent" (and equivalent terms such as "sweetener") refers to a substance used in the pharmaceutical preparation of oral solid dosage forms (e.g., oral soluble film), to impart a sweet taste like that of sugar. The sweetener can be artificial or naturally occurring. Examples of sweetening agents for use in an OSF described herein include sugar, acesulfame salts (e.g., acesulfame potassium (ACE-K)), alitame, aspartame, dextrose, erythritol, fructose, glycerin, isomalt, lactitol, advantame, monk fruit extract (mogrosides), glucose, galactose, maltitol, maltose, mannitol, monk fruit extract, neohesperidin dihydrochalcone, neotame, saccharin, saccharin salts (e.g., saccharin sodium), sodium cyclamate, sorbitol, stevia, stevioside, rebaudioside A, sucralose, sucrose, tagatose, thaumatin, trehalose, licorice extract, and xylitol.

The term "solvent" refers to a substance that is used in the pharmaceutical preparation of an oral soluble film, to dissolve the active pharmaceutical ingredient (API) and/or excipients. A solvent can be employed to form a slurry. For most manufacturing methods, solvents improve solubility of the active ingredient within the film forming matrix. Solvents may be chosen based on the active ingredient's solubility therein. Preferred solvents include volatile class 3 residual solvents such as ethanol and acetone and non-volatile solvents such as water. In some embodiments, the solvent is at least one of ethanol and water. Upon curing of a slurry to provide an oral soluble film, a significant portion of the solvent will typically be removed, leaving behind a remaining (or residual) portion of the solvent.

The term "co-solvent" refers to a substance that is used in the pharmaceutical preparation of an oral soluble film, to assist the solvent in dissolving the active pharmaceutical ingredient (API) and/or excipients, to form a slurry. Examples of co-solvents for use in an OSF described herein include almond oil, castor oil, corn oil, cottonseed oil, ethanol, glycerin, olive oil, polyethylene glycol, polyoxy 35 castor oil, propylene glycol, safflower oil, sesame oil, soybean oil, sunflower oil, and ethanol. Upon curing of a slurry to provide an oral soluble film, a portion of the co-solvent may be removed.

The term "plasticizer" refers to a substance that, when added to polymer(s), makes the polymer more pliable and softer, enhancing the flexibility and plasticity of the films. They can be added to reduce the glass transition temperature to reduce the risk of thermally destabilizing the active ingredient and/or excipients. The plasticizer is believed to permeate the polymer structure, disrupting intermolecular hydrogen bonding, and permanently lowers intermolecular attractions. Plasticizers can be used to allow initial film forming, to reduce the brittleness, and improve the processability and flexibility of the resulting film, thereby avoiding cracking, e.g., during the curing process. Plasticizers can be used to improve elasticity of the oral soluble film which can be important for manufacturing scale-up. Plasticizers can also play a role when combined with certain polymers in the overall dissolution rate of the film. Examples of plasticizers for use in an OSF described herein include castor oil, glycerin, glycerol monostearate, D, hypromellose phthalate, mannitol, mineral oil and, palmitic acid, polyethylene glycol, polyvinyl acetate phthalate, propylene glycol, pyrrolidone, sorbitol, stearic acid, triacetin, tributyl citrate, triethyl citrate, water, glycerin fatty acid esters, sucrose fatty acid esters, lecithin, enzyme modified lecithin, polysorbates, sorbitan fatty acid esters, maltitol, xylitol, polyethylene glycol (PEG), hydrogenated starch syrup, starch syrup, and glycerol oleate.

The term "flavoring agent" (and equivalent terms such as "flavoring substance," "flavor," "flavoring," and "flavorant") refers to a substance used in the pharmaceutical preparation of an oral soluble film, to impart a flavor, e.g., to improve the attractiveness and acceptance by the subject. The basic taste sensations are salty, sweet, bitter, sour, and umami. Flavors may be chosen from natural and synthetic flavorings. An illustrative list of such agents includes volatile oils, synthetic flavor oils, flavoring aromatics, oils, liquids, oleoresins or extracts derived from plants, leaves, flowers, fruits, stems and combinations thereof. The flavoring agent can be available as a solid (e.g., powder), as a liquid (e.g., oil), or a combination thereof. Additionally, the flavoring agent for use in the OSF can include any one or more of a natural flavoring substance, a nature-identical flavoring substance, and an artificial flavoring substance. Examples of flavoring agents for use in an OSF described herein include allspice, anise, n-butyl lactate, cardamom, cherry, confectioner's sugar, cinnamon, clove, ethyl vanillin, ethylcellulose, eugenol, ginger, gingermint, lemon, lemongrass, levomenthol, lime, malic acid, maltol, menthol, mint, nutmeg, orange, peppermint, phosphoric acid, propionic acid, sodium acetate, sodium lactate, spearmint, tangerine, tartaric acid, thymol, triethyl citrate, vanillin, vanilla cream, watermint, wintergreen, mountain berry, and grape. In specific embodiments, the peppermint flavoring agent can include Natural Peppermint Oil, commercially available from A. M. Todd; Natural Peppermint Flavor 501500 TPK504, commercially available from Firmenich (Anaheim, Calif.); or Natural and Artificial Peppermint, commercially available from Firmenich (Anaheim, Calif.). In specific embodiments, the spearmint flavoring agent can include Spearmint Flavor, Nat & Art, commercially available from FONA (Geneva, Ill.); or Natural Spearmint Flavor, commercially available from Virginia Dare (Brooklyn, N.Y.). In specific embodiments, the orange flavoring agent can include Nat Orange Durarome 860205 TD 1091, commercially available from Firmenich (Anaheim, Calif.); Orange Flavor Nat WONF, commercially available from FONA (Geneva, Ill.); Orange Flavor, Nat & Art, commercially available from FONA (Geneva, Ill.); or Superflex Natural Orange, commercially available from Virginia Dare (Brooklyn, N.Y.). In specific embodiments, the vanilla cream flavoring agent can include Natural Flavor for Cream (NFF Vanilla), commercially available from Virginia Dare (Brooklyn, N.Y.).

The term "natural flavoring substance" refers to a flavoring substance obtained from plant or animal raw materials, by physical, microbiological, or enzymatic processes. They can be either used in their natural state or processed for human consumption, but cannot contain any nature-identical or artificial flavoring substances.

The term "nature-identical flavoring substance" refers to a flavoring substance obtained by synthesis or isolated through chemical processes, which is chemically and organoleptically identical to flavoring substances naturally present in products intended for human consumption. They cannot contain any artificial flavoring substances.

The term "artificial flavoring substance" refers to a flavoring substance that is not identified in a natural product intended for human consumption, whether or not the product is processed. These are typically produced by fractional distillation and additional chemical manipulation of naturally sourced chemicals, crude oil, or coal tar. Although they are chemically different, in sensory characteristics they are the same as natural ones. Most artificial flavors are specific and often complex mixtures of singular naturally occurring flavor compounds combined together to either imitate or enhance a natural flavor. These mixtures are formulated by flavorists to give a food product a unique flavor and to maintain flavor consistency between different product batches or after recipe changes. The list of known artificial flavoring agents includes thousands of molecular compounds, and the flavor chemist (flavorist) can often mix these together to produce many of the common flavors. Many of these artificial flavorants consist of esters, which are often described as being "sweet" or "fruity".

The term "taste masking agent" refers to a substance used in the pharmaceutical preparation of an oral soluble film, to mask the unpleasant taste of a substance present in the formulation, to improve the attractiveness and acceptance by the subject. The taste masking agent can specifically refer to a substance used to mask the bitter or unpleasant taste of the active ingredient. Examples of taste masking agents for use in an OSF described herein include alginic acid, erythritol, and glyceryl palmitostearate, and monoammonium glycyrrhizinate (MAG). With the oral soluble films described herein, in addition to masking the taste of any unpleasant or bitter tasting substances (e.g., the active ingredient) present in the oral soluble film, the taste masking agent can optionally also impart a pleasant flavor. In such embodiments, the same substance can serve as both a flavoring agent and as a taste masking agent.

The term "colorant" (and equivalent terms such as "coloring agent") refers to substance used in the pharmaceutical preparation of an oral soluble film, to change the color of the slurry and/or oral soluble film. The colorant is a dye, pigment, or substance that imparts color when it is added to a slurry. Colorants work by absorbing varying amounts of light at different wavelengths (or frequencies) of its spectrum, transmitting (if translucent) or reflecting the remaining light in straight lines or scattered. Color consistency can be significant, as it allows easy identification of a medication to the subject. Furthermore, colors often improve the aesthetic look and feel of medications. By increasing these organoleptic properties, a subject is more likely to adhere to their schedule and therapeutic objectives will also have a better outcome for the subject. The colorant can include, e.g., FD&C colors (e.g., FD&C red, FD&C yellow, FD&C blue, FD&C green), D&C colors, or a combination thereof. Examples of colorants for use in an OSF described herein include FD&C Red No. 3, FD&C Red No. 40, FD&C Yellow No. 5, FD&C Yellow No. 6, FD&C Green No. 3, FD&C Blue No. 1, and FD&C Blue No. 2.

The term "anti-caking agent" (and equivalent terms such as "anti-tacking agent") refers to a substance used in the pharmaceutical preparation of oral solid dosage forms (e.g., oral soluble film), to prevent or mitigate the occurrence of the formation of lumps (caking) of powdered or granulated materials. Use of the anti-tacking agent can result in the ease of flowability of the solid powders used to form the slurry. Crystalline solids often cake by formation of liquid bridge and subsequent fusion of microcrystals. Amorphous materials can cake by glass transitions and changes in viscosity.

Examples of anti-caking agents for use in an OSF described herein include calcium silicate, tribasic calcium phosphate, colloidal silicon dioxide, hydrophobic colloidal silica, magnesium oxide, magnesium silicate, magnesium trisilicate, and talc, mannitol, and starch.

The term "coating agent" refers to a substance that is applied to a solid or powder particle, to sufficiently coat the particle. The thickness of such a coating is usually less than 100 µm. The motivation for coating a particle ranges from improving the stability (light protection, moisture and gas barrier) to increasing the flowability to thereby make it easier to process. Examples of coating agents for use in an OSF described herein include calcium carbonate, carboxymethylcellulose calcium, carboxymethylcellulose sodium, carnauba wax, cellulose acetate, (CAP), chitosan, ethylcellulose, fructose, gelatin, glycerin, glyceryl behenate, glyceryl palmitostearate, hydroxyethyl cellulose, hydroxypropyl cellulose, hypromellose, hypromellose phthalate, isomalt, glucose, maltitol, maltodextrin, methylcellulose, microcrystalline wax, poloxamer, polydextrose, polyethylene glycol, poly-DL-(lactic acid), polyvinyl acetate phthalate, polyvinyl alcohol, povidone, sucrose, titanium oxide, tributyl citrate, triethyl citrate, vanillin, xylitol, and zein.

The term "emulsifier" (and equivalent terms such as "emulsifying agent") refers to a substance capable of forming or promoting an emulsion. In particular reference to the oral soluble films described herein, the emulsifier can promote the separation of phases (e.g., aqueous and lipids), while allowing them to be mixed. Examples of emulsifiers for use in an OSF described herein include acacia, cholesterol, glycerin, glyceryl monostearate, hydroxypropyl cellulose, lecithin, methylcellulose, mineral oil and, monobasic sodium phosphate, monoethanolamine, oleic acid, polyethylene glycol, poloxamer, polyoxyethylene alkyl ethers, polyoxyethylene castor oil derivatives, polyoxyethylene sorbitan fatty acid esters, polyoxyethylene stearates, polysorbate (e.g., polysorbate 20, polysorbate 40, polysorbate 60, polysorbate 80, etc.), propylene glycol, propylene glycol alginate, sodium lauryl sulfate, sorbitan esters, and stearic acid.

The term "solubilizing agent" (and equivalent terms such as "solubilizer") refers to a substance used in the pharmaceutical preparation of an oral soluble film, to increase the solubility and/or bioavailability of the API. A solubilizing agent can act as a surfactant and increases the solubility of one agent in another. A substance that would not normally dissolve in a particular solution may be able to dissolve with the use of a solubilizing agent. Examples of solubilizing agents for use in an OSF described herein include cyclodextrins, glycerin monostearate, hydroxpropyl betadex, hypromellose, inulin, lecithin, meglumine, phospholipids, poloxamer, polyoxyethylene alkyl ethers, polyoxyethylene castor oil derivatives, polyoxyethylene sorbitan fatty acid esters, polyoxyethylene stearates, polyoxylglycerides, povidone, pyrrolidone, sorbitan esters, starch, stearic acid, sulfobutylether β-cyclodextrin, tricaprylin, triolein, and vitamin E polyethylene glycol succinate, N-acetylated amino-acid derivative, ethoxylated sorbitan, mono and diglycerides.

The term "emulsion" refers to a mixture of two or more liquids that are normally immiscible (unmixable or unblendable) owing to liquid-liquid phase separation. Two liquids can form different types of emulsions. As an example, oil and water can form, first, an oil-in-water emulsion, in which the oil is the dispersed phase, and water is the continuous phase. Second, they can form a water-in-oil emulsion, in which water is the dispersed phase and oil is the continuous phase. Multiple emulsions are also possible, including a "water-in-oil-in-water" emulsion and an "oil-in-water-in-oil" emulsion. Emulsions, being liquids, do not exhibit a static internal structure. The droplets dispersed in the continuous phase (sometimes referred to as the "dispersion medium") are usually assumed to be statistically distributed to produce roughly spherical droplets. When molecules are ordered during liquid-liquid phase separation, they form liquid crystals rather than emulsions. Lipids, used by all living organisms, are one example of molecules able to form either emulsions (e.g.: spherical micelles; Lipoproteins) or liquid crystals (lipid bilayer membranes). The droplets may be amorphous, liquid-crystalline, or any mixture thereof. The diameters of the droplets constituting the dispersed phase usually range from approximately 10 nm to 100 µm; i.e., the droplets may exceed the usual size limits for colloidal particles. An emulsion is termed an oil/water (o/w) emulsion if the dispersed phase is an organic material, and the continuous phase is water or an aqueous solution and is termed water/oil (w/o) if the dispersed phase is water or an aqueous solution and the continuous phase is an organic liquid (an "oil").

Two special classes of emulsions—microemulsions and nanoemulsions, with droplet sizes below 100 nm—appear translucent. This property is due to the fact that light waves are scattered by the droplets only if their sizes exceed about one-quarter of the wavelength of the incident light. Since the visible spectrum of light is composed of wavelengths between 390 and 750 nanometers (nm), if the droplet sizes in the emulsion are below about 100 nm, the light can penetrate through the emulsion without being scattered. Due to their similarity in appearance, translucent nanoemulsions and microemulsions are frequently confused. Unlike translucent nanoemulsions, which require specialized equipment to be produced, microemulsions may be spontaneously formed by "solubilizing" oil molecules with a mixture of surfactants, co-surfactants, and co-solvents. The required surfactant concentration in a microemulsion is, however, several times higher than that in a translucent nanoemulsion, and significantly exceeds the concentration of the dispersed phase. Because of many undesirable side-effects caused by surfactants, their presence is often considered disadvantageous or prohibitive in many applications. In addition, the stability of a microemulsion may be compromised by dilution, by heating, or by changing pH levels.

The term "lipid" refers to a group of naturally occurring molecules that include fats, waxes, sterols, fat-soluble vitamins (such as vitamins A, D, E, and K), monoglycerides, diglycerides, triglycerides, phospholipids, and others. "Lipid" may also refer to ethoxylated fatty alcohols such as oleth-10 and laureth-10 and mixtures of ethoxylated mono and diglycerides such as PEG-16 macadamia glycerides and PEG-10 sunflower glycerides. The compounds are hydrophobic or amphiphilic small molecules. The amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups. Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits). Although the term lipid is sometimes used as a synonym for fats, fats are a subgroup of lipids called triglycerides. Lipids also encompass molecules such as fatty acids and their derivatives (including tri-, di-, monoglycerides, and phospholipids), as well as other sterol-containing metabolites such as cholesterol. Examples of lipids for use in an OSF described herein include almond oil, argan oil, avocado oil, canola oil, cashew oil, castor oil, cocoa butter, coconut oil, colza oil, corn oil, cottonseed oil, grape seed oil, hazelnut oil, hemp oil, hydroxylated lecithin, lecithin, linseed oil, macadamia oil, mango butter, manila oil, mongongo nut oil, olive oil, palm kernel oil, palm oil, peanut oil, pecan oil, perilla oil, pine nut oil, pistachio oil, poppy seed oil, pumpkin seed oil, rice bran oil, safflower oil, sesame oil, Shea butter, soybean oil, sunflower oil, sunflower lecithin, walnut oil, and watermelon seed oil, vitamin E, mono and diglycerides, propylene glycol, polyethylene glycol, Kolliphor® RH, and Kolliphor® EL.

The term "humectant" refers to a substance used in the pharmaceutical preparation of an oral soluble film, to keep the slurry and/or oral soluble film moist. A humectant attracts and retains the moisture in the air nearby via absorption, drawing the water vapor into or beneath the oral soluble film's surface. This is the opposite use of a hygroscopic material where it is used as a desiccant used to draw moisture away. Humectants can be used in oral soluble films to help solubilize active ingredients, increasing the active ingredients' ability to penetrate a mucosal surface, or its activity time. Examples of humectants for use in an OSF described herein include glycerin, polydextrose, propylene glycol, sodium lactate, sorbitol, trehalose, triacetin, xylitol, sodium chloride, and polyvinylpyrrolidone.

The term "thickening agent" (and equivalent terms such as "gelling agent" and "viscosity increasing agent") refers to substances used in the pharmaceutical preparation of oral soluble films, to improve the viscosity and consistency of the slurry before casting. Active ingredient content uniformity is often a requirement for dosage forms, particularly those containing low dose highly potent active ingredients. To uniquely meet this requirement, oral soluble film formulations can contain uniform dispersions of active ingredient throughout the whole manufacturing process. Examples of thickening agents for use in an OSF described herein include acacia, agar, alginic acid, calcium alginate, carboxymethylcellulose calcium, carboxymethylcellulose sodium, carrageenan, ceratonia, chitosan, cyclomethicone, ethylcellulose, gelatin, glycerin, guar gum, hydrogenated vegetable oil, hydroxyethy cellulose, hydroxypropyl cellulose, hydroxypropyl starch, hypromellose, locust bean gum, maltodextrin, methylcellulose, pectin, polydextrose, polyethylene glycol, polyvinyl alcohol, potassium chloride, potassium alginate, povidone, propylene glycol alginate, sodium alginate, sodium chloride, starch, sucrose, sulfobutylether β-cyclodextrin, and xanthan gum.

The term "lubricant" (and equivalent terms such as "glidant") refers to a substance used in the pharmaceutical preparation of oral solid dosage forms (e.g., oral soluble film) to improve processing characteristics. For example, the lubricant can enhance flow of the slurry by reducing interparticulate friction. The lubricant is typically added to a powder to improve its flowability. A lubricant will typically only work at a certain range of concentrations. Above a certain concentration, the lubricant will function to inhibit flowability. Examples of lubricants for use in an OSF described herein include ascorbyl palmitate, calcium palmitate, castor oil, fumed silica (colloidal silicon dioxide), glycerin monostearate, glyceryl palmitostearate, hydrogenated castor oil, hydrogenated vegetable oil (e.g., Sterotex®, Lubritab®, and Cutina®), light mineral oil, magnesium stearate, medium-chain triglycerides, mineral oil, palmitic acid, partial fatty acid esters of sugars, polyethylene glycol fatty acid esters, polyethylene glycol fatty alcohol ethers, polyethylene glycol sorbitan fatty acid esters, 2-ethoxy ethanol, ethyl alcohol, poloxamer, polyethylene glycol, sodium benzoate, sodium chloride, starch, sucrose esters, and talc.

The term "adsorbent" refers to a substance used to prevent or mitigate the occurrence of another substance from undergoing sorption (process in which one substance takes up or holds another, by either absorption or adsorption). Typically, the adsorbent is used to prevent or mitigate another substance from taking up water or moisture. Examples of adsorbents for use in an OSF described herein include aluminum hydroxide, aluminum oxide, aluminum phosphate, attapulgite, bentonite, powdered cellulose, colloidal silicon dioxide, magnesium aluminum silicate, microcrystalline cellulose, pectin, polycarbophil, and talc.

The term "suspending agent" refers to a substance that helps another substance (e.g., active pharmaceutical ingredient) to stay suspended in the formulation (e.g., slurry) and to prevent or mitigate the occurrence of caking at the bottom of the container. One of the properties of a well-formulated suspension is that it can be easily re-suspended by the use of moderate agitation or blending. Typically, the suspending agent will help other substances to stay suspended in the slurry, prior to the curing. In doing so, the substances are held in the slurry by the suspending agent, and do not settle at the bottom to any appreciable degree. Examples of suspending agents for use in an OSF described herein include acacia, agar, alginic acid, bentonite, calcium stearate, carbomers, carboxymethylcellulose calcium, carboxymethylcellulose sodium, carrageenan, powdered cellulose, cellulose (microcrystalline and carboxymethylcellulose sodium), colloidal silicon dioxide, dextrin, gelatin, guar gum, hydroxyethyl cellulose, hydroxypropyl cellulose, hypromellose, kaolin, magnesium aluminum silicate, maltitol solution, medium-chain triglycerides, methylcellulose, microcrystalline cellulose, phospholipids, polycarbophil, polyethylene glycol, polyoxyethylene sorbitan fatty acid esters, potassium alginate, povidone, propylene glycol alginate, sesame oil, sodium alginate, sodium starch glycolate, sorbitan esters, sucrose, tragacanth, vitamin E polyethylene glycol succinate, and xanthan gum.

The term "disintegrating agent" (and equivalent terms such as "disintegrator" and "disintegrant") refers to a substance used in the pharmaceutical preparation of oral solid dosage forms (e.g., oral soluble film or orally disintegrating tablet), that helps the dosage form to disintegrate and release the active ingredient on contact with moisture. The disintegrant is employed in the manufacture of an OSF to promote its rapid disintegration or break down into small particles after administration for facilitating rapid dissolution into bodily fluid. Examples of disintegrating agents for use in an OSF described herein include alginic acid, Amberlite™ calcium alginate, carboxymethylcellulose calcium, carboxymethylcellulose sodium, powdered cellulose, chitosan, colloidal silicon dioxide, corn starch and pregelatinized starch, croscarmellose sodium, crospovidone, glycine, guar gum, hydroxypropyl cellulose, microcrystalline cellulose, polacrilin potassium, povidone, sodium starch glycolate, pregelatinized starch, and low substituted HPMC.

The term "permeation enhancer" refers to a substance used in the pharmaceutical preparation of an oral soluble film, to increase the delivery of the active ingredient, when administered in vivo (e.g., orally), resulting in an increased absorption of the active ingredient. The active ingredient can be delivered across the desired body surface, e.g., oral mucosa, such as buccal, sublingual, mucosa, or gingival; or an intestinal surface. Examples of permeation enhancers for use in an OSF described herein include anionic surfactants (e.g., sodium lauryl sulfate, sodium laurate, Laureth-9, sodium dodecyl sulfate (SDS), dioctyl sodium sulfosuccinate), nonionic surfactants (polyoxyethylene-9-lauryl ethe (PLE), Tween® 80, nonylphenoxypolyoxyethylene (NP-POE), polysorbate, sodium glycocholate), cationic surfactants (e.g., cetylpyridinium chloride, chitosan, trimethyl chitosan, poly-L-arginine, L-lysine), fatty acids or derivatives thereof (e.g., oleic acid caprylic acid, mono(di)glycerides, lauric acid, linoleic acid, acylcholines, acylcarnitine, sodium caprate, and oleic acid), and polyols (e.g., propylene glycol, polyethylene glycol, glycerol, or propanediol).

The term "active pharmaceutical ingredient" or "API" (and equivalent terms such as "active ingredient," "medicant," "medicament," "bioactive," and "active") refers to the substance sildenafil (as the free base, or as a pharmaceutically acceptable salt thereof, e.g., sildenafil citrate). The active pharmaceutical ingredient is pharmacologically and biologically active.

The term "saliva stimulating agent" (and equivalent terms such as "salivary stimulant" and "acidulant") refers to a substance used to increase the production of saliva, thereby increasing salivary flow rate. Examples of saliva stimulating agents for use in an OSF described herein include organic acids (e.g., ascorbic acid, citric acid, fumaric acid, tartaric acid, and malic acid), parasympathomimetic drugs (e.g., choline esters such as pilocarpine hydrochloride and cholinesterase inhibitors), physostigmine, and other substances (e.g., xylitol, xylitol/sorbitol, and nicotinamide).

The term "release modifier" refers to a substance used to modify the release of the active ingredient from an oral solid dosage form (e.g., OSF) and/or is used to modify the absorption of the active ingredient when the oral solid dosage form is orally administered to the subject. The drug release can be contrasted to an immediate release (IR), and includes, e.g., an extended release (XR), sustained release (SR), or delayed release (DR).

The term "adjuvant" refers to a substance used to modify (e.g., increase) the effect or efficacy of the active ingredient present in an oral solid dosage form (e.g., OSF). The adjuvant can be, e.g., a pharmacological agent or immunological agent.

The term "fragrance" (and equivalent terms such as "fragrant," "odorant," or "aroma compound") refers to a substance used to impart a desired smell, scent, or odor to a formulation (e.g., slurry or OSF).

The term "surfactant" refers to a substance used to lower the surface tension (or interfacial tension) between two liquids, between a gas and a liquid, or between a liquid and a solid. Surfactants may act as detergents, wetting agents, emulsifiers, foaming agents, or dispersants. The surfactant can be anionic, cationic, zwitterionic, or non-ionic.

The term "pH adjusting agent" refers to a substance used to change the pH of an aqueous solution (e.g., slurry). For example, the pH adjusting agent can be an acid, such that when added to an aqueous solution (e.g., slurry), it will decrease the pH. Alternatively, the pH adjusting agent can be a base, such that when added to an aqueous solution (e.g., slurry), it will increase the pH. The base can be an organic base (e.g., sodium bicarbonate), an inorganic base (e.g., sodium hydroxide), or combination thereof. Likewise, the acid can be an inorganic acid (e.g., hydrochloric acid), an organic acid (e.g., citric acid, malic acid, tartaric acid, etc.), or a combination thereof.

The term "buffering agent" refers to a weak acid or weak base used to maintain the pH (e.g., acidity or basicity) of a solution (e.g., slurry) near a chosen value after the addition of another acid or base. That is, the function of a buffering agent is to prevent or mitigate the occurrence of a rapid change in pH when acids or bases are added to the solution (e.g., slurry). Buffering agents have variable properties—some are more soluble than others; some are acidic while others are basic. The acid can be an organic acid, mineral acid, or combination thereof. Likewise, the base can be an organic base, inorganic base, or combination thereof.

The term "stabilizer" refers to a substance used to prevent or mitigate the occurrence of degradation of any one of more substances present in a formulation (e.g., the slurry and/or oral soluble film). This would include preventing or mitigating degradation of the active ingredient, as well as any of the inactive ingredients or excipients.

The term "antioxidant" refers to a substance used to inhibit, prevent, or mitigate the occurrence of oxidation of any one of more substances present in a formulation (e.g., the slurry and/or oral soluble film). This would include inhibiting, preventing, or mitigating oxidation of the active ingredient, as well as any of the inactive ingredients or excipients. Examples of antioxidants for use in an OSF described herein include ascorbic acid (vitamin C), vitamin A, α-tocopherol (vitamin E), beta-carotene, glutathione, ubiquinol (coenzyme Q), and selenium.

The term "microcrystalline" refers to a crystallized substance containing small crystals, wherein the crystalline lattice is visible only through microscopic examination.

"Microcrystalline cellulose" or "MCC" is a term used for refined wood pulp. A naturally occurring polymer, it is composed of glucose units connected by a 1-4 beta glycosidic bond. These linear cellulose chains are bundled together as microfibril spiraled together in the walls of plant cell. The term "silicified microcrystalline cellulose" refers to MCC which is silicified. Silicification is the process in which organic matter becomes saturated with silica. When present in the oral soluble film described herein, the microcrystalline cellulose can function as a filler. The microcrystalline cellulose can optionally further function as an anti-caking agent, emulsifier, bulking agent, viscosity increasing agent, binder, or any combination thereof.

The term "glycerin" refers to the substance having the IUPAC name propane-1,2,3-triol; CAS Number 56-81-5, 8043-29-6, 25618-55-7, 8013-25-0; chemical formula $C_3H_8O_3$ or $CH_2OH-CHOH-CH_2OH$; and molar mass 92.09 g/mol. The glycerin can be glycerin, 99% natural. The "99%" is a designation of purity and the "natural" is a designation that the substance is not synthetically prepared. When present in an oral soluble film described herein, the glycerin can function as a plasticizer. The glycerin can optionally further function as a sweetener, humectant, solvent, thickening agent, lubricant, or any combination thereof.

The term "copolymer" refers to a polymer derived from more than one species of monomer. The polymerization of monomers into copolymers is called copolymerization. Copolymers obtained by copolymerization of two monomer species are sometimes called bipolymers. Since a copolymer consists of at least two types of constituent units (also structural units), copolymers can be classified based on how these units are arranged along the chain. Linear copolymers consist of a single main chain, and include alternating copolymers, statistical copolymers, and block copolymers. Branched copolymers consist of a single main chain with one or more polymeric side chains, and can be grafted, star shaped or have other architectures. Graft copolymers are a special type of branched copolymer in which the side chains are structurally distinct from the main chain. Typically, the main chain is formed from one type of monomer (A) and branches are formed from another monomer (B), or else the side-chains have constitutional or configurational features that differ from those in the main chain. The individual chains of a graft copolymer may be homopolymers or copolymers. In specific embodiments, the copolymer can be a graft copolymer. In further specific embodiments, the graft copolymer can be polyvinyl alcohol (PVA)-polyethylene glycol (PEG) graft copolymer. Polyvinyl alcohol (PVA)-polyethylene glycol (PEG) graft copolymer is present in the product Kollicoat® Protect.

The term "polyvinyl alcohol" or "PVA" refers to a water-soluble synthetic polymer. It has the chemical formula $(C_2H_4O)_x$, idealized formula $[CH_2CH(OH)]_n$, and CAS No. 9002-89-5. PVA is present in the product Kollicoat® Protect.

The term "polyethylene glycol" or "PEG" refers to a polyether compound. PEG is also known as polyethylene oxide (PEO) or polyoxyethylene (POE), depending on its molecular weight. The structure of PEG is commonly expressed as $H-(O-CH_2-CH_2)_n-OH$. PEG has the CAS No. 25322-68-3.

The term "silicon dioxide" (and equivalent terms such as "silica") refers to an oxide of silicon with the chemical formula $SiO_2$, molar mass 60.08 g/mol, and CAS No. 7631-86-9. Silicon dioxide is present in the product Kollicoat® Protect.

The term "Kollicoat® Protect" refers to the commercial product containing (i) polyvinyl alcohol (PVA), (ii) polyvinyl alcohol (PVA)-polyethylene glycol (PEG) graft copolymer, and (iii) silicon dioxide. Kollicoat® Protect is a combination of water-soluble Kollicoat® IR and polyvinyl alcohol, wherein the Kollicoat® IR is a polyvinyl alcohol (PVA)-polyethylene glycol (PEG) graft copolymer. The PEG portion of Kollicoat® IR is PEG 6000. The Kollicoat® products are commercially available from BASF (Florham Park, N.J.). Kollicoat® Protect has the chemical name polyvinyl alcohol-polyethylene glycol copolymer and polyvinyl alcohol (PVA). Kollicoat® Protect has the CAS-Nos: Kollicoat® IR 96734-39-3, Polyvinyl alcohol 9002-89-5, and silicon dioxide 7631-86-9. When present in the oral soluble film described herein, the Kollicoat® Protect can function as a binder (e.g., rapidly dissolving binder). The Kollicoat® Protect can optionally further function as a film-coating agent, disintegrating agent, taste masking agent, emulsifier, to increase tensile strength of the OSF and/or elongation, anti-caking agent, or any combination thereof.

The term "peppermint" (and equivalent terms such as "Mentha balsamea Wild" and "Mentha×piperita") refers to a hybrid mint, a cross between watermint and spearmint. Peppermint has a relatively high menthol content. The oil also contains menthone and carboxyl esters, particularly menthyl acetate. Dried peppermint typically has 0.3-0.4 wt. % of volatile oil containing menthol (7-48 wt. %), menthone (20-46 wt. %), menthyl acetate (3-10 wt. %), menthofuran (1-17 wt. %) and 1,8-cineol (3-6 wt. %). Peppermint oil can contain small amounts of many additional compounds including limonene, pulegone, caryophyllene and pinene. Peppermint can also contain terpenoids and flavonoids, such as eriocarpin, hesperidin, and kaempferol 7-O-rutinoside. The peppermint can be available as dried peppermint (e.g., spray dried peppermint powder) or as a liquid (e.g., peppermint oil). When present as a spray dried powder, the peppermint can include a combination of peppermint oil and carrier (e.g., 25 wt. % peppermint oil and 75 wt. % carrier). The peppermint can include, e.g., the product Natural Peppermint Flavor, which is commercially available as Product No. 501500 TPK0504 from Firmenich Inc. (Anaheim, Calif.); the product Natural Peppermint Oil, commercially available from A. M. Todd; or the product Natural and Artificial Peppermint, commercially available from Firmenich (Anaheim, Calif.). When present in the oral soluble film described herein, the peppermint can function as a flavoring agent. The peppermint can optionally further function as a taste masking agent, permeation enhancer, or a combination thereof.

The term "sildenafil" refers to the compound having the name 5-{2-Ethoxy-5-[(4-methylpiperazin-1-yl)sulfonyl]phenyl}-1-methyl-3-propyl-1,6-dihydro-7H-pyrazolo[4,3-d]pyrimidin-7-one; CAS No. 139755-83-2, molecular formula $C_{22}H_{30}N_6O_4S$, and molar mass 474.5764 g/mol. The structural formula is provided below.

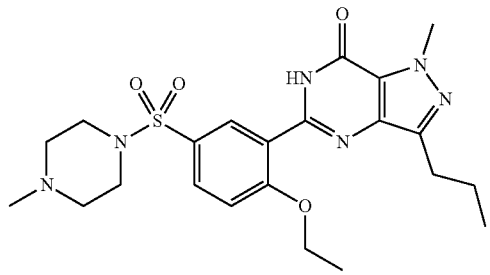 [SMILES: CCCc1nn(C)c2c(=O)[nH]c(-c3cc(S(=O)(=O)N4CCN(C)CC4)ccc3OCC)nc12]

Sildenafil is described in standard references such as, e.g., The Physician's Desk Reference, 2018 Edition; The Merck Index, 15th Edition (2013); and United States Pharmacopeia (USP) (2018). Together with a pharmaceutically acceptable counter-ion, sildenafil is also available as a pharmaceutically acceptable salt, e.g., the citrate salt (CAS No. 171599-83-0, molecular formula $.C_6H_8O_7$). The sildenafil citrate present in the oral soluble film described herein functions as an active ingredient (e.g., the sole active ingredient). In specific embodiments, the oral soluble film (drug product) can be manufactured from sildenafil citrate (drug substance) having a desired bulk density and/or particle size distribution (PSD). In specific embodiments, the oral soluble film (drug product) can be manufactured from sildenafil citrate (drug substance) having a desired physical form (e.g., amorphous, or crystalline), hydrate, or solvate thereof. Sildenafil citrate is commercially available from, e.g., MSN Organics Private Ltd. (Telangana, India); Amoli Organics Pvt. Ltd. (Milan, Italy); Azico Biophore India Pvt. Ltd. (Hyderabad, India); Raks Pharma Pvt. Ltd. (Andhra Pradesh, India); and SMS Pharmaceuticals Ltd. (Hyderabad, India).

The term "sodium benzoate" refers to the substance which has the chemical formula $C_6H_5COONa$; CAS No. 532-32-1; and molar mass 144.105 g/mol. When present in the oral soluble film described herein, the sodium benzoate can function as a preservative.

The term "FD&C Blue 1" refers to a synthetic organic compound used primarily as a blue colorant for processed foods, medications, dietary supplements, and cosmetics. It has the IUPAC name disodium; 2-[[4-[ethyl-[(3-sulfonatophenyl)methyl]amino]phenyl]-[4-[ethyl-[(3-sulfonatophenyl)methyl]azaniumylidene]cyclohexa-2,5-dien-1-ylidene]methyl]benzenesulfonate. It is classified as a triarylmethane dye and is known under various names, such as FD&C Blue No. 1 or Acid Blue 9. It is denoted by E number E133 and has a color index of 42090. It has the appearance of a blue powder and is soluble in water and glycerol, with a maximum absorption at about 628 nanometers. It is one of the oldest FDA-approved color additives and is generally considered nontoxic and safe. When present in the oral soluble film described herein, the FD&C Blue 1 can function as a colorant.

The term "acesulfame potassium" or "ACE-K" refers to a calorie-free sugar substitute (artificial sweetener) having the IUPAC name potassium 6-methyl-2,2-dioxo-2H-1,2$\lambda^6$,3-oxathiazin-4-olate. In the European Union, it is known under the E number (additive code) E950. In chemical structure, acesulfame potassium is the potassium salt of 6-methyl-1,2,3-oxathiazine-4(3H)-one 2,2-dioxide. It is a white crystalline powder with molecular formula $C_4H_4KNO_4S$ and a molecular weight of 201.24 g/mol. When present in the oral soluble film described herein, the ACE-K can function as a sweetener.

The term "sucralose" refers to an artificial sweetener and sugar substitute. In the European Union, it is also known under the E number E955. Sucralose has the IUPAC name 1,6-dichloro-1,6-dideoxy-β-D-fructofuranosyl-4-chloro-4-deoxy-α-D-galactopyranoside; CAS No. 56038-13-2; chemical formula $C_{12}H_{19}C_{13}O_8$; and molar mass 397.64 g/mol. When present in the oral soluble film described herein, the sucralose can function as a sweetener.

The term "oral soluble film" or "OSF" (and the equivalent terms such as "soluble film," "orodispersible film," "oral thin film," "OTF," "oral film," "edible film," "mucoadhesive film," "mucoadhesive oral film," "MOF," "oral disintegrating film," "oral dissolvable film," "ODF," etc.) refers to a soluble film specifically configured for oral administration. The term also includes "buccal film" (oral soluble film intended to be placed in the buccal space) and "sublingual film" (oral soluble film intended to be placed under the tongue). The oral soluble film is self-supporting, or in other words, is able to maintain its integrity and structure in the absence of a separate support. Oral soluble films are composed of pharmaceutically acceptable ingredients that are edible or ingestible. The oral soluble film can be configured for multi- or unidirectional release. OSFs can be similar in size and shape to a postage stamp, and are designed for oral administration, with the user placing the strip on the tongue (enteric), under the tongue (sublingual), through the oral mucosa (mucosal), against the inside of the cheek (buccal), or on the gums (gingival). Aside from the enteric route, these drug delivery options allow the medication to bypass the first pass metabolism thereby making the medication more bioavailable. As the film dissolves, the drug can enter the blood stream enterically, mucosally, buccally, gingivally, and/or sublingually. As such, the oral soluble film is prepared using hydrophilic polymers that can dissolve on the tongue or buccal cavity, delivering the drug to the systemic circulation via dissolution when contact with liquid is made. Oral film drug delivery accordingly uses a dissolving film to administer drugs via absorption in the mouth (buccally, sublingually, or gingivally) and/or via the small intestines (enterically). Especially for drugs which are metabolized extensively by the first-pass effect, oral films described herein can provide a faster-acting and better absorption profile. The oral soluble film can be shaped as being circular, round, oval, elliptical, or polygonal (e.g., triangular, square, or rectangular). Additionally, the OSF can optionally include a logo and/or indicia located thereon. The logo and/or indicia can identify, e.g., the marketing company name, manufacturing company name, drug substance name, drug product name, strength, dosage form, route of administration, and/or product serialization. Such logo and/or indicia can be printed thereon, e.g., with pharmaceutically acceptable ink, or can be embossed.

The term "anhydrous film" refers to an oral soluble film containing no significant or appreciable amount of water. As such, reference to the weight percentage amount of water (moisture) present in an anhydrous film is essentially zero. Within the context of the present invention, it is appreciated that those of skill in the art understand and agree that an oral soluble film will likely include at least trace amounts of water—as the complete removal of the water during the curing phase is unlikely. And that the oral soluble film may pick up moisture during the packaging, shipment, and/or storage. However, with the exception of the solvent water, substances (e.g., excipients and API) present in the orally soluble film described herein can be characterized by the weight percentage amount, based on an anhydrous film. As such, within the context of the present invention, it is appreciated that those of skill in the art understand and agree that reference to the oral soluble film as being anhydrous, at least for purposes of expressing the weight percentage amount of the excipients and/or API (with the notable exception of the solvent water) is otherwise acceptable and appropriate.

The term "hydrated film" refers to an oral soluble film containing a significant and appreciable amount of water. The amount of water present in a hydrated film can be measured (e.g., loss on drying).

The term "unit dosage" (and equivalent terms such as "unit dose" and "unit dosage form") refers to an oral soluble film sized to the appropriate dimension, such that the individual film contains a desired amount of active ingredient to be administered to a subject for an intended use. Prior to sizing to the appropriate dimension (thereby providing the unit dosage form), the soluble film can exist, e.g., in either the unwound form (e.g., sheet) or in the wound form (e.g., bulk roll).

The term "drug substance" refers to the unformulated API (active pharmaceutical ingredient). The API has the therapeutic effect in the body as opposed to the excipients, which assist with the delivery of the API. The chemical purity and physical state (crystal form, salt form, etc.) can influence the quality and performance of a drug substance. This is especially important for water insoluble drugs.

The term "drug product" refers to the formulated drug substance with excipients. The drug product is typically the final marketed dosage form of the drug substance, for example a tablet, capsule, or oral soluble film (OSF). A drug substance, because of multiple factors (sensitivity, stability, etc.) is often mixed with other components before being released for use in the market. The drug substance together with the added ingredients (excipients) is known as drug product. The drug substance together with these added agents is called the drug product and within its packaging is called the "finished product."

The term "drug load" (and equivalent terms such as "load of active ingredient") refers to the amount of active pharmaceutical ingredient present in the oral soluble film. For example, in specific embodiments the oral soluble film can have a high drug load, such that the active pharmaceutical ingredient is present in a relatively high amount (e.g., above 30 wt. %) of the oral soluble film. The drug load is expressed as $$\frac{\text{weight of } API}{\text{weight of } OSF}.$$

The term "binder load" (and equivalent terms such as "load of binder") refers to the amount of binder (e.g., Kollicoat® Protect and MCC) present in the oral soluble film. In specific embodiments, the oral soluble film can have a high binder load, such that the binders are present, in the aggregate, in a relatively high amount (e.g., at least 25 wt. % of the oral soluble film). In further specific embodiments, the oral soluble film can have a high binder load, such that the Kollicoat® binders are present, in the aggregate, in a relatively high amount (e.g., at least 30 wt. % of the oral soluble film).

The term "weight ratio" refers to the weight ratio of two items. For example, the weight ratio of binder to API can be expressed as $$\frac{\text{weight of binder}}{\text{weight of } API}.$$

In specific embodiments, the weight ratio of binder to API is 83±10%. In further specific embodiments, the weight ratio of binder to API is 83±5%.

The term "CL/F" refers to the apparent total clearance of drug from plasma after oral administration. It is measured in units of volume/time (mL/min) or in units of volume/time/kg (mL/min/kg).

The term "$T_{max}$" refers to time of maximum plasma concentration and is the time to reach maximum (peak) plasma concentration following drug administration. It is measured in units of time (hours).

The term "$t_{1/2}$" refers to elimination half-life and is time to reach elimination half-life (to be used in one or non-compartmental model). It is measured in units of time (hours).

The term "treating" (and equivalent terms such as "treat," "treated," and "treatment") of a subject includes the administration of an active pharmaceutical ingredient (API), or a unit dosage form containing the same (e.g., oral soluble film), to a subject with the purpose of preventing, mitigating, curing, healing, alleviating, relieving, altering, remedying, ameliorating, improving, stabilizing or affecting a disease or disorder, or a symptom of the disease or disorder. The disease or disorder can be, e.g., erectile dysfunction (ED), antidepressant-induced erectile dysfunction (ED), or pulmonary arterial hypertension (PAH).

The term "erectile dysfunction" or "ED" (and the equivalent term "impotence") refers to the type of sexual dysfunction in which the penis fails to become or stay erect during sexual activity. It is the most common sexual problem in men. Through its connection to self-image and to problems in sexual relationships, erectile dysfunction can cause psychological harm. ED is characterized by the regular or repeated inability to achieve or maintain an erection of sufficient rigidity to accomplish sexual activity. ED often has an impact on the emotional well-being of both men and their partner(s). Many men do not seek treatment due to feelings of embarrassment. It is believed that about 75% of diagnosed cases of ED go untreated.

The term "kit" refers to a system for delivering an oral soluble film as described herein, from one location to another. Such delivery systems can include enclosures that allow for the storage, transport, and/or delivery of an oral soluble film as described herein and any accompanying materials. The enclosure can be, e.g., a box or a bag. The accompanying materials can include, e.g., label, reference material, prescribing information, supporting material, or a combination thereof. For example, the kit can include a single dose of the oral soluble film described herein, that is individually packaged and sealed with a primary packaging material. Alternatively, the kit can include multiple doses of the oral soluble film described herein, each of which is individually packaged and sealed with a primary packaging material. Additionally, the kit can include an enclosure containing (i) multiple doses of the oral soluble film described herein, each individually packaged and sealed with a primary packaging material, and (ii) prescribing information. The primary packaging material can include at least one of metalized polyester, cellophane, polypropylene, nylon, polyester, vinylidene chloride, vinyl chloride, polycarbonate, low-density polyethylene, high-density polyethylene, linear low-density polyethylene, ionomer, polyvinyl alcohol, ethylene/vinyl acetate copolymer, ethylene/acrylic acid copolymer, ethylene/ethyl acrylate copolymer, polystyrene, and aluminum foil. The primary packaging material can include a single layer of material, or can include multiple layers of material (wherein each layer can independently include the same or different material as the other layers). The primary packaging material forms a primary package that can (i) protect the oral soluble film from light, (ii) protect the oral soluble film from microbial contamination, (iii) be child resistant, (iv) be a barrier to moisture and vapor, (v) mitigate leachable into the oral soluble film, (vi) identifies a logo and/or includes printed indicia, or (vii) any combination thereof. The logo and/or printed indicia can identify, e.g., the marketing company name, manufacturing company name, drug substance name, drug product name, strength, dosage form, route of administration, and/or product serialization.

The term "prescribing information" (and the equivalent terms "product information," "product labeling," "package insert," or "PI") refers to information relevant to the drug product, that is generally drafted by the drug company and such information is approved by the FDA. It includes the details and directions healthcare providers need to prescribe the drug product properly. It is also the basis for how the drug company can advertise its drug product. The prescribing information includes such details about the drug product as: its chemical description; how it works; how it interacts with other drugs, supplements, foods, and beverages; what condition(s) or disease(s) it treats; who should not use the drug product; serious side effects, even if they occur rarely; commonly occurring side effects, even if they are not serious; and effects on specific groups of patients, such as children, pregnant women, or older adults and how to use it in these populations. Sometimes, the drug company drafts prescription drug information designed for patients that the FDA approves. These are often called "Patient Package Inserts," "Patient Product Information," or "PPIs."

The term "drug company" refers to the one or more companies that (i) markets the drug product (or retains ownership rights to the same), (ii) manufactures the drug product (or retains ownership rights to the same), and/or (iii) is the NDA applicant holder. As such, the drug company can be a single company or can include separate, multiple companies.

The term "subject" refers to living organisms such as humans, dogs, cats, and other mammals. Administration of the active ingredient included in the oral soluble film described herein can be carried out at dosages and for periods of time effective for the treatment of the subject. In some embodiments, the subject is a human. Within the context of treating PAH, the human subject can be a male or female, and can further be an adult, adolescent, child, toddler, or infant. Within the context of treating ED, the human subject can be a post-pubescent male, typically at least 18 years old.

The term "transmucosal" refers to any route of administration via a mucosal membrane or mucosal surface. Examples include, but are not limited to, buccal, sublingual, nasal, vaginal, and rectal.

The term "buccal administration" refers to a topical route of administration by which a drug held or applied in the buccal area (in the cheek) diffuses through the oral mucosa (tissues which line the mouth) and enters directly into the bloodstream. Buccal administration may provide better bioavailability of some drugs and a more rapid onset of action compared to oral administration because the medication does not pass through the digestive system and thereby avoids first pass metabolism. In multiple instances, buccal administration has been found to avoid liver and GI toxicities.

The term "buccal space" (also termed the buccinator space) refers to a fascial space of the head and neck (sometimes also termed fascial tissue spaces or tissue spaces). It is a potential space in the cheek, and is paired on each side. The buccal space is superficial to the buccinator muscle and deep to the platysma muscle and the skin. The buccal space is part of the subcutaneous space, which is continuous from head to toe.

The term "oral mucosa" refers to the mucous membrane lining the inside of the mouth and consists of stratified squamous epithelium termed oral epithelium and an underlying connective tissue termed lamina propria. Oral mucosa can be divided into three main categories based on function and histology: (1) Masticatory mucosa, keratinized stratified squamous epithelium, found on the dorsum of the tongue, hard palate and attached gingiva; (2) Lining mucosa, nonkeratinized stratified squamous epithelium, found almost everywhere else in the oral cavity, including the: (a) Buccal mucosa refers to the inside lining of the cheeks and floor of the mouth and is part of the lining mucosa; (b) Labial mucosa refers to the inside lining of the lips and is part of the lining mucosa; and (c) Alveolar mucosa refers to the lining between the buccal and labial mucosae. It is a brighter red, smooth and shiny with many blood vessels, and is not connected to underlying tissue by rete pegs; and (3) Specialized mucosa, specifically in the regions of the taste buds on lingual papillae on the dorsal surface of the tongue that contains nerve endings for general sensory reception and taste perception.

The term "sublingual administration," from the Latin for "under the tongue," refers to the pharmacological route of administration by which substances diffuse into the blood through tissues under the tongue. When a drug comes in contact with the mucous membrane beneath the tongue, it is absorbed. Because the connective tissue beneath the epithelium contains a profusion of capillaries, the substance then diffuses into them and enters the venous circulation. In contrast, substances absorbed in the intestines are subject to first-pass metabolism in the liver before entering the general circulation. Sublingual administration has certain advantages over oral administration. Being more direct, it is often faster, and it ensures that the substance will risk degradation only by salivary enzymes before entering the bloodstream, whereas orally administered drugs must survive passage through the hostile environment of the gastrointestinal tract, which risks degrading them, by either stomach acid or bile, or by enzymes such as monoamine oxidase (MAO). Furthermore, after absorption from the gastrointestinal tract, such drugs must pass to the liver, where they may be extensively altered; this is known as the first pass effect of drug metabolism. Due to the digestive activity of the stomach and intestines, the oral route is unsuitable for certain substances.

The term "gingival administration" refers to the pharmacological route of administration by which substances diffuse into the blood through tissues in the gums. The gums or gingiva (plural: gingivae), consist of the mucosal tissue that lies over the mandible and maxilla inside the mouth.

The term "enteral administration" refers to a drug administration via the human gastrointestinal tract. Enteral administration involves the esophagus, stomach, and small and large intestines (i.e., the gastrointestinal tract). Methods of administration include oral and rectal. Enteral administration may be divided into three different categories, depending on the entrance point into the GI tract: oral (by mouth), gastric (through the stomach), and rectal (from the rectum). (Gastric introduction involves the use of a tube through the nasal passage (NG tube) or a tube in the belly leading directly to the stomach (PEG tube). Rectal administration usually involves rectal suppositories.) Enteral medications come in various forms, including, e.g., tablets to swallow, chew or dissolve in water; capsules and chewable capsules (with a coating that dissolves in the stomach or bowel to release the medication there), oral soluble films, time-release or sustained-release tablets and capsules (which release the medication gradually), osmotic delivery systems, powders or granules, and liquid medications or syrups.

The term "oral administration" or "PO" refers to a route of administration where a substance is taken through the mouth. Many medications are taken orally because they are intended to have a systemic effect, reaching different parts of the body via the bloodstream.

The term "moisture content" (and equivalent terms such as "water content") refers to the quantity of water contained in an oral soluble film described herein. The moisture content can encompass bound water and unbound water. Water content is expressed as a ratio, which can range from 0 (completely dry) to the value of the soluble film's porosity at saturation. It can be given on a volumetric or mass (gravimetric) basis. Typically, the moisture content will be expressed as a weight percent (e.g., 4 wt. %). Water content can be directly measured using a drying oven. Other methods that determine water content of a sample include chemical titrations (for example the Karl Fischer titration), determining mass loss on heating (perhaps in the presence of an inert gas), or after freeze drying. The Dean-Stark method is also commonly used. Unless specified otherwise, the loss on drying (LOD) method can be employed to calculate the moisture content of a soluble film described herein.

The term "loss on drying" or "LOD" refers to the loss of weight expressed as percentage w/w resulting from water and/or volatile matter that can be driven off under specified conditions from an object (e.g., oral soluble film). In this technique, a sample of material (e.g., oral soluble film) is weighed, heated in an oven for an appropriate period, cooled in the dry atmosphere of a desiccator, and then reweighed. The difference in weight is the loss on drying (LOD). For example, the oral soluble film can have a loss on drying (LOD) of 5±2 wt. %. Methods employed include Thermogravimetric Analysis (TGA) and IR Moisture Analyzers.

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "disintegration" refers to a physical process of breaking down a substance into fragments to improve its solubility in a solvent. The process is used predominantly in pharmaceutical and chemical industries. Disintegration occurs when a dosage form breaks up into smaller particles. It usually takes place in two steps; the content breaks up into small granules which then disaggregate. For oral soluble films, this breaking up process of the dosage form usually starts in the oral cavity, where it may be completed depending upon, e.g., the formulation, contact duration, volume of saliva, and whether or not taken with a beverage. If the dosage form passes into the stomach and then into the small intestine, then the process may continue there. Disintegration can usually be observed in the laboratory in a dissolution apparatus. Actual QC disintegration methods, however, use specific pieces of equipment described in USP <701>.

The term "dissolution" refers to a process through which solutes dissolve in a solvent. Dissolution is used predominantly in pharmaceutical industries to check how soluble a drug is in the body. Dissolution is a process through which a dosage form dissolves in a solvent to produce a solution. Dissolution requires disintegration of the dosage form to occur first, then drug particles to dissolve. It is the rate (amount of drug and time) at which the drug dissolves. In vivo dissolution of an oral soluble film starts as soon as the drug in the dosage form is wetted with saliva. There are many different dissolution apparatuses used to establish how much drug dissolves and how long this takes. The standard apparatus is also described in USP <711>.

The term "bioavailability" refers to a subcategory of absorption and is the fraction (%) of an administered drug that reaches the systemic circulation. Mathematically, bioavailability equals the ratio of comparing the area under the plasma drug concentration curve versus time (AUC) for the extravascular formulation to the AUC for the intravascular formulation. AUC can be utilized because AUC is proportional to the dose that has entered the systemic circulation.

The term "pharmacokinetics," sometimes abbreviated as "PK" refers to a branch of pharmacology dedicated to determining the fate of substances administered to a living organism. It attempts to analyze chemical metabolism and to discover the fate of a chemical from the moment that it is administered up to the point at which it is completely eliminated from the body. Pharmacokinetics is the study of how an organism affects a drug, whereas pharmacodynamics (PD) is the study of how the drug affects the organism. Both together influence dosing, benefit, and adverse effects, as seen in PK/PD models.

PK therefore refers to the study of the uptake of drugs by the body, the biotransformation they undergo, the distribution of the drugs and their metabolites in the tissues, and the elimination of the drugs and their metabolites from the body over a period of time.

The following are commonly measured pharmacokinetic metrics:

| Pharmacokinetic metrics | |
| --- | --- |
| Characteristic | Description |
| Dose | Amount of drug administered. |
| Dosing interval | Time between drug dose administrations. |
| $C_{max}$ | The peak plasma concentration of a drug after administration. |
| $T_{max}$ | Time to reach $C_{max}$. |
| $C_{min}$ | The lowest (trough) concentration that a drug reaches before the next dose is administered. |
| Volume of distribution | The apparent volume in which a drug is distributed (i.e., the parameter relating drug concentration in plasma to drug amount in the body). |
| Concentration | Amount of drug in a given volume of plasma. |
| Absorption half life | The time required for the concentration of the drug to double its original value for oral and other extravascular routes. |
| Absorption rate constant | The rate at which a drug enters into the body for oral and other extravascular routes. |
| Elimination half-life | The time required for the concentration of the drug to reach half of its original value. |
| Elimination rate constant ($K_{EL}$) | The rate at which a drug is removed from the body. |
| Infusion rate | Rate of infusion required to balance elimination. |
| Area under the curve | The integral of the concentration-time curve (after a single dose or in steady state). |
| Clearance | The volume of plasma cleared of the drug per unit time. |
| Bioavailability | The systemically available fraction of a drug. |
| Fluctuation | Peak trough fluctuation within one dosing interval at steady state. |

The term "curing" refers to a chemical process that can be used to produce a soluble film (as described herein) from a slurry (also described herein). The process can be carried out by removing solvent (water), by toughening or hardening of polymer material present in the slurry, by cross-linking the polymer chains, etc. The term curing can be used to refer to the processes where starting from a liquid or semi-solid solution (e.g., slurry), a solid product (e.g., soluble film) is obtained. Curing can be initiated by heat, radiation, electron beams, or chemical additives. To quote from IUPAC: curing "might or might not require mixing with a chemical curing agent." IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook. Thus, two broad classes are (i) curing induced by chemical additives (also called curing agents, hardeners) and (ii) curing in the absence of additives. An intermediate case involves a mixture of resin and additives that requires external stimulus (light, heat, radiation) to induce curing.

The term "mass" refers to a measurement of how much matter is in an object. Mass is a combination of the total number of atoms, the density of the atoms, and the type of atoms in an object. Mass is usually measured in grams (which is abbreviated as g) or milligrams (which is abbreviated as mg).

The term "density" refers to the mass per unit volume of an object (e.g., oral soluble film). Density is calculated by dividing the mass of an object by the volume of the object. The volume of an object can be stated as cubic centimeters or milliliters as both are equivalent.

The term "tack" refers to the tenacity with which the oral soluble film adheres to an accessory (a piece of paper) that has been pressed into contact with the film.

The term "tensile strength" refers to the maximum stress applied to a point at which the oral soluble film specimen breaks. It is calculated by the applied load at rupture divided by the cross-sectional area of oral soluble film, as given in the equation below:

Tensile strength=Load at failure×100/Film thickness×Film width

The term "percent elongation" refers to the relative increase in amount in length upon application of stress. When stress is applied on a film sample, it gets stretched. This is referred to as strain. Strain is basically the deformation of film before it gets broken due to stress. It can be measured by using hounsfield universal testing machine. Generally, elongation of the film increases as the plasticizer content increases. It is calculated by the formula:

% Elongation=Increase in length of film×100/Initial length of film

The term "tear resistance" refers to the resistance which a film offers when some load or force is applied on the film specimen. Specifically, it is the maximum force required to tear the specimen. The load mainly applied can be of a very low rate (e.g., 51 mm/min). The unit of tear resistance is Newton or pounds-force.

The term "Young's modulus" (and equivalent terms such as "elastic modulus") refers to the measure of stiffness of a soluble film. It is represented as the ratio of applied stress over strain in the region of elastic deformation as follows:

Young's modulus=Slope×100/Film thickness×Cross head speed

Hard and brittle strips demonstrate a high tensile strength and Young's modulus with small elongation.

The term "folding endurance" refers to number of times the film can be folded without breaking or without any visible crack. Folding endurance is a measure of the brittleness of a film. The method followed to determine endurance value is that the film specimen is repeatedly folded at the same place until it breaks, or a visible crack is observed. The number of times the film is folded without breaking or without any visible crack is the calculated folding endurance value.

The term "drug content uniformity" (and equivalent terms such as "uniformity of dosage unit" or "CU") refers to the degree of uniformity in the amount of drug substance among dosage units, and unless otherwise specified, is set forth in USP-NF General Chapter <905> Uniformity of Dosage Units.

Across multiple embodiments, substances present in the orally soluble film described herein are characterized by the weight percentage amount of substance present therein. The substance can be the active pharmaceutical ingredient and/or any one or more of the excipients. The weight percentage amount of substance present therein can be based on an anhydrous film (e.g., an orally soluble film containing no significant and appreciable amount of water). A notable exception is reference to the weight percentage amount of water (moisture) present in the soluble film. Specifically, because an anhydrous film contains no water, reference to the weight percentage amount of water (or moisture) contained within the oral soluble film can be based on a hydrated (e.g., 5±1.5 wt. % hydrated) oral soluble film. By way of illustration, reference is made to the product illustrated in the table below. In one embodiment, an oral soluble film can be prepared from a slurry, in which an active ingredient (sildenafil citrate) is present in 70.24 mg per 195.10 mg (36.00 wt. %) of an anhydrous oral soluble film. This can be calculated as follows:

$$\frac{\text{mass active ingedient (mg)}}{\text{mass dry weight film (mg)}} \times 100 =$$

$$\frac{70.24 \text{ mg}}{195.10 \text{ mg}} \times 100 = 0.3600 = 36.00 \text{ wt. \%}$$

The weight percentage amount of each excipient in the anhydrous oral soluble film can likewise be calculated. In order to arrive at these calculations, the water is not included in the mass of the oral soluble film.

In another embodiment, the active ingredient (sildenafil citrate) can be present in 16.8 wt. % of the slurry. In arriving at this calculation, the water is included in the mass of the slurry. The mass of the slurry (10,000 g) is obtained from the amount (mass) of all substances added to form the slurry, including the purified water added (5,328 g). This can be calculated as follows:

$$\frac{\text{mass active ingedient (g)}}{\text{mass of slurry (g)}} \times 100 = \frac{1,678.6 \text{ g}}{10,000 \text{ g}} \times 100 = 0.168 = 16.8 \text{ wt. \%}$$

Likewise, the active ingredient (sildenafil citrate) can be present in 70.24 mg per 204.86 mg (34.29 wt. %) of a hydrated oral soluble film. This can be calculated as follows:

$$\frac{\text{mass active ingedient (mg)}}{\text{mass 5\% hydrated film (mg)}} \times 100 =$$

$$\frac{70.24 \text{ mg}}{204.86 \text{ mg}} \times 100 = 0.3429 = 34.29 \text{ wt. \%}$$

The level of hydration of the hydrated film can be estimated (e.g., a 5% hydrated film). For that hydrated film, the requisite amount of water (e.g., 5 wt. %) is used to obtain the calculated amount of water (mg) in the hydrated film, as well as the calculated weight percentage amounts for each of the substances present in the hydrated film.

| | FORMULATION 1.01 | | | | | |
| --- | --- | --- | --- | --- | --- | --- |
| | | SLURRY | | ORAL SOLUBLE FILM | | |
| | | | | | Amount in | |
| Substance | Quantity dispensed (g) | Amount in slurry (wt. %) | Amount in anhydrous film (wt. %) | Amount in anhydrous film (mg) | 5% hydrated film (wt. %) | Amount in 5% hydrated film (mg) |
| Sildenafil Citrate | 1678.6 | 16.8 | 36.00 | 70.24 | 34.29 | 70.24 |
| Kollicoat ® Protect | 1406.3 | 14.1 | 30.00 | 58.53 | 28.57 | 58.53 |
| Microcrystalline | | | | | | |

-continued

FORMULATION 1.01

| | | | | ORAL SOLUBLE FILM | | |
|---|---|---|---|---|---|---|
| | | SLURRY | | Amount in | | |
| Substance | Quantity dispensed (g) | Amount in slurry (wt. %) | Amount in anhydrous film (wt. %) | Amount in anhydrous film (mg) | 5% hydrated film (wt. %) | Amount in 5% hydrated film (mg) |
| Cellulose - Avicel ® PH-101 | 252.1 | 2.5 | 5.45 | 10.63 | 5.19 | 10.63 |
| Natural Peppermint Flavor | 299.9 | 3.0 | 6.44 | 12.56 | 6.13 | 12.56 |
| Glycerin, 99.7% pure | 558.5 | 5.6 | 12.00 | 23.41 | 11.43 | 23.41 |
| Sucralose | 280.0 | 2.8 | 6.00 | 11.70 | 5.71 | 11.70 |
| Acesulfame Potassium | 186.0 | 1.86 | 4.00 | 7.80 | 3.80 | 7.80 |
| FD&C Blue 1 | 0.5 | 0.005 | 0.01 | 0.02 | 0.01 | 0.02 |
| Sodium Benzoate | 5.0 | 0.05 | 0.10 | 0.20 | 0.10 | 0.20 |
| Water | 5328 | 53.3 | NA | NA | 5.00 | 9.76 |
| TOTAL | 10000.0 | 100 | 100 | 195.10 | 100 | 204.86 |

The term "particle-size distribution" or "PSD" refers to a list of values or a mathematical function that defines the relative amount, typically by mass, of particles present according to size. For example, the mass-median-diameter (MMD) (expressed as, e.g., d10, d50, d90, etc.) refers to the log-normal distribution mass median diameter. The MMD is considered to be the average particle diameter by mass. The particle size distribution can be obtained by, e.g., laser diffraction, analytical sieving, light scattering, etc.

Particle size Distribution D10 (or d10) is also written as X10, D(0,1) or X(0,1). It represents the particle diameter corresponding to 10% cumulative (from 0 to 100%) undersize particle size distribution. In other words, if particle size D10 is 7.8 um, then 10% of the particles in the tested sample are smaller than 7.8 micrometer, or the percentage of particles smaller than 7.8 micrometer is 10%. D10 is a typical point in particle size distribution analysis. D10 is also divided into Dv10, Dw10 and Dn10. Dv10 means volume D10, whereas Dw10 is mass D10 and Dn10 is number D10.

Particle size Distribution D50 (or d50) is also written as X50, D(0,5) or X(0,5). It represents the particle diameter corresponding to 50% cumulative (from 0 to 100%) undersize particle size distribution. In other words, if particle size D50 is 7.8 um, then 50% of the particles in the tested sample are smaller than 7.8 micrometer, or the percentage of particles smaller than 7.8 micrometer is 50%. D50 is a typical point in particle size distribution analysis. D50 is also divided into Dv50, Dw50 and Dn50. Dv50 means volume D50, whereas Dw50 is mass D50 and Dn50 is number D50.

Particle size Distribution D90 (or d90) is also written as X90, D(0,9) or X(0,9). It represents the particle diameter corresponding to 90% cumulative (from 0 to 100%) undersize particle size distribution. In other words, if particle size D90 is 7.8 um, then 90% of the particles in the tested sample are smaller than 7.8 micrometer, or the percentage of particles smaller than 7.8 micrometer is 90%. D90 is a typical point in particle size distribution analysis. D90 is also divided into Dv90, Dw90 and Dn90. Dv90 means volume D90, whereas Dw90 is mass D90 and Dn90 is number D90.

Manufacturing, Packaging, and Distribution

The manufacture of oral soluble films can be carried out by various methods such as: (1) casting (e.g., solvent casting or semi-solid casting), (2) extrusion (e.g., hot melt extrusion or solid dispersion), and (3) rolling. These methods of manufacturing oral soluble films are generally well-known to the skilled artisans. See, e.g., "Manufacturing Techniques of Orally Dissolving Films," *Pharmaceutical Technology*, Volume 35, Issue 1 (Jan. 2, 2011); "Current Advances in Drug Delivery Through Fast Dissolving/Disintegrating Dosage Forms," Vikas Anand Saharan, pp. 318-356 (39) (2017); A short review on "A novel approach in oral fast dissolving drug delivery system and their patents," M. N. Siddiqui, G. Garg, P. K. Sharma, *Adv. Biol. Res.*, 5 (2011), pp. 291-303; "Orally disintegrating films: A modern expansion in drug delivery system," Ifran et al., *Saudi Pharmaceutical Journal*, Volume 24, Issue 5, pp. 537-546 (September 2016); "Development and characterization of pharmacokinetic parameters of fast-dissolving films containing levocetirizine," D. R. Choudhary, V. A. Patel, U. K. Chhalotiya, H. V. Patel, A. J. Kundawala; *Sci. Pharm.*, 80 (2012), pp. 779-787; "Orally disintegrating preparations: recent advancement in formulation and technology," R. R. Thakur, D. S. Rathore, S. Narwal; *J. Drug Deliv. Therap.*, 2 (3) (2012), pp. 87-96; "Development of innovative orally fast disintegrating film dosage forms: a review," B. P. Panda, N. S. Dey, M. E. B. Rao; *Int. J. Pharm. Sci. Nanotechnol.*, 5 (2012), pp. 1666-1674.

Several methods for manufacturing an oral soluble film may be pursued, but the most common is solvent casting. Using this method, the manufacturing process can start with dispensing the excipients, active ingredient and solvent(s) in a defined order, preferably into a temperature-controlled tank and blending them into a slurry, typically using a high shear mixer to achieve a homogenous slurry. Homogeneity of the slurry should be tested by sampling at different locations in the tank and measuring viscosity and solids content. Depending on the properties of the slurry (i.e., bacteriostatic, bactericidal or growth promoting), in-process bioburden testing may be employed. To ensure flexibility of production scheduling, optimal conditions for storing the slurry should be tested.

The slurry may then be fed into an oven through a coating station, typically using a pump system. The slurry may be applied to a liner using a slot die or knife-over-roll coater, at a determined pin gauge. The selection of the liner can affect how the solvent (e.g., water) will evaporate and should generally be selected as to mitigate the occurrence of any chemical interaction with the film. Relevant parameters when selecting a liner are moisture content of the cast film, the location of the heat source and the directionality and strength of the air flow within the oven. It is generally preferred to "bake" the film rather than "broil" it. Additionally, the liner will preferably be qualified by the FDA, e.g., having its own drug master file (DMF).

Casting parameters—oven temperature, pin gauge and belt speed—required to meet product specifications at the terminal end of the oven, are generally optimized to achieve the fastest belt speed for highest throughput and cost efficiencies. Some oven systems enable the operator to control the height and directionality of the air nozzles and offer modular heat zones (e.g., infrared, progressive temperature increase). Oven lengths generally range from 10 ft to 24 ft, or more. The film and liner may then be packed as master rolls at the terminal end of the oven and should be stored in a temperature and humidity-controlled environment as oral soluble films tend to be hygroscopic. Stability of the intermediate master rolls over time may be established by evaluating API content, moisture levels, physical characteristics, pliability dissolution, microbiology, and tensile strength. Typically, oral soluble film products are stable at room temperature in an appropriate container closure system. Of note, there is currently no official method or monograph in the US Pharmacopeia for evaluating oral soluble film properties such as disintegration, dissolution or mucoadhesion. Additionally, at the end of casting, additional API and/or occluding layer can be sprayed onto the cast film. Alternatively, the film can be 3D printed instead of casting.

Another step in the production is cutting the master roll into daughter rolls (alternatively referred to as "sitting") and further into single doses which can be placed into individual pouches or sachets by converting and packaging machines. Ink printing of a mark on the film can be carried out. The mark can include a logo or indicia, such as the company name and dosage (e.g., "CURR50"—corresponding to Cure Pharmaceutical Holding Corp. (OTC:CURR), and 50 mg sildenafil). The ink is preferably pharmaceutically acceptable and will not interfere with the performance characteristics (e.g., disintegration time) of the OSF. The API dose of an oral soluble film product is directly informed by the weight of the film. It is therefore critical to control the weight of each film product that is packaged. The size to which each individual film should cut must be determined during process development to ensure the product meets its the target weight and API load. A significant advantage with this dosage form is the ease in which multiple stock keeping units (SKUs) can be produced, by simply modifying the size or mass of the film.

Metalized polyester is a suitable primary packaging material for oral soluble film. It can be cost effective and protects the product from moisture and light. This pouch material can be child resistant and closure systems can be designed to ensure the product passes child resistant testing, while remaining user friendly for the patient. The pouches or sachets can offer larger printable 2D areas which traditional drug product formats do not. This allows the manufacturer to adapt to rapidly evolving labeling and regulatory requirements for information and anti-counterfeiting, such as product serialization. Furthermore, the primary package can provide sufficient space to include instructions on how to open the package and use the product, so that patients have a clear understanding of how it works. If desirable, each OSF can be individually packaged. One supplier of commercially available primary packaging materials is Bemis Company, Inc. (Neenah, Wis.).

The manufacturing of oral soluble films can be a continuous but modular process that is suitable to automation. The modularity of the process, such as master roll holds, allows for finished conversion to be done in the country or region of distribution, which compliments satellite expansion based on regional demand. The manufacturing process can have a low carbon footprint, with lower use of water for component preparation, as compared with other dosage forms.

Specific Ranges, Values, and Embodiments

The specific embodiments describing the ranges and values provided below are for illustration purposes only, and do not otherwise limit the scope of the disclosed subject matter, as defined by the claims.

Sildenafil Citrate

In specific embodiments, the sildenafil citrate is present in 36±10 wt. % of the oral soluble film.

In specific embodiments, the sildenafil citrate is present in 36±9 wt. % of the oral soluble film.

In specific embodiments, the sildenafil citrate is present in 36±8 wt. % of the oral soluble film.

In specific embodiments, the sildenafil citrate is present in 36±7 wt. % of the oral soluble film.

In specific embodiments, the sildenafil citrate is present in 36±6 wt. % of the oral soluble film.

In specific embodiments, the sildenafil citrate is present in 36±5 wt. % of the oral soluble film.

In specific embodiments, the sildenafil citrate is present in 36±4 wt. % of the oral soluble film.

In specific embodiments, the sildenafil citrate is present in 36±3 wt. % of the oral soluble film.

In specific embodiments, the sildenafil citrate is present in 36±2 wt. % of the oral soluble film.

In specific embodiments, the sildenafil citrate is present in 36±1 wt. % of the oral soluble film.

In specific embodiments, the sildenafil citrate is present in 36±0.5 wt. % of the oral soluble film.

In specific embodiments, the sildenafil citrate is present in 36±0.25 wt. % of the oral soluble film.

In specific embodiments, the sildenafil citrate is present in 34.29±10 wt. % of the oral soluble film, based on a 5±1.5 wt. % hydrated film.

In specific embodiments, the sildenafil citrate is present in 34.29±9 wt. % of the oral soluble film, based on a 5±1.5 wt. % hydrated film.

In specific embodiments, the sildenafil citrate is present in 34.29±8 wt. % of the oral soluble film, based on a 5±1.5 wt. % hydrated film.

In specific embodiments, the sildenafil citrate is present in 34.29±7 wt. % of the oral soluble film, based on a 5±1.5 wt. % hydrated film.

In specific embodiments, the sildenafil citrate is present in 34.29±6 wt. % of the oral soluble film, based on a 5±1.5 wt. % hydrated film.

In specific embodiments, the sildenafil citrate is present in 34.29±5 wt. % of the oral soluble film, based on a 5±1.5 wt. % hydrated film.

In specific embodiments, the sildenafil citrate is present in 34.29±4 wt. % of the oral soluble film, based on a 5±1.5 wt. % hydrated film.

In specific embodiments, the sildenafil citrate is present in 34.29±3 wt. % of the oral soluble film, based on a 5±1.5 wt. % hydrated film.

In specific embodiments, the sildenafil citrate is present in 34.29±2 wt. % of the oral soluble film, based on a 5±1.5 wt. % hydrated film.

In specific embodiments, the sildenafil citrate is present in 34.29±1 wt. % of the oral soluble film, based on a 5±1.5 wt. % hydrated film.

In specific embodiments, the sildenafil citrate is present in 34.29±0.5 wt. % of the oral soluble film, based on a 5±1.5 wt. % hydrated film.

In specific embodiments, the sildenafil citrate is present in 34.29±0.25 wt. % of the oral soluble film, based on a 5±1.5 wt. % hydrated film.

In specific embodiments, the oral soluble film is configured as a unit dose and the sildenafil citrate is present in 70.24±10 mg.

In specific embodiments, the oral soluble film is configured as a unit dose and the sildenafil citrate is present in 70.24±9 mg.

In specific embodiments, the oral soluble film is configured as a unit dose and the sildenafil citrate is present in 70.24±8 mg.

In specific embodiments, the oral soluble film is configured as a unit dose and the sildenafil citrate is present in 70.24±7 mg.

In specific embodiments, the oral soluble film is configured as a unit dose and the sildenafil citrate is present in 70.24±6 mg.

In specific embodiments, the oral soluble film is configured as a unit dose and the sildenafil citrate is present in 70.24±5 mg.

In specific embodiments, the oral soluble film is configured as a unit dose and the sildenafil citrate is present in 70.24±4 mg.

In specific embodiments, the oral soluble film is configured as a unit dose and the sildenafil citrate is present in 70.24±3 mg.

In specific embodiments, the oral soluble film is configured as a unit dose and the sildenafil citrate is present in 70.24±2 mg.

In specific embodiments, the oral soluble film is configured as a unit dose and the sildenafil citrate is present in 70.24±1 mg.

In specific embodiments, the oral soluble film is configured as a unit dose and the sildenafil citrate is present in 70.24±0.5 mg.

In specific embodiments, the oral soluble film is in the form of a unit dose and the sildenafil citrate is present in an amount equivalent to 25 mg, 50 mg, or 100 mg of sildenafil, as the free base.

In specific embodiments, the oral soluble film is in the form of a unit dose and the sildenafil citrate is present in an amount equivalent to 22.5-27.5 mg of sildenafil, as the free base.

In specific embodiments, the sildenafil citrate is present in an amount of up to 0.30 mg/mm$^3$.

In specific embodiments, the sildenafil citrate is present in an amount of at least 0.20 mg/mm$^3$.

In specific embodiments, the sildenafil citrate is present in an amount of 0.24±0.06 mg/mm$^3$.

In specific embodiments, the sildenafil citrate is present in an amount of 0.24±0.05 mg/mm$^3$.

In specific embodiments, the sildenafil citrate is present in an amount of 0.24±0.04 mg/mm$^3$.

In specific embodiments, the sildenafil citrate is present in an amount of 0.24±0.03 mg/mm$^3$.

In specific embodiments, the sildenafil citrate is present in an amount of 0.24±0.02 mg/mm$^3$.

In specific embodiments, the sildenafil citrate is present in an amount of 0.24±0.01 mg/mm$^3$.

In specific embodiments, the oral soluble film is in the form of a unit dose and the sildenafil citrate is present in an amount equivalent to 25 mg of sildenafil, as the free base.

In specific embodiments, the oral soluble film is in the form of a unit dose and the sildenafil citrate is present in an amount equivalent to 45-55 mg of sildenafil, as the free base.

In specific embodiments, the oral soluble film is in the form of a unit dose and the sildenafil citrate is present in an amount equivalent to 50 mg of sildenafil, as the free base.

In specific embodiments, the oral soluble film is in the form of a unit dose and the sildenafil citrate is present in an amount equivalent to 50±5 mg of sildenafil, as the free base.

In specific embodiments, the oral soluble film is in the form of a unit dose and the sildenafil citrate is present in an amount equivalent to 90-110 mg of sildenafil, as the free base.

In specific embodiments, the oral soluble film is in the form of a unit dose and the sildenafil citrate is present in an amount equivalent to 100 mg of sildenafil, as the free base.

In specific embodiments, the oral soluble film includes non-non-micronized sildenafil citrate.

In specific embodiments, the oral soluble film is manufactured from non-micronized sildenafil citrate having the following particle size distribution (PSD): Dv(10) of less than 2 μm.

In specific embodiments, the oral soluble film is manufactured from non-micronized sildenafil citrate having the following particle size distribution (PSD): Dv(50) of less than 5 μm.

In specific embodiments, the oral soluble film is manufactured from non-micronized sildenafil citrate having the following particle size distribution (PSD): Dv(90) of less than 60 μm.

In specific embodiments, the oral soluble film is manufactured from non-micronized sildenafil citrate having the following particle size distribution (PSD): Dv(90) of less than 35 μm.

In specific embodiments, the oral soluble film is manufactured from non-micronized sildenafil citrate having the following particle size distribution (PSD): Dv(10) of less than 2 μm, Dv(50) of less than 5 μm, and Dv(90) of less than 35 μm.

In specific embodiments, the oral soluble film is obtained from a slurry wherein the sildenafil citrate is present in 16.8±3 wt. % of the slurry.

In specific embodiments, the oral soluble film is obtained from a slurry wherein the sildenafil citrate is present in 16.8±2.5 wt. % of the slurry.

In specific embodiments, the oral soluble film is obtained from a slurry wherein the sildenafil citrate is present in 16.8±2 wt. % of the slurry.

In specific embodiments, the oral soluble film is obtained from a slurry wherein the sildenafil citrate is present in 16.8±1.75 wt. % of the slurry.

In specific embodiments, the oral soluble film is obtained from a slurry wherein the sildenafil citrate is present in 16.8±1.5 wt. % of the slurry.

In specific embodiments, the oral soluble film is obtained from a slurry wherein the sildenafil citrate is present in 16.8±1 wt. % of the slurry.

In specific embodiments, the oral soluble film is obtained from a slurry wherein the sildenafil citrate is present in 16.8±0.5 wt. % of the slurry.

In specific embodiments, the variation of sildenafil citrate between two equally sized unit dosages is less than 20 wt. %.

In specific embodiments, the variation of sildenafil citrate between two equally sized unit dosages is less than 15 wt. %.

In specific embodiments, the variation of sildenafil citrate between two equally sized unit dosages is less than 10 wt. %.

In specific embodiments, the variation of sildenafil citrate between two equally sized unit dosages is less than 5 wt. %.

In specific embodiments, the variation of sildenafil citrate between two equally sized unit dosages is less than 2.5 wt. %.

In specific embodiments, the variation of sildenafil citrate between two equally sized unit dosages is less than 1 wt. %.

In specific embodiments, the variation of sildenafil citrate between two equally sized unit dosages is less than 0.5 wt. %.

Binder

In specific embodiments, the binder is present in 30±10 wt. % of the oral soluble film.

In specific embodiments, the binder is present in 30±9 wt. % of the oral soluble film.

In specific embodiments, the binder is present in 30±8 wt. % of the oral soluble film.

In specific embodiments, the binder is present in 30±7 wt. % of the oral soluble film.

In specific embodiments, the binder is present in 30±6 wt. % of the oral soluble film.

In specific embodiments, the binder is present in 30±5 wt. % of the oral soluble film.

In specific embodiments, the binder is present in 30±4 wt. % of the oral soluble film.

In specific embodiments, the binder is present in 30±3 wt. % of the oral soluble film.

In specific embodiments, the binder is present in 30±2 wt. % of the oral soluble film.

In specific embodiments, the binder is present in 30±1 wt. % of the oral soluble film.

In specific embodiments, the binder is present in 28.57±10 wt. % of the oral soluble film, based on a 5±1.5 wt. % hydrated film.

In specific embodiments, the binder is present in 28.57±9 wt. % of the oral soluble film, based on a 5±1.5 wt. % hydrated film.

In specific embodiments, the binder is present in 28.57±8 wt. % of the oral soluble film, based on a 5±1.5 wt. % hydrated film.

In specific embodiments, the binder is present in 28.57±7 wt. % of the oral soluble film, based on a 5±1.5 wt. % hydrated film.

In specific embodiments, the binder is present in 28.57±6 wt. % of the oral soluble film, based on a 5±1.5 wt. % hydrated film.

In specific embodiments, the binder is present in 28.57±5 wt. % of the oral soluble film, based on a 5±1.5 wt. % hydrated film.

In specific embodiments, the binder is present in 28.57±4 wt. % of the oral soluble film, based on a 5±1.5 wt. % hydrated film.

In specific embodiments, the binder is present in 28.57±3 wt. % of the oral soluble film, based on a 5±1.5 wt. % hydrated film.

In specific embodiments, the binder is present in 28.57±2 wt. % of the oral soluble film, based on a 5±1.5 wt. % hydrated film.

In specific embodiments, the binder is present in 28.57±1 wt. % of the oral soluble film, based on a 5±1.5 wt. % hydrated film.

In specific embodiments, the oral soluble film is configured as a unit dose and the binder is present in 58.53±18 mg.

In specific embodiments, the oral soluble film is configured as a unit dose and the binder is present in 58.53±16 mg.

In specific embodiments, the oral soluble film is configured as a unit dose and the binder is present in 58.53±14 mg.

In specific embodiments, the oral soluble film is configured as a unit dose and the binder is present in 58.53±12 mg.

In specific embodiments, the oral soluble film is configured as a unit dose and the binder is present in 58.53±10 mg.

In specific embodiments, the oral soluble film is configured as a unit dose and the binder is present in 58.53±8 mg.

In specific embodiments, the oral soluble film is configured as a unit dose and the binder is present in 58.53±7 mg.

In specific embodiments, the oral soluble film is configured as a unit dose and the binder is present in 58.53±6 mg.

In specific embodiments, the oral soluble film is configured as a unit dose and the binder is present in 58.53±5 mg.

In specific embodiments, the oral soluble film is configured as a unit dose and the binder is present in 58.53±4 mg.

In specific embodiments, the oral soluble film is obtained from a slurry wherein the binder is present in 14.1±3 wt. % of the slurry.

In specific embodiments, the oral soluble film is obtained from a slurry wherein the binder is present in 14.1±2.5 wt. % of the slurry.

In specific embodiments, the oral soluble film is obtained from a slurry wherein the binder is present in 14.1±2 wt. % of the slurry.

In specific embodiments, the oral soluble film is obtained from a slurry wherein the binder is present in 14.1±1.75 wt. % of the slurry.

In specific embodiments, the oral soluble film is obtained from a slurry wherein the binder is present in 14.1±1.5 wt. % of the slurry.

In specific embodiments, the oral soluble film is obtained from a slurry wherein the binder is present in 14.1±1 wt. % of the slurry.

In specific embodiments, the oral soluble film is obtained from a slurry wherein the binder is present in 14.1±0.5 wt. % of the slurry.

In specific embodiments, the binder includes Kollicoat® Protect.

In specific embodiments, the binder includes Kollicoat® Protect, which includes: Kollicoat® IR, polyvinylalcohol, and silicon dioxide.

In specific embodiments, the binder includes (i) polyvinyl alcohol (PVA); (ii) polyvinyl alcohol (PVA)-polyethylene glycol (PEG) graft copolymer; and (iii) silicon dioxide.

In specific embodiments, the Kollicoat® Protect functions as a binder.

In specific embodiments, the Kollicoat® Protect functions as a binder and at least one of a film-coating agent, disintegrating agent, taste masking agent, emulsifier, to increase tensile strength of the OSF and/or elongation, and anti-caking agent.

In specific embodiments, the Kollicoat® Protect is present in 30±10 wt. % of the oral soluble film.

In specific embodiments, the Kollicoat® Protect is present in 30±9 wt. % of the oral soluble film.

In specific embodiments, the Kollicoat® Protect is present in 30±8 wt. % of the oral soluble film.

In specific embodiments, the Kollicoat® Protect is present in 30±7 wt. % of the oral soluble film.

In specific embodiments, the Kollicoat® Protect is present in 30±6 wt. % of the oral soluble film.

In specific embodiments, the Kollicoat® Protect is present in 30±5 wt. % of the oral soluble film.

In specific embodiments, the Kollicoat® Protect is present in 30±4 wt. % of the oral soluble film.

In specific embodiments, the Kollicoat® Protect is present in 30±3 wt. % of the oral soluble film.

In specific embodiments, the Kollicoat® Protect is present in 30±2 wt. % of the oral soluble film.

In specific embodiments, the Kollicoat® Protect is present in 30±1 wt. % of the oral soluble film.

In specific embodiments, the Kollicoat® Protect is present in 28.57±10 wt. % of the oral soluble film, based on a 5±1.5 wt. % hydrated film.

In specific embodiments, the Kollicoat® Protect is present in 28.57±9 wt. % of the oral soluble film, based on a 5±1.5 wt. % hydrated film.

In specific embodiments, the Kollicoat® Protect is present in 28.57±8 wt. % of the oral soluble film, based on a 5±1.5 wt. % hydrated film.

In specific embodiments, the Kollicoat® Protect is present in 28.57±7 wt. % of the oral soluble film, based on a 5±1.5 wt. % hydrated film.

In specific embodiments, the Kollicoat® Protect is present in 28.57±6 wt. % of the oral soluble film, based on a 5±1.5 wt. % hydrated film.

In specific embodiments, the Kollicoat® Protect is present in 28.57±5 wt. % of the oral soluble film, based on a 5±1.5 wt. % hydrated film.

In specific embodiments, the Kollicoat® Protect is present in 28.57±4 wt. % of the oral soluble film, based on a 5±1.5 wt. % hydrated film.

In specific embodiments, the Kollicoat® Protect is present in 28.57±3 wt. % of the oral soluble film, based on a 5±1.5 wt. % hydrated film.

In specific embodiments, the Kollicoat® Protect is present in 28.57±2 wt. % of the oral soluble film, based on a 5±1.5 wt. % hydrated film.

In specific embodiments, the Kollicoat® Protect is present in 28.57±1 wt. % of the oral soluble film, based on a 5±1.5 wt. % hydrated film.

In specific embodiments, the oral soluble film is configured as a unit dose and the Kollicoat® Protect is present in 58.53±18 mg.

In specific embodiments, the oral soluble film is configured as a unit dose and the Kollicoat® Protect is present in 58.53±16 mg.

In specific embodiments, the oral soluble film is configured as a unit dose and the Kollicoat® Protect is present in 58.53±14 mg.

In specific embodiments, the oral soluble film is configured as a unit dose and the Kollicoat® Protect is present in 58.53±12 mg.

In specific embodiments, the oral soluble film is configured as a unit dose and the Kollicoat® Protect is present in 58.53±10 mg.

In specific embodiments, the oral soluble film is configured as a unit dose and the Kollicoat® Protect is present in 58.53±8 mg.

In specific embodiments, the oral soluble film is configured as a unit dose and the Kollicoat® Protect is present in 58.53±7 mg.

In specific embodiments, the oral soluble film is configured as a unit dose and the Kollicoat® Protect is present in 58.53±6 mg.

In specific embodiments, the oral soluble film is configured as a unit dose and the Kollicoat® Protect is present in 58.53±5 mg.

In specific embodiments, the oral soluble film is configured as a unit dose and the Kollicoat® Protect is present in 58.53±4 mg.

In specific embodiments, the oral soluble film is obtained from a slurry wherein the Kollicoat® Protect is present in 14.1±3 wt. % of the slurry.

In specific embodiments, the oral soluble film is obtained from a slurry wherein the Kollicoat® Protect is present in 14.1±2.5 wt. % of the slurry.

In specific embodiments, the oral soluble film is obtained from a slurry wherein the Kollicoat® Protect is present in 14.1±2 wt. % of the slurry.

In specific embodiments, the oral soluble film is obtained from a slurry wherein the Kollicoat® Protect is present in 14.1±1.75 wt. % of the slurry.

In specific embodiments, the oral soluble film is obtained from a slurry wherein the Kollicoat® Protect is present in 14.1±1.5 wt. % of the slurry.

In specific embodiments, the oral soluble film is obtained from a slurry wherein the Kollicoat® Protect is present in 14.1±1 wt. % of the slurry.

In specific embodiments, the oral soluble film is obtained from a slurry wherein the Kollicoat® Protect is present in 14.1±0.5 wt. % of the slurry.

Filler

In specific embodiments, the filler is present in 5.45±2.5 wt. % of the oral soluble film.

In specific embodiments, the filler is present in 5.45±2 wt. % of the oral soluble film.

In specific embodiments, the filler is present in 5.45±1.5 wt. % of the oral soluble film.

In specific embodiments, the filler is present in 5.19±1 wt. % of the oral soluble film, based on a 5±1.5 wt. % hydrated film.

In specific embodiments, the filler is present in 5.19±0.5 wt. % of the oral soluble film, based on a 5±1.5 wt. % hydrated film.

In specific embodiments, the filler is present in 5.19±2.5 wt. % of the oral soluble film, based on a 5±1.5 wt. % hydrated film.

In specific embodiments, the filler is present in 5.19±2 wt. % of the oral soluble film, based on a 5±1.5 wt. % hydrated film.

In specific embodiments, the filler is present in 5.19±1.5 wt. % of the oral soluble film, based on a 5±1.5 wt. % hydrated film.

In specific embodiments, the filler is present in 5.19±1.25 wt. % of the oral soluble film, based on a 5±1.5 wt. % hydrated film.

In specific embodiments, the filler is present in 5.19±1 wt. % of the oral soluble film, based on a 5±1.5 wt. % hydrated film.

In specific embodiments, the filler is present in 5.19±0.75 wt. % of the oral soluble film, based on a 5±1.5 wt. % hydrated film.

In specific embodiments, the filler is present in 5.19±0.5 wt. % of the oral soluble film, based on a 5±1.5 wt. % hydrated film.

In specific embodiments, the oral soluble film is configured as a unit dose and the filler is present in 10.63±5 mg.

In specific embodiments, the oral soluble film is configured as a unit dose and the filler is present in 10.63±4 mg.

In specific embodiments, the oral soluble film is configured as a unit dose and the filler is present in 10.63±3 mg.

In specific embodiments, the oral soluble film is configured as a unit dose and the filler is present in 10.63±2 mg.

In specific embodiments, the oral soluble film is configured as a unit dose and the filler is present in 10.63±1 mg.

In specific embodiments, the oral soluble film is obtained from a slurry wherein the filler is present in 2.5±1.5 wt. % of the slurry.

In specific embodiments, the oral soluble film is obtained from a slurry wherein the filler is present in 2.5±1.25 wt. % of the slurry.

In specific embodiments, the oral soluble film is obtained from a slurry wherein the filler is present in 2.5±1 wt. % of the slurry.

In specific embodiments, the oral soluble film is obtained from a slurry wherein the filler is present in 2.5±1.75 wt. % of the slurry.

In specific embodiments, the oral soluble film is obtained from a slurry wherein the filler is present in 2.5±1.5 wt. % of the slurry.

In specific embodiments, the oral soluble film is obtained from a slurry wherein the filler is present in 2.5±1.25 wt. % of the slurry.

In specific embodiments, the oral soluble film is obtained from a slurry wherein the filler is present in 2.5±1 wt. % of the slurry.

In specific embodiments, the oral soluble film is obtained from a slurry wherein the filler is present in 2.5±0.75 wt. % of the slurry.

In specific embodiments, the oral soluble film is obtained from a slurry wherein the filler is present in 2.5±0.5 wt. % of the slurry.

In specific embodiments, the oral soluble film is obtained from a slurry wherein the filler is present in 2.5±0.25 wt. % of the slurry.

In specific embodiments, the oral soluble film is obtained from a slurry wherein the filler is present in 2.5±0.1 wt. % of the slurry.

In specific embodiments, the filler includes microcrystalline cellulose.

In specific embodiments, the microcrystalline cellulose functions as a filler and binder.

In specific embodiments, the microcrystalline cellulose functions as a filler and binder, and at least one of an anti-caking agent, emulsifier, bulking agent, and viscosity increasing agent.

In specific embodiments, the microcrystalline cellulose is present in 5.45±2.5 wt. % of the oral soluble film.

In specific embodiments, the microcrystalline cellulose is present in 5.45±2 wt. % of the oral soluble film.

In specific embodiments, the microcrystalline cellulose is present in 5.45±1.5 wt. % of the oral soluble film.

In specific embodiments, the microcrystalline cellulose is present in 5.45±1 wt. % of the oral soluble film.

In specific embodiments, the microcrystalline cellulose is present in 5.45±0.5 wt. % of the oral soluble film.

In specific embodiments, the microcrystalline cellulose is present in 5.19±2.5 wt. % of the oral soluble film, based on a 5±1.5 wt. % hydrated film.

In specific embodiments, the microcrystalline cellulose is present in 5.19±2 wt. % of the oral soluble film, based on a 5±1.5 wt. % hydrated film.

In specific embodiments, the microcrystalline cellulose is present in 5.19±1.5 wt. % of the oral soluble film, based on a 5±1.5 wt. % hydrated film.

In specific embodiments, the microcrystalline cellulose is present in 5.19±1 wt. % of the oral soluble film, based on a 5±1.5 wt. % hydrated film.

In specific embodiments, the microcrystalline cellulose is present in 5.19±0.5 wt. % of the oral soluble film, based on a 5±1.5 wt. % hydrated film.

In specific embodiments, the oral soluble film is configured as a unit dose and the microcrystalline cellulose is present in 10.63±5 mg.

In specific embodiments, the oral soluble film is configured as a unit dose and the microcrystalline cellulose is present in 10.63±4 mg.

In specific embodiments, the oral soluble film is configured as a unit dose and the microcrystalline cellulose is present in 10.63±3 mg.

In specific embodiments, the oral soluble film is configured as a unit dose and the microcrystalline cellulose is present in 10.63±2 mg.

In specific embodiments, the oral soluble film is configured as a unit dose and the microcrystalline cellulose is present in 10.63±1 mg.

In specific embodiments, the oral soluble film is obtained from a slurry wherein the microcrystalline cellulose is present in 2.5±1.5 wt. % of the slurry.

In specific embodiments, the oral soluble film is obtained from a slurry wherein the microcrystalline cellulose is present in 2.5±1.25 wt. % of the slurry.

In specific embodiments, the oral soluble film is obtained from a slurry wherein the microcrystalline cellulose is present in 2.5±1 wt. % of the slurry.

In specific embodiments, the oral soluble film is obtained from a slurry wherein the microcrystalline cellulose is present in 2.5±0.75 wt. % of the slurry.

In specific embodiments, the oral soluble film is obtained from a slurry wherein the microcrystalline cellulose is present in 2.5±0.5 wt. % of the slurry.

In specific embodiments, the oral soluble film is obtained from a slurry wherein the microcrystalline cellulose is present in 2.5±0.25 wt. % of the slurry.

In specific embodiments, the oral soluble film is obtained from a slurry wherein the microcrystalline cellulose is present in 2.5±0.1 wt. % of the slurry.

Flavoring Agent

In specific embodiments, the flavoring agent is present in 6.44±3.5 wt. % of the oral soluble film.

In specific embodiments, the flavoring agent is present in 6.44±3 wt. % of the oral soluble film.

In specific embodiments, the flavoring agent is present in 6.44±2.5 wt. % of the oral soluble film.

In specific embodiments, the flavoring agent is present in 6.44±2 wt. % of the oral soluble film.

In specific embodiments, the flavoring agent is present in 6.44±1.5 wt. % of the oral soluble film.

In specific embodiments, the flavoring agent is present in 6.44±1.25 wt. % of the oral soluble film.

In specific embodiments, the flavoring agent is present in 6.44±1 wt. % of the oral soluble film.

In specific embodiments, the flavoring agent is present in 6.44±0.5 wt. % of the oral soluble film.

In specific embodiments, the flavoring agent is present in 6.13±3.5 wt. % of the oral soluble film, based on a 5±1.5 wt. % hydrated film.

In specific embodiments, the flavoring agent is present in 6.13±3 wt. % of the oral soluble film, based on a 5±1.5 wt. % hydrated film.

In specific embodiments, the flavoring agent is present in 6.13±2.5 wt. % of the oral soluble film, based on a 5±1.5 wt. % hydrated film.

In specific embodiments, the flavoring agent is present in 6.13±2 wt. % of the oral soluble film, based on a 5±1.5 wt. % hydrated film.

In specific embodiments, the flavoring agent is present in 6.13±1.5 wt. % of the oral soluble film, based on a 5±1.5 wt. % hydrated film.

In specific embodiments, the flavoring agent is present in 6.13±1.25 wt. % of the oral soluble film, based on a 5±1.5 wt. % hydrated film.

In specific embodiments, the flavoring agent is present in 6.13±1 wt. % of the oral soluble film, based on a 5±1.5 wt. % hydrated film.

In specific embodiments, the flavoring agent is present in 6.13±0.5 wt. % of the oral soluble film, based on a 5±1.5 wt. % hydrated film.

In specific embodiments, the oral soluble film is configured as a unit dose and the flavoring agent is present in 12.56±4 mg.

In specific embodiments, the oral soluble film is configured as a unit dose and the flavoring agent is present in 12.56±3.5 mg.

In specific embodiments, the oral soluble film is configured as a unit dose and the flavoring agent is present in 12.56±3 mg.

In specific embodiments, the oral soluble film is configured as a unit dose and the flavoring agent is present in 12.56±2.5 mg.

In specific embodiments, the oral soluble film is configured as a unit dose and the flavoring agent is present in 12.56±2 mg.

In specific embodiments, the oral soluble film is configured as a unit dose and the flavoring agent is present in 12.56±1.5 mg.

In specific embodiments, the oral soluble film is obtained from a slurry wherein the flavoring agent is present in 3.0±1.5 wt. % of the slurry.

In specific embodiments, the oral soluble film is obtained from a slurry wherein the flavoring agent is present in 3.0±1.25 wt. % of the slurry.

In specific embodiments, the oral soluble film is obtained from a slurry wherein the flavoring agent is present in 3.0±1 wt. % of the slurry.

In specific embodiments, the oral soluble film is obtained from a slurry wherein the flavoring agent is present in 3.0±0.75 wt. % of the slurry.

In specific embodiments, the oral soluble film is obtained from a slurry wherein the flavoring agent is present in 3.0±0.5 wt. % of the slurry.

In specific embodiments, the oral soluble film is obtained from a slurry wherein the flavoring agent is present in 3.0±0.25 wt. % of the slurry.

In specific embodiments, the oral soluble film is obtained from a slurry wherein the flavoring agent is present in 3.0±0.1 wt. % of the slurry.

In specific embodiments, the flavoring agent includes spearmint flavoring.

In specific embodiments, the flavoring agent includes orange flavoring.

In specific embodiments, the flavoring agent includes vanilla cream flavoring.

In specific embodiments, the flavoring agent includes peppermint flavoring.

In specific embodiments, the peppermint flavoring functions as a flavoring agent and at least one of a taste masking agent and permeation enhancer.

In specific embodiments, the peppermint flavoring is present in 6.44±3.5 wt. % of the oral soluble film.

In specific embodiments, the peppermint flavoring is present in 6.44±3 wt. % of the oral soluble film.

In specific embodiments, the peppermint flavoring is present in 6.44±2.5 wt. % of the oral soluble film.

In specific embodiments, the peppermint flavoring is present in 6.44±2 wt. % of the oral soluble film.

In specific embodiments, the peppermint flavoring is present in 6.44±1.5 wt. % of the oral soluble film.

In specific embodiments, the peppermint flavoring is present in 6.44±1.25 wt. % of the oral soluble film.

In specific embodiments, the peppermint flavoring is present in 6.44±1 wt. % of the oral soluble film.

In specific embodiments, the peppermint flavoring is present in 6.44±0.5 wt. % of the oral soluble film.

In specific embodiments, the peppermint flavoring is present in 6.13±3.5 wt. % of the oral soluble film, based on a 5±1.5 wt. % hydrated film.

In specific embodiments, the peppermint flavoring is present in 6.13±3 wt. % of the oral soluble film, based on a 5±1.5 wt. % hydrated film.

In specific embodiments, the peppermint flavoring is present in 6.13±2.5 wt. % of the oral soluble film, based on a 5±1.5 wt. % hydrated film.

In specific embodiments, the peppermint flavoring is present in 6.13±2 wt. % of the oral soluble film, based on a 5±1.5 wt. % hydrated film.

In specific embodiments, the peppermint flavoring is present in 6.13±1.5 wt. % of the oral soluble film, based on a 5±1.5 wt. % hydrated film.

In specific embodiments, the peppermint flavoring is present in 6.13±1.25 wt. % of the oral soluble film, based on a 5±1.5 wt. % hydrated film.

In specific embodiments, the peppermint flavoring is present in 6.13±1 wt. % of the oral soluble film, based on a 5±1.5 wt. % hydrated film.

In specific embodiments, the peppermint flavoring is present in 6.13±0.5 wt. % of the oral soluble film, based on a 5±1.5 wt. % hydrated film.

In specific embodiments, the oral soluble film is configured as a unit dose and the peppermint flavoring is present in 12.56±4 mg.

In specific embodiments, the oral soluble film is configured as a unit dose and the peppermint flavoring is present in 12.56±3.5 mg.

In specific embodiments, the oral soluble film is configured as a unit dose and the peppermint flavoring is present in 12.56±3 mg.

In specific embodiments, the oral soluble film is configured as a unit dose and the peppermint flavoring is present in 12.56±2.5 mg.

In specific embodiments, the oral soluble film is configured as a unit dose and the peppermint flavoring is present in 12.56±2 mg.

In specific embodiments, the oral soluble film is configured as a unit dose and the peppermint flavoring is present in 12.56±1.5 mg.

In specific embodiments, the oral soluble film is obtained from a slurry wherein the peppermint flavoring is present in 3.0±1.5 wt. % of the slurry.

In specific embodiments, the oral soluble film is obtained from a slurry wherein the peppermint flavoring is present in 3.0±1.25 wt. % of the slurry.

In specific embodiments, the oral soluble film is obtained from a slurry wherein the peppermint flavoring is present in 3.0±1 wt. % of the slurry.

In specific embodiments, the oral soluble film is obtained from a slurry wherein the peppermint flavoring is present in 3.0±0.75 wt. % of the slurry.

In specific embodiments, the oral soluble film is obtained from a slurry wherein the peppermint flavoring is present in 3.0±0.5 wt. % of the slurry.

In specific embodiments, the oral soluble film is obtained from a slurry wherein the peppermint flavoring is present in 3.0±0.25 wt. % of the slurry.

In specific embodiments, the oral soluble film is obtained from a slurry wherein the peppermint flavoring is present in 3.0±0.1 wt. % of the slurry.

Plasticizer

In specific embodiments, the plasticizer is present in 12±4 wt. % of the oral soluble film.

In specific embodiments, the plasticizer is present in 12±3.5 wt. % of the oral soluble film.

In specific embodiments, the plasticizer is present in 12±2.5 wt. % of the oral soluble film.

In specific embodiments, the plasticizer is present in 12±2 wt. % of the oral soluble film.

In specific embodiments, the plasticizer is present in 12±1.5 wt. % of the oral soluble film.

In specific embodiments, the plasticizer is present in 12±0.5 wt. % of the oral soluble film.

In specific embodiments, the plasticizer is present in 11.43±4 wt. % of the oral soluble film, based on a 5±1.5 wt. % hydrated film.

In specific embodiments, the plasticizer is present in 11.43±3.5 wt. % of the oral soluble film, based on a 5±1.5 wt. % hydrated film.

In specific embodiments, the plasticizer is present in 11.43±2.5 wt. % of the oral soluble film, based on a 5±1.5 wt. % hydrated film.

In specific embodiments, the plasticizer is present in 11.43±2 wt. % of the oral soluble film, based on a 5±1.5 wt. % hydrated film.

In specific embodiments, the plasticizer is present in 11.43±1.5 wt. % of the oral soluble film, based on a 5±1.5 wt. % hydrated film.

In specific embodiments, the plasticizer is present in 11.43±1 wt. % of the oral soluble film, based on a 5±1.5 wt. % hydrated film.

In specific embodiments, the plasticizer is present in 11.43±0.5 wt. % of the oral soluble film, based on a 5±1.5 wt. % hydrated film.

In specific embodiments, the oral soluble film is configured as a unit dose and the plasticizer is present in 23.41±12 mg.

In specific embodiments, the oral soluble film is configured as a unit dose and the plasticizer is present in 23.41±10 mg.

In specific embodiments, the oral soluble film is configured as a unit dose and the plasticizer is present in 23.41±8 mg.

In specific embodiments, the oral soluble film is configured as a unit dose and the plasticizer is present in 23.41±6 mg.

In specific embodiments, the oral soluble film is configured as a unit dose and the plasticizer is present in 23.41±5 mg.

In specific embodiments, the oral soluble film is configured as a unit dose and the plasticizer is present in 23.41±4 mg.

In specific embodiments, the oral soluble film is configured as a unit dose and the plasticizer is present in 23.41±3 mg.

In specific embodiments, the oral soluble film is configured as a unit dose and the plasticizer is present in 23.41±2 mg.

In specific embodiments, the oral soluble film is obtained from a slurry wherein the plasticizer is present in 5.6±1.5 wt. % of the slurry.

In specific embodiments, the oral soluble film is obtained from a slurry wherein the plasticizer is present in 5.6±1.25 wt. % of the slurry.

In specific embodiments, the oral soluble film is obtained from a slurry wherein the plasticizer is present in 5.6±1 wt. % of the slurry.

In specific embodiments, the oral soluble film is obtained from a slurry wherein the plasticizer is present in 5.6±0.75 wt. % of the slurry.

In specific embodiments, the oral soluble film is obtained from a slurry wherein the plasticizer is present in 5.6±0.5 wt. % of the slurry.

In specific embodiments, the oral soluble film is obtained from a slurry wherein the plasticizer is present in 5.6±0.25 wt. % of the slurry.

In specific embodiments, the oral soluble film is obtained from a slurry wherein the plasticizer is present in 5.6±0.1 wt. % of the slurry.

In specific embodiments, the plasticizer includes glycerin.

In specific embodiments, the glycerin functions as a plasticizer and at least one of a sweetener, humectant, solvent, thickening agent, and lubricant.

In specific embodiments, the glycerin is present in 12±4 wt. % of the oral soluble film.

In specific embodiments, the glycerin is present in 12±3.5 wt. % of the oral soluble film.

In specific embodiments, the glycerin is present in 12±2.5 wt. % of the oral soluble film.

In specific embodiments, the glycerin is present in 12±2 wt. % of the oral soluble film.

In specific embodiments, the glycerin is present in 12±1.5 wt. % of the oral soluble film.

In specific embodiments, the glycerin is present in 12±0.5 wt. % of the oral soluble film.

In specific embodiments, the glycerin is present in 11.43±4 wt. % of the oral soluble film.

In specific embodiments, the glycerin is present in 11.43±3.5 wt. % of the oral soluble film.

In specific embodiments, the glycerin is present in 11.43±2.5 wt. % of the oral soluble film.

In specific embodiments, the glycerin is present in 11.43±2 wt. % of the oral soluble film.

In specific embodiments, the glycerin is present in 11.43±1.5 wt. % of the oral soluble film.

In specific embodiments, the glycerin is present in 11.43±0.5 wt. % of the oral soluble film.

In specific embodiments, the oral soluble film is configured as a unit dose and the glycerin is present in 23.41±12 mg.

In specific embodiments, the oral soluble film is configured as a unit dose and the glycerin is present in 23.41±10 mg.

In specific embodiments, the oral soluble film is configured as a unit dose and the glycerin is present in 23.41±8 mg.

In specific embodiments, the oral soluble film is configured as a unit dose and the glycerin is present in 23.41±6 mg.

In specific embodiments, the oral soluble film is configured as a unit dose and the glycerin is present in 23.41±5 mg.

In specific embodiments, the oral soluble film is configured as a unit dose and the glycerin is present in 23.41±4 mg.

In specific embodiments, the oral soluble film is configured as a unit dose and the glycerin is present in 23.41±3 mg.

In specific embodiments, the oral soluble film is configured as a unit dose and the glycerin is present in 23.41±2 mg.

In specific embodiments, the oral soluble film is obtained from a slurry wherein the glycerin is present in 5.6±1.5 wt. % of the slurry.

In specific embodiments, the oral soluble film is obtained from a slurry wherein the glycerin is present in 5.6±1.25 wt. % of the slurry.

In specific embodiments, the oral soluble film is obtained from a slurry wherein the glycerin is present in 5.6±1 wt. % of the slurry.

In specific embodiments, the oral soluble film is obtained from a slurry wherein the glycerin is present in 5.6±0.75 wt. % of the slurry.

In specific embodiments, the oral soluble film is obtained from a slurry wherein the glycerin is present in 5.6±0.5 wt. % of the slurry.

In specific embodiments, the oral soluble film is obtained from a slurry wherein the glycerin is present in 5.6±0.25 wt. % of the slurry.

Sweetening Agent

In specific embodiments, the sweetening agent is present in 10±4 wt. % of the oral soluble film.

In specific embodiments, the sweetening agent is present in 10±3 wt. % of the oral soluble film.

In specific embodiments, the sweetening agent is present in 10±2 wt. % of the oral soluble film.

In specific embodiments, the sweetening agent is present in 10±1.5 wt. % of the oral soluble film.

In specific embodiments, the sweetening agent is present in 10±1 wt. % of the oral soluble film.

In specific embodiments, the sweetening agent is present in 10±0.5 wt. % of the oral soluble film.

In specific embodiments, the sweetening agent is present in 9.51±4 wt. % of the oral soluble film, based on a 5±1.5 wt. % hydrated film.

In specific embodiments, the sweetening agent is present in 9.51±3 wt. % of the oral soluble film, based on a 5±1.5 wt. % hydrated film.

In specific embodiments, the sweetening agent is present in 9.51±2 wt. % of the oral soluble film, based on a 5±1.5 wt. % hydrated film.

In specific embodiments, the sweetening agent is present in 9.51±1.5 wt. % of the oral soluble film, based on a 5±1.5 wt. % hydrated film.

In specific embodiments, the sweetening agent is present in 9.51±1 wt. % of the oral soluble film, based on a 5±1.5 wt. % hydrated film.

In specific embodiments, the sweetening agent is present in 9.51±0.5 wt. % of the oral soluble film, based on a 5±1.5 wt. % hydrated film.

In specific embodiments, the oral soluble film is configured as a unit dose and the sweetening agent is present in 19.5±6 mg.

In specific embodiments, the oral soluble film is configured as a unit dose and the sweetening agent is present in 19.5±5 mg.

In specific embodiments, the oral soluble film is configured as a unit dose and the sweetening agent is present in 19.5±4 mg.

In specific embodiments, the oral soluble film is configured as a unit dose and the sweetening agent is present in 19.5±3 mg.

In specific embodiments, the oral soluble film is configured as a unit dose and the sweetening agent is present in 19.5±2 mg.

In specific embodiments, the sweetening agent includes sucralose and acesulfame potassium (ACE-K).

In specific embodiments, the sweetening agent includes sucralose.

In specific embodiments, the sweetening agent includes sucralose, present in 6.0±2.5 wt. % of the oral soluble film.

In specific embodiments, the sweetening agent includes sucralose, present in 6.0±2 wt. % of the oral soluble film.

In specific embodiments, the sweetening agent includes sucralose, present in 6.0±1.5 wt. % of the oral soluble film.

In specific embodiments, the sweetening agent includes sucralose, present in 6.0±1.0 wt. % of the oral soluble film.

In specific embodiments, the sweetening agent includes sucralose, present in 6.0±0.5 wt. % of the oral soluble film.

In specific embodiments, the sweetening agent includes sucralose, present in 5.71±2.5 wt. % of the oral soluble film, based on a 5±1.5 wt. % hydrated film.

In specific embodiments, the sweetening agent includes sucralose, present in 5.71±2 wt. % of the oral soluble film, based on a 5±1.5 wt. % hydrated film.

In specific embodiments, the sweetening agent includes sucralose, present in 5.71±1.5 wt. % of the oral soluble film, based on a 5±1.5 wt. % hydrated film.

In specific embodiments, the sweetening agent includes sucralose, present in 5.71±1.0 wt. % of the oral soluble film, based on a 5±1.5 wt. % hydrated film.

In specific embodiments, the sweetening agent includes sucralose, present in 5.71±0.5 wt. % of the oral soluble film, based on a 5±1.5 wt. % hydrated film.

In specific embodiments, the oral soluble film is configured as a unit dose and the sucralose is present in 11.7±3.0 mg.

In specific embodiments, the oral soluble film is configured as a unit dose and the sucralose is present in 11.7±2.5 mg.

In specific embodiments, the oral soluble film is configured as a unit dose and the sucralose is present in 11.7±2.0 mg.

In specific embodiments, the oral soluble film is configured as a unit dose and the sucralose is present in 11.7±1.5 mg.

In specific embodiments, the oral soluble film is configured as a unit dose and the sucralose is present in 11.7±0.5 mg.

In specific embodiments, the sweetening agent includes acesulfame potassium (ACE-K).

In specific embodiments, the sweetening agent includes acesulfame potassium (ACE-K), present in 4.00±1.5 wt. % of the oral soluble film.

In specific embodiments, the sweetening agent includes acesulfame potassium (ACE-K), present in 4.00±1.25 wt. % of the oral soluble film.

In specific embodiments, the sweetening agent includes acesulfame potassium (ACE-K), present in 4.00±1.0 wt. % of the oral soluble film.

In specific embodiments, the sweetening agent includes acesulfame potassium (ACE-K), present in 4.00±0.75 wt. % of the oral soluble film.

In specific embodiments, the sweetening agent includes acesulfame potassium (ACE-K), present in 4.00±0.5 wt. % of the oral soluble film.

In specific embodiments, the sweetening agent includes acesulfame potassium (ACE-K), present in 3.80±1.5 wt. % of the oral soluble film, based on a 5±1.5 wt. % hydrated film.

In specific embodiments, the sweetening agent includes acesulfame potassium (ACE-K), present in 3.80±1.25 wt. % of the oral soluble film, based on a 5±1.5 wt. % hydrated film.

In specific embodiments, the sweetening agent includes acesulfame potassium (ACE-K), present in 3.80±1.0 wt. % of the oral soluble film, based on a 5±1.5 wt. % hydrated film.

In specific embodiments, the sweetening agent includes acesulfame potassium (ACE-K), present in 3.80±0.75 wt. % of the oral soluble film, based on a 5±1.5 wt. % hydrated film.

In specific embodiments, the sweetening agent includes acesulfame potassium (ACE-K), present in 3.80±0.5 wt. % of the oral soluble film, based on a 5±1.5 wt. % hydrated film.

In specific embodiments, the oral soluble film is configured as a unit dose and the acesulfame potassium (ACE-K) is present in 7.80±2.5 mg.

In specific embodiments, the oral soluble film is configured as a unit dose and the acesulfame potassium (ACE-K) is present in 7.80±2.0 mg.

In specific embodiments, the oral soluble film is configured as a unit dose and the acesulfame potassium (ACE-K) is present in 7.80±1.5 mg.

In specific embodiments, the oral soluble film is configured as a unit dose and the acesulfame potassium (ACE-K) is present in 7.80±1.0 mg.

In specific embodiments, the oral soluble film is configured as a unit dose and the acesulfame potassium (ACE-K) is present in 7.80±0.5 mg.

In specific embodiments, the oral soluble film is obtained from a slurry wherein sweetening agent is present in 4.66±1.25 wt. % of the slurry.

In specific embodiments, the oral soluble film is obtained from a slurry wherein sweetening agent is present in 4.66±1 wt. % of the slurry.

In specific embodiments, the oral soluble film is obtained from a slurry wherein sweetening agent is present in 4.66±0.75 wt. % of the slurry.

In specific embodiments, the oral soluble film is obtained from a slurry wherein sweetening agent is present in 4.66±0.5 wt. % of the slurry.

In specific embodiments, the oral soluble film is obtained from a slurry wherein sweetening agent is present in 4.66±0.25 wt. % of the slurry.

In specific embodiments, the oral soluble film is obtained from a slurry wherein sweetening agent is present in 4.66±0.1 wt. % of the slurry.

In specific embodiments, the oral soluble film is obtained from a slurry wherein sucralose is present in 2.8±0.75 wt. % of the slurry.

In specific embodiments, the oral soluble film is obtained from a slurry wherein sucralose is present in 2.8±0.5 wt. % of the slurry.

In specific embodiments, the oral soluble film is obtained from a slurry wherein sucralose is present in 2.8±0.25 wt. % of the slurry.

In specific embodiments, the oral soluble film is obtained from a slurry wherein sucralose is present in 2.8±0.15 wt. % of the slurry.

In specific embodiments, the oral soluble film is obtained from a slurry wherein sucralose is present in 2.8±0.1 wt. % of the slurry.

In specific embodiments, the oral soluble film is obtained from a slurry wherein acesulfame potassium (ACE-K) is present in 1.86±0.75 wt. % of the slurry.

In specific embodiments, the oral soluble film is obtained from a slurry wherein acesulfame potassium (ACE-K) is present in 1.86±0.5 wt. % of the slurry.

In specific embodiments, the oral soluble film is obtained from a slurry wherein acesulfame potassium (ACE-K) is present in 1.86±0.4 wt. % of the slurry.

In specific embodiments, the oral soluble film is obtained from a slurry wherein acesulfame potassium (ACE-K) is present in 1.86±0.3 wt. % of the slurry.

In specific embodiments, the oral soluble film is obtained from a slurry wherein acesulfame potassium (ACE-K) is present in 1.86±0.2 wt. % of the slurry.

In specific embodiments, the oral soluble film is obtained from a slurry wherein acesulfame potassium (ACE-K) is present in 1.86±0.1 wt. % of the slurry.

Coloring Agent

In specific embodiments, the coloring agent is absent.

In specific embodiments, the coloring agent is present.

In specific embodiments, the coloring agent is present in 0.01±0.005 wt. % of the oral soluble film.

In specific embodiments, the coloring agent is present in 0.01±0.004 wt. % of the oral soluble film.

In specific embodiments, the coloring agent is present in 0.01±0.003 wt. % of the oral soluble film.

In specific embodiments, the coloring agent is present in 0.01±0.002 wt. % of the oral soluble film.

In specific embodiments, the coloring agent is present in 0.01±0.001 wt. % of the oral soluble film.

In specific embodiments, the oral soluble film is configured as a unit dose and the coloring agent is present in 0.02±0.007 mg.

In specific embodiments, the oral soluble film is configured as a unit dose and the coloring agent is present in 0.02±0.006 mg.

In specific embodiments, the oral soluble film is configured as a unit dose and the coloring agent is present in 0.02±0.005 mg.

In specific embodiments, the oral soluble film is configured as a unit dose and the coloring agent is present in 0.02±0.004 mg.

In specific embodiments, the oral soluble film is configured as a unit dose and the coloring agent is present in 0.02±0.003 mg.

In specific embodiments, the oral soluble film is obtained from a slurry wherein the coloring agent is present in 0.005±0.001 wt. % of the slurry.

In specific embodiments, the oral soluble film is obtained from a slurry wherein the coloring agent is present in 0.005±0.0007 wt. % of the slurry.

In specific embodiments, the oral soluble film is obtained from a slurry wherein the coloring agent is present in 0.005±0.0005 wt. % of the slurry.

In specific embodiments, the oral soluble film is obtained from a slurry wherein the coloring agent is present in 0.005±0.0003 wt. % of the slurry.

In specific embodiments, the oral soluble film is obtained from a slurry wherein the coloring agent is present in 0.005±0.0001 wt. % of the slurry.

In specific embodiments, the coloring agent includes at least one FD&C color.

In specific embodiments, the coloring agent includes FD&C Blue.

In specific embodiments, the coloring agent includes FD&C Blue 1.

In specific embodiments, the FD&C Blue 1 is present in 0.01±0.005 wt. % of the oral soluble film.

In specific embodiments, the FD&C Blue 1 is present in 0.01±0.004 wt. % of the oral soluble film.

In specific embodiments, the FD&C Blue 1 is present in 0.01±0.003 wt. % of the oral soluble film.

In specific embodiments, the FD&C Blue 1 is present in 0.01±0.002 wt. % of the oral soluble film.

In specific embodiments, the FD&C Blue 1 is present in 0.01±0.001 wt. % of the oral soluble film.

In specific embodiments, the oral soluble film is configured as a unit dose and the FD&C Blue 1 is present in 0.02±0.007 mg.

In specific embodiments, the oral soluble film is configured as a unit dose and the FD&C Blue 1 is present in 0.02±0.006 mg.

In specific embodiments, the oral soluble film is configured as a unit dose and the FD&C Blue 1 is present in 0.02±0.005 mg.

In specific embodiments, the oral soluble film is configured as a unit dose and the FD&C Blue 1 is present in 0.02±0.004 mg.

In specific embodiments, the oral soluble film is configured as a unit dose and the FD&C Blue 1 is present in 0.02±0.003 mg.

In specific embodiments, the oral soluble film is obtained from a slurry wherein the FD&C Blue 1 is present in 0.005±0.001 wt. % of the slurry.

In specific embodiments, the oral soluble film is obtained from a slurry wherein the FD&C Blue 1 is present in 0.005±0.0007 wt. % of the slurry.

In specific embodiments, the oral soluble film is obtained from a slurry wherein the FD&C Blue 1 is present in 0.005±0.0005 wt. % of the slurry.

In specific embodiments, the oral soluble film is obtained from a slurry wherein the FD&C Blue 1 is present in 0.005±0.0003 wt. % of the slurry.

In specific embodiments, the oral soluble film is obtained from a slurry wherein the FD&C Blue 1 is present in 0.005±0.0001 wt. % of the slurry.

Preservative

In specific embodiments, the preservative is present in 0.10±0.06 wt. % of the oral soluble film.

In specific embodiments, the preservative is present in 0.10±0.05 wt. % of the oral soluble film.

In specific embodiments, the preservative is present in 0.10±0.04 wt. % of the oral soluble film.

In specific embodiments, the preservative is present in 0.10±0.03 wt. % of the oral soluble film.

In specific embodiments, the preservative is present in 0.10±0.02 wt. % of the oral soluble film.

In specific embodiments, the preservative is present in 0.10±0.01 wt. % of the oral soluble film. In specific embodiments, the oral soluble film is configured as a unit dose and the preservative is present in 0.20±0.08 mg.

In specific embodiments, the oral soluble film is configured as a unit dose and the preservative is present in 0.20±0.07 mg.

In specific embodiments, the oral soluble film is configured as a unit dose and the preservative is present in 0.20±0.06 mg.

In specific embodiments, the oral soluble film is configured as a unit dose and the preservative is present in 0.20±0.05 mg.

In specific embodiments, the oral soluble film is configured as a unit dose and the preservative is present in 0.20±0.04 mg.

In specific embodiments, the oral soluble film is configured as a unit dose and the preservative is present in 0.20±0.03 mg.

In specific embodiments, the oral soluble film is configured as a unit dose and the preservative is present in 0.20±0.02 mg.

In specific embodiments, the oral soluble film is configured as a unit dose and the preservative is present in 0.20±0.01 mg.

In specific embodiments, the oral soluble film is obtained from a slurry wherein the preservative is present in 0.05±0.01 wt. % of the slurry.

In specific embodiments, the oral soluble film is obtained from a slurry wherein the preservative is present in 0.05±0.007 wt. % of the slurry.

In specific embodiments, the oral soluble film is obtained from a slurry wherein the preservative is present in 0.05±0.005 wt. % of the slurry.

In specific embodiments, the oral soluble film is obtained from a slurry wherein the preservative is present in 0.05±0.003 wt. % of the slurry.

In specific embodiments, the oral soluble film is obtained from a slurry wherein the preservative is present in 0.05±0.001 wt. % of the slurry.

In specific embodiments, the preservative includes sodium benzoate.

In specific embodiments, the sodium benzoate is present in 0.10±0.06 wt. % of the oral soluble film.

In specific embodiments, the sodium benzoate is present in 0.10±0.05 wt. % of the oral soluble film.

In specific embodiments, the sodium benzoate is present in 0.10±0.04 wt. % of the oral soluble film.

In specific embodiments, the sodium benzoate is present in 0.10±0.03 wt. % of the oral soluble film.

In specific embodiments, the sodium benzoate is present in 0.10±0.02 wt. % of the oral soluble film.

In specific embodiments, the sodium benzoate is present in 0.10±0.01 wt. % of the oral soluble film.

In specific embodiments, the oral soluble film is configured as a unit dose and the sodium benzoate is present in 0.20±0.08 mg.

In specific embodiments, the oral soluble film is configured as a unit dose and the sodium benzoate is present in 0.20±0.07 mg.

In specific embodiments, the oral soluble film is configured as a unit dose and the sodium benzoate is present in 0.20±0.06 mg.

In specific embodiments, the oral soluble film is configured as a unit dose and the sodium benzoate is present in 0.20±0.05 mg.

In specific embodiments, the oral soluble film is configured as a unit dose and the sodium benzoate is present in 0.20±0.04 mg.

In specific embodiments, the oral soluble film is configured as a unit dose and the sodium benzoate is present in 0.20±0.03 mg.

In specific embodiments, the oral soluble film is configured as a unit dose and the sodium benzoate is present in 0.20±0.02 mg.

In specific embodiments, the oral soluble film is configured as a unit dose and the sodium benzoate is present in 0.20±0.01 mg.

In specific embodiments, the oral soluble film is obtained from a slurry wherein the sodium benzoate is present in 0.05±0.01 wt. % of the slurry.

In specific embodiments, the oral soluble film is obtained from a slurry wherein the sodium benzoate is present in 0.05±0.007 wt. % of the slurry.

In specific embodiments, the oral soluble film is obtained from a slurry wherein the sodium benzoate is present in 0.05±0.005 wt. % of the slurry.

In specific embodiments, the oral soluble film is obtained from a slurry wherein the sodium benzoate is present in 0.05±0.003 wt. % of the slurry.

In specific embodiments, the oral soluble film is obtained from a slurry wherein the sodium benzoate is present in 0.05±0.001 wt. % of the slurry.

Solvent

In specific embodiments, the solvent includes water.

In specific embodiments, the water content of the hydrated oral soluble film is 4.5±2 wt. %.

In specific embodiments, the water content of the hydrated oral soluble film is 4.5±1.5 wt. %.

In specific embodiments, the water content of the hydrated oral soluble film is 4.5±1 wt. %.

In specific embodiments, the water content of the hydrated oral soluble film is 4.5±0.5 wt. %.

In specific embodiments, the water content of the hydrated oral soluble film is 4.5±0.25 wt. %.

In specific embodiments, the water content of the hydrated oral soluble film is 4±2 wt. %.

In specific embodiments, the water content of the hydrated oral soluble film is 4±1.5 wt. %.

In specific embodiments, the water content of the hydrated oral soluble film is 4±1 wt. %.

In specific embodiments, the water content of the hydrated oral soluble film is 4±0.5 wt. %.

In specific embodiments, the water content of the hydrated oral soluble film is 4±0.25 wt. %.

In specific embodiments, the oral soluble film is configured as a unit dose and the water is present in 9.76±4 mg.

In specific embodiments, the oral soluble film is configured as a unit dose and the water is present in 9.76±3 mg.

In specific embodiments, the oral soluble film is configured as a unit dose and the water is present in 9.76±2.25 mg.

In specific embodiments, the oral soluble film is configured as a unit dose and the water is present in 9.76±2 mg.

In specific embodiments, the oral soluble film is configured as a unit dose and the water is present in 9.76±1.5 mg.

In specific embodiments, the oral soluble film is obtained from a slurry wherein the water is present in 53.3±12 wt. % of the slurry.

In specific embodiments, the oral soluble film is obtained from a slurry wherein the water is present in 53.3±11 wt. % of the slurry.

In specific embodiments, the oral soluble film is obtained from a slurry wherein the water is present in 53.3±10 wt. % of the slurry.

In specific embodiments, the oral soluble film is obtained from a slurry wherein the water is present in 53.3±9 wt. % of the slurry.

In specific embodiments, the oral soluble film is obtained from a slurry wherein the water is present in 53.3±7 wt. % of the slurry.

In specific embodiments, the oral soluble film is obtained from a slurry wherein the water is present in 53.3±5 wt. % of the slurry.

In specific embodiments, the oral soluble film is obtained from a slurry wherein the water is present in 53.3±3 wt. % of the slurry.

In specific embodiments, the oral soluble film is obtained from a slurry wherein the water is present in 53.3±1 wt. % of the slurry.

Additional Excipients

In specific embodiments, the oral soluble film is essentially free of a saliva stimulating agent, release modifier, adjuvant, fragrant, surfactant, pH adjusting agent, buffering agent, stabilizer, and antioxidant.

In specific embodiments, the oral soluble film is essentially free of a saliva stimulating agent.

In specific embodiments, the oral soluble film is essentially free of a release modifier.

In specific embodiments, the oral soluble film is essentially free of an adjuvant.

In specific embodiments, the oral soluble film is essentially free of a fragrant.

In specific embodiments, the oral soluble film is essentially free of a surfactant.

In specific embodiments, the oral soluble film is essentially free of a pH adjusting agent.

In specific embodiments, the oral soluble film is essentially free of a buffering agent.

In specific embodiments, the oral soluble film is essentially free of a stabilizer.

In specific embodiments, the oral soluble film is essentially free of an antioxidant.

In specific embodiments, the oral soluble film further includes at least one of a saliva stimulating agent, release modifier, adjuvant, fragrant, surfactant, pH adjusting agent, buffering agent, stabilizer, and antioxidant.

In specific embodiments, the oral soluble film further includes a saliva stimulating agent.

In specific embodiments, the oral soluble film further includes a release modifier.

In specific embodiments, the oral soluble film further includes an adjuvant.

In specific embodiments, the oral soluble film further includes a fragrant.

In specific embodiments, the oral soluble film further includes a surfactant.

In specific embodiments, the oral soluble film further includes a pH adjusting agent.

In specific embodiments, the oral soluble film further includes a buffering agent.

In specific embodiments, the oral soluble film further includes a stabilizer.

In specific embodiments, the oral soluble film further includes an antioxidant.

In specific embodiments, the oral soluble film further includes pharmaceutically acceptable ink.

In specific embodiments, the oral soluble film further includes pharmaceutically acceptable ink, used to print a logo or indicia thereon.

In specific embodiments, the oral soluble film further includes pharmaceutically acceptable ink, present in up to 0.10 wt. % of the oral soluble film.

In specific embodiments, the oral soluble film further includes pharmaceutically acceptable ink, present in up to 0.05 wt. % of the oral soluble film.

In specific embodiments, the oral soluble film further includes pharmaceutically acceptable ink, present in up to 0.01 wt. % of the oral soluble film.

Physical and Performance Characteristics

In specific embodiments, the oral soluble film is an anhydrous film.

In specific embodiments, the oral soluble film is a 5±1.5 wt. % hydrated film.

In specific embodiments, the oral soluble film is a 5±1.25 wt. % hydrated film.

In specific embodiments, the oral soluble film is a 5±1.1 wt. % hydrated film.

In specific embodiments, the oral soluble film is a 5±1 wt. % hydrated film.

In specific embodiments, the oral soluble film is a 5±0.85 wt. % hydrated film.

In specific embodiments, the oral soluble film is a 5±0.75 wt. % hydrated film.

In specific embodiments, the oral soluble film is a 5±0.5 wt. % hydrated film.

In specific embodiments, the oral soluble film is a 5±0.25 wt. % hydrated film.

In specific embodiments, the oral soluble film is a 5 wt. % hydrated film.

In specific embodiments, the oral soluble film is configured as a unit dose having a mass of 195.1±25 mg.

In specific embodiments, the oral soluble film is configured as a unit dose having a mass of 195.1±20 mg.

In specific embodiments, the oral soluble film is configured as a unit dose having a mass of 195.1±15 mg.

In specific embodiments, the oral soluble film is configured as a unit dose having a mass of 195.1±10 mg.

In specific embodiments, the oral soluble film is configured as a unit dose having a mass of 195.1±5 mg.

In specific embodiments, the oral soluble film is configured as a unit dose having a mass of 204.9±25 mg, based on a 5±1.5 wt. % hydrated film.

In specific embodiments, the oral soluble film is configured as a unit dose having a mass of 204.9±20 mg, based on a 5±1.5 wt. % hydrated film.

In specific embodiments, the oral soluble film is configured as a unit dose having a mass of 204.9±15 mg, based on a 5±1.5 wt. % hydrated film.

In specific embodiments, the oral soluble film is configured as a unit dose having a mass of 204.9±10 mg, based on a 5±1.5 wt. % hydrated film.

In specific embodiments, the oral soluble film is configured as a unit dose having a mass of 204.9±5 mg, based on a 5±1.5 wt. % hydrated film.

In specific embodiments, the oral soluble film dissolves within 90 seconds upon contact with an oral mucosal surface.

In specific embodiments, the oral soluble film dissolves within 75 seconds upon contact with an oral mucosal surface.

In specific embodiments, the oral soluble film dissolves within 60 seconds upon contact with an oral mucosal surface.

In specific embodiments, the oral soluble film dissolves within 45 seconds upon contact with an oral mucosal surface.

In specific embodiments, the oral soluble film dissolves within 30 seconds upon contact with an oral mucosal surface.

In specific embodiments, the oral soluble film dissolves within 20 seconds upon contact with an oral mucosal surface.

In specific embodiments, the oral soluble film dissolves in 5-90 seconds upon contact with an oral mucosal surface.

In specific embodiments, the oral soluble film dissolves in 10-90 seconds upon contact with an oral mucosal surface.

In specific embodiments, the oral soluble film dissolves in 15-90 seconds upon contact with an oral mucosal surface.

In specific embodiments, the oral soluble film dissolves in 5-75 seconds upon contact with an oral mucosal surface.

In specific embodiments, the oral soluble film dissolves in 10-75 seconds upon contact with an oral mucosal surface.

In specific embodiments, the oral soluble film dissolves in 15-75 seconds upon contact with an oral mucosal surface.

In specific embodiments, the oral soluble film dissolves in 5-60 seconds upon contact with an oral mucosal surface.

In specific embodiments, the oral soluble film dissolves in 10-60 seconds upon contact with an oral mucosal surface.

In specific embodiments, the oral soluble film dissolves in 15-60 seconds upon contact with an oral mucosal surface.

In specific embodiments, the oral soluble film dissolves in 20-60 seconds upon contact with an oral mucosal surface.

In specific embodiments, the oral soluble film dissolves in 5-45 seconds upon contact with an oral mucosal surface.

In specific embodiments, the oral soluble film dissolves in 10-45 seconds upon contact with an oral mucosal surface.

In specific embodiments, the oral soluble film dissolves in 15-45 seconds upon contact with an oral mucosal surface.

In specific embodiments, the oral soluble film has a breaking strength of 8-12 N.

In specific embodiments, the oral soluble film has a breaking strength of 10±3 N.

In specific embodiments, the oral soluble film has a breaking strength of 10±2 N.

In specific embodiments, the oral soluble film has a breaking strength of 10±1 N.

In specific embodiments, the oral soluble film has an elongation strength of 2-4 mm.

In specific embodiments, the oral soluble film has an elongation strength of 3±1 mm.

In specific embodiments, the oral soluble film has an elongation strength of 3±0.5 mm.

In specific embodiments, the oral soluble film has a pH of 3.8-4.7.

In specific embodiments, the oral soluble film has a pH of 4.0-4.5.

In specific embodiments, the oral soluble film has a pH of 4.1-4.4.

In specific embodiments, the oral soluble film has a density of 0.006-0.009 $g/cm^3$.

In specific embodiments, the oral soluble film has a density of 0.0065-0.0085 $g/cm^3$.

In specific embodiments, the oral soluble film has a density of 0.007±0.0012 $g/cm^3$.

In specific embodiments, the oral soluble film has a density of 0.007±0.1 $g/cm^3$.

In specific embodiments, the oral soluble film has a density of 0.007±0.0008 $g/cm^3$.

In specific embodiments, the oral soluble film has a density of 0.007±0.0006 $g/cm^3$.

In specific embodiments, the oral soluble film has a loss on drying (LOD) of 7±5 wt. %.

In specific embodiments, the oral soluble film has a loss on drying (LOD) of 7±4 wt. %.

In specific embodiments, the oral soluble film has a loss on drying (LOD) of 7±3 wt. %.

In specific embodiments, the oral soluble film has a loss on drying (LOD) of 7±2 wt. %.

In specific embodiments, the oral soluble film has a loss on drying (LOD) of 7±1 wt. %.

In specific embodiments, the oral soluble film has a loss on drying (LOD) of 5±3 wt. %.

In specific embodiments, the oral soluble film has a loss on drying (LOD) of 5±2 wt. %.

In specific embodiments, the oral soluble film has a loss on drying (LOD) of 5±1 wt. %.

In specific embodiments, the oral soluble film has a loss on drying (LOD) of 3.5±1.5 wt. %.

In specific embodiments, the oral soluble film has a loss on drying (LOD) of 3.5±1.25 wt. %.

In specific embodiments, the oral soluble film has a loss on drying (LOD) of 3.5±1 wt. %.

In specific embodiments, the oral soluble film has a loss on drying (LOD) of 3.5±0.75 wt. %.

In specific embodiments, the oral soluble film has a loss on drying (LOD) of 3.5±0.5 wt. %.

In specific embodiments, the oral soluble film has a loss on drying (LOD) of 3.5±0.25 wt. %.

In specific embodiments, the oral soluble film has a loss on drying (LOD) of less than 5 wt. %.

In specific embodiments, the oral soluble film has a loss on drying (LOD) of less than 4 wt. %.

In specific embodiments, the oral soluble film has a loss on drying (LOD) of less than 3 wt. %.

In specific embodiments, the oral soluble film is formed from a slurry having a density of 0.60-0.90 g/cm$^3$.

In specific embodiments, the oral soluble film is formed from a slurry having a density of 0.65-0.85 g/cm$^3$.

In specific embodiments, the oral soluble film is formed from a slurry having a density of 0.725±0.12 g/cm$^3$.

In specific embodiments, the oral soluble film is formed from a slurry having a density of 0.725±0.10 g/cm$^3$.

In specific embodiments, the oral soluble film is formed from a slurry having a density of 0.725±0.08 g/cm$^3$.

In specific embodiments, the oral soluble film is formed from a slurry having a density of 0.725±0.06 g/cm$^3$.

In specific embodiments, the oral soluble film is formed from a slurry having a density of 0.725±0.05 g/cm$^3$.

In specific embodiments, oral soluble film is formed from a slurry having a viscosity at 22-30° Celsius of 6,000±1,500 centipoise (cP).

In specific embodiments, oral soluble film is formed from a slurry having a viscosity at 22-30° Celsius of 6,000±1,250 centipoise (cP).

In specific embodiments, oral soluble film is formed from a slurry having a viscosity at 22-30° Celsius of 6,000±1,000 centipoise (cP).

In specific embodiments, oral soluble film is formed from a slurry having a viscosity at 22-30° Celsius of 6,000±750 centipoise (cP).

In specific embodiments, oral soluble film is formed from a slurry having a viscosity at 22-30° Celsius of 6,000±500 centipoise (cP).

In specific embodiments, oral soluble film is formed from a slurry having a viscosity at 22-30° Celsius of 6,000±250 centipoise (cP).

In specific embodiments, oral soluble film is formed from a slurry having a viscosity at 22-30° Celsius of 6,000±100 centipoise (cP).

In specific embodiments, the oral soluble film has a dissolution (USP apparatus: 1 (basket); media: 0.01 N HCl; volume: 900-ml; temperature: 37±0.5° C.; RPM: 100; sampling: 5, 10, 15, 30, 45, 60 min) of at least 90 wt. % at 5 minutes.

In specific embodiments, the oral soluble film has a dissolution (USP apparatus: 1 (basket); media: 0.01 N HCl; volume: 900-ml; temperature: 37±0.5° C.; RPM: 100; sampling: 5, 10, 15, 30, 45, 60 min) of at least 95 wt. % release at 5 minutes.

In specific embodiments, the oral soluble film has a dissolution (USP apparatus: 1 (basket); media: 0.01 N HCl; volume: 900-ml; temperature: 37±0.5° C.; RPM: 100; sampling: 5, 10, 15, 30, 45, 60 min) of (i) at least 90 wt. % at 5 minutes and (ii) 100 wt. % release at 10 minutes.

In specific embodiments, the oral soluble film has a dissolution (USP apparatus: 1 (basket); media: 0.01 N HCl; volume: 900-ml; temperature: 37±0.5° C.; RPM: 100; sampling: 5, 10, 15, 30, 45, 60 min) of (i) at least 95 wt. % release at 5 minutes and (ii) 100 wt. % release at 10 minutes.

In specific embodiments, the oral soluble film is mucoadhesive, such that upon oral administration, the oral soluble film adheres to a surface of the oral cavity.

In specific embodiments, the oral soluble film is configured as individual unit doses.

In specific embodiments, the oral soluble film is configured as a bulk roll.

In specific embodiments, the oral soluble film is configured as a self-supporting film-dosage form.

In specific embodiments, the oral soluble film is configured as a unit dose.

In specific embodiments, the oral soluble film is configured in an unwound form.

In specific embodiments, the oral soluble film is configured as a sheet.

In specific embodiments, the oral soluble film is cut from a self-supporting film.

In specific embodiments, the oral soluble film is configured in a wound form.

In specific embodiments, the oral soluble film is configured as a bulk roll.

In specific embodiments, the oral soluble film is a monolayer film.

In specific embodiments, the oral soluble film is configured as a unit dose having the dimensions 22±3×38±4×0.35±0.06 mm.

In specific embodiments, the oral soluble film is configured as a unit dose having the dimensions 22±3×19±2×0.35±0.06 mm.

In specific embodiments, the oral soluble film is configured as a unit dose having a width of 22±4 mm.

In specific embodiments, the oral soluble film is configured as a unit dose having a width of 22±3 mm.

In specific embodiments, the oral soluble film is configured as a unit dose having a width of 22±2 mm.

In specific embodiments, the oral soluble film is configured as a unit dose having a width of 22±1 mm.

In specific embodiments, the oral soluble film is configured as a unit dose having a width of 22 mm.

In specific embodiments, the oral soluble film is configured as a unit dose having a length of 38±5 mm.

In specific embodiments, the oral soluble film is configured as a unit dose having a length of 38±4 mm.

In specific embodiments, the oral soluble film is configured as a unit dose having a length of 38±3 mm.

In specific embodiments, the oral soluble film is configured as a unit dose having a length of 38±2 mm.

In specific embodiments, the oral soluble film is configured as a unit dose having a length of 38±1 mm.

In specific embodiments, the oral soluble film is configured as a unit dose having a length of 38 mm.

In specific embodiments, the oral soluble film is configured as a unit dose having a length of 19±5 mm.

In specific embodiments, the oral soluble film is configured as a unit dose having a length of 19±4 mm.

In specific embodiments, the oral soluble film is configured as a unit dose having a length of 19±3 mm.

In specific embodiments, the oral soluble film is configured as a unit dose having a length of 19±2 mm.

In specific embodiments, the oral soluble film is configured as a unit dose having a length of 19±1 mm.

In specific embodiments, the oral soluble film is configured as a unit dose having a length of 19 mm.

In specific embodiments, the oral soluble film has a thickness of 0.40±0.05 mm.

In specific embodiments, the oral soluble film has a thickness of 0.40±0.04 mm.

In specific embodiments, the oral soluble film has a thickness of 0.40±0.03 mm.

In specific embodiments, the oral soluble film has a thickness of 0.40±0.02 mm.

In specific embodiments, the oral soluble film has a thickness of 0.40±0.01 mm.

In specific embodiments, the oral soluble film has a thickness of 0.40 mm.

In specific embodiments, the oral soluble film has a thickness of 0.35±0.07 mm.

In specific embodiments, the oral soluble film has a thickness of 0.35±0.06 mm.

In specific embodiments, the oral soluble film has a thickness of 0.35±0.05 mm.

In specific embodiments, the oral soluble film has a thickness of 0.35±0.04 mm.

In specific embodiments, the oral soluble film has a thickness of 0.35±0.03 mm.

In specific embodiments, the oral soluble film has a thickness of 0.35±0.02 mm.

In specific embodiments, the oral soluble film has a thickness of 0.35±0.01 mm.

In specific embodiments, the oral soluble film has a thickness of 0.35 mm.

In specific embodiments, the oral soluble film is configured as a unit dose having a surface area of 836±175 mm$^2$.

In specific embodiments, the oral soluble film is configured as a unit dose having a surface area of 836±150 mm$^2$.

In specific embodiments, the oral soluble film is configured as a unit dose having a surface area of 836±125 mm$^2$.

In specific embodiments, the oral soluble film is configured as a unit dose having a surface area of 836±100 mm$^2$.

In specific embodiments, the oral soluble film is configured as a unit dose having a surface area of 836±75 mm$^2$.

In specific embodiments, the oral soluble film is configured as a unit dose having a surface area of 836±50 mm$^2$.

In specific embodiments, the oral soluble film is configured as a unit dose having a surface area of 836±25 mm$^2$.

In specific embodiments, the oral soluble film is configured as a unit dose having a surface area of 836±10 mm$^2$.

In specific embodiments, the oral soluble film is configured as a unit dose having a surface area of 836±5 mm$^2$.

In specific embodiments, the oral soluble film is configured as a unit dose having a surface area of 836 mm.

In specific embodiments, the oral soluble film is configured as a unit dose having a surface area of 418±75 mm$^2$.

In specific embodiments, the oral soluble film is configured as a unit dose having a surface area of 418±50 mm$^2$.

In specific embodiments, the oral soluble film is configured as a unit dose having a surface area of 418±25 mm$^2$.

In specific embodiments, the oral soluble film is configured as a unit dose having a surface area of 418±10 mm$^2$.

In specific embodiments, the oral soluble film is configured as a unit dose having a surface area of 418±5 mm$^2$.

In specific embodiments, the oral soluble film is configured as a unit dose having a surface area of 418 mm$^2$.

In specific embodiments, the oral soluble film is configured as a unit dose having a volume of 292.6±60 mm$^3$.

In specific embodiments, the oral soluble film is configured as a unit dose having a volume of 292.6±50 mm$^3$.

In specific embodiments, the oral soluble film is configured as a unit dose having a volume of 292.6±40 mm$^3$.

In specific embodiments, the oral soluble film is configured as a unit dose having a volume of 292.6±30 mm$^3$.

In specific embodiments, the oral soluble film is configured as a unit dose having a volume of 292.6±20 mm$^3$.

In specific embodiments, the oral soluble film is configured as a unit dose having a volume of 292.6±10 mm$^3$.

In specific embodiments, the oral soluble film is configured as a unit dose having a volume of 292.6±5 mm$^3$.

In specific embodiments, the oral soluble film is configured as a unit dose having a volume of 143.3±30 mm$^3$.

In specific embodiments, the oral soluble film is configured as a unit dose having a volume of 143.3±25 mm$^3$.

In specific embodiments, the oral soluble film is configured as a unit dose having a volume of 143.3±20 mm$^3$.

In specific embodiments, the oral soluble film is configured as a unit dose having a volume of 143.3±15 mm$^3$.

In specific embodiments, the oral soluble film is configured as a unit dose having a volume of 143.3±10 mm$^3$.

In specific embodiments, the oral soluble film is configured as a unit dose having a volume of 143.3±5 mm$^3$.

In specific embodiments, the oral soluble film exhibits a high stability, such that at least 90 wt. % of the sildenafil citrate remains in the oral dissolvable film, under stability conditions of 25±2° C., relative humidity (RH) 60±5%, over a period of time of ≥6 months.

In specific embodiments, the oral soluble film exhibits a high stability, such that at least 92.5 wt. % of the sildenafil citrate remains in the oral dissolvable film, under stability conditions of 25±2° C., relative humidity (RH) 60±5%, over a period of time of ≥6 months.

In specific embodiments, the oral soluble film exhibits a high stability, such that at least 95 wt. % of the sildenafil citrate remains in the oral dissolvable film, under stability conditions of 25±2° C., relative humidity (RH) 60±5%, over a period of time of ≥6 months.

In specific embodiments, the oral soluble film exhibits a high stability, such that at least 97.5 wt. % of the sildenafil citrate remains in the oral dissolvable film, under stability conditions of 25±2° C., relative humidity (RH) 60±5%, over a period of time of ≥6 months.

In specific embodiments, the oral soluble film exhibits a high stability, such that at least 90 wt. % of the sildenafil citrate remains in the oral dissolvable film, under accelerated stability conditions of 40±2° C., relative humidity (RH) 75±5%, over a period of time of ≥6 months.

In specific embodiments, the oral soluble film exhibits a high stability, such that at least 92.5 wt. % of the sildenafil citrate remains in the oral dissolvable film, under accelerated stability conditions of 40±2° C., relative humidity (RH) 75±5%, over a period of time of ≥6 months.

In specific embodiments, the oral soluble film exhibits a high stability, such that at least 95 wt. % of the sildenafil citrate remains in the oral dissolvable film, under accelerated stability conditions of 40±2° C., relative humidity (RH) 75±5%, over a period of time of ≥6 months.

In specific embodiments, the oral soluble film exhibits a high stability, such that at least 97.5 wt. % of the sildenafil citrate remains in the oral dissolvable film, under accelerated stability conditions of 40±2° C., relative humidity (RH) 75±5%, over a period of time of ≥6 months.

In specific embodiments, relative to an oral tablet having an equivalent amount of sildenafil citrate (e.g., Viagra®), administration of the oral soluble film provides 100±20% absorption of sildenafil citrate.

In specific embodiments, relative to an oral tablet having an equivalent amount of sildenafil citrate (e.g., Viagra®), administration of the oral soluble film provides 100±15% absorption of sildenafil citrate.

In specific embodiments, relative to an oral tablet having an equivalent amount of sildenafil citrate (e.g., Viagra®), administration of the oral soluble film provides 100±10% absorption of sildenafil citrate.

In specific embodiments, relative to an oral tablet having an equivalent amount of sildenafil citrate (e.g., Viagra®), administration of the oral soluble film results in a lower incidence, severity, and/or duration of adverse reactions, including any one or more of headache, flushing, dyspepsia, abnormal vision, nasal congestion, back pain, myalgia, nausea, dizziness, and rash.

In specific embodiments, relative to an oral tablet having an equivalent amount of sildenafil citrate (e.g., Viagra®), administration of the oral soluble film results in a lower incidence, severity, and/or duration of adverse reactions, including each of headache, flushing, dyspepsia, abnormal vision, nasal congestion, back pain, myalgia, nausea, dizziness, and rash.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes the following:

| PK parameter | Amount of sildenafil citrate equivalent to 50 mg of sildenafil |
|---|---|
| $C_{MAX}$ (ng/mL) | 396.227 ± 105.035 |
| $AUC_{0 \to t}$ (hr * ng/mL) | 1,426.893 ± 520.565 |
| $AUC_{0 \to inf}$ (hr * ng/mL) | 1,524.433 ± 592.798 |
| $T_{MAX}$ (hr) | 1.088 ± 0.466 |
| $T_{1/2}$ (hr) | 3.783 ± 1.769 |
| $K_{EL}$ (1/hr) | 0.211 ± 0.068 |

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $C_{MAX}$ (ng/mL) of 396.227±79.245.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $C_{MAX}$ (ng/mL) of 396.227.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $AUC_{0 \to t}$ (hr*ng/mL) of 1,426.893±285.379.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $AUC_{0 \to t}$ (hr*ng/mL) of 1,426.893.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $AUC_{0 \to inf}$ (hr*ng/mL) of 1,524.433±304.889.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $AUC_{0 \to inf}$ (hr*ng/mL) of 1,524.433.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $T_{MAX}$ (hr) of 1.088±0.218.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $T_{MAX}$ (hr) of 1.088.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $T_{1/2}$ (hr) of 3.783±0.757.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $T_{1/2}$ (hr) of 3.783.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $K_{EL}$ (1/hr) of 0.211±0.042.

In specific embodiments, upon administration under fasted conditions with water, the oral soluble film (containing an amount of sildenafil citrate equivalent to 50 mg of sildenafil) exhibits a single-dose administration pharmacokinetic (PK) profile that includes a mean $K_{EL}$ (1/hr) of 0.211.

In specific embodiments, the active ingredient is selected in an amount, shown below.

| Active Ingredient | Indication & Usage | Amount of active ingredient in the oral soluble film | Oral tablets having an equivalent active ingredient |
|---|---|---|---|
| Sildenafil citrate | Treating ED | An amount equivalent to 50 mg of sildenafil | VIAGRA ® (sildenafil citrate) oral tablets |
| Sildenafil citrate | Treating PAH | An amount equivalent to 5 mg or 20 mg of sildenafil | RETAVIO ® (sildenafil citrate) oral tablets |

In specific embodiments, the oral soluble film is rectangular.

In specific embodiments, the oral soluble film includes a logo and/or printed indicia located thereon.

In specific embodiments, the oral soluble film the oral soluble film includes a logo and/or printed indicia located thereon that indicates the marketing company name, the manufacturing company name, the drug substance name, the drug product name, the strength, the dosage form, the route of administration, and/or the product serialization.

In specific embodiments, the oral soluble film includes a logo and/or indicia located thereon, printed with ink.

In specific embodiments, the oral soluble film includes a logo and/or indicia located thereon, that is embossed.

Packaging

In specific embodiments, a single dose of the oral soluble film is individually packaged and sealed.

In specific embodiments, a single dose of the oral soluble film is individually packaged and sealed with a primary packaging material.

In specific embodiments, a single dose of the oral soluble film is individually packaged and sealed with a primary packaging material, wherein the primary packaging material includes multiple layers.

In specific embodiments, a single dose of the oral soluble film is individually packaged and sealed with a primary packaging material, wherein the primary packaging material includes multiple layers and wherein at least one layer is manufactured from metalized polyester.

In specific embodiments, the primary packaging material forms a primary package that (i) protects the oral soluble film from light, (ii) protects the oral soluble film from microbial contamination, (iii) is child resistant, (iv) is a barrier to moisture and vapor, (v) identifies a logo and/or includes printed indicia, or (vi) any combination thereof.

In specific embodiments, the primary packaging material forms a primary package that protects the oral soluble film from light.

In specific embodiments, the primary packaging material forms a primary package that is airtight.

In specific embodiments, the primary packaging material forms a primary package that protects the oral soluble film from microbial contamination.

In specific embodiments, the primary packaging material forms a primary package that mitigates leachable(s) into the oral soluble film.

In specific embodiments, the primary packaging material forms a primary package that is child resistant.

In specific embodiments, the primary packaging material forms a primary package that forms a child resistant and closure system.

In specific embodiments, the primary packaging material forms a primary package that is a barrier to moisture and vapor.

In specific embodiments, the primary packaging material forms a primary package that identifies a logo and/or includes printed indicia.

In specific embodiments, the primary packaging material forms a primary package that identifies a logo and/or includes printed indicia instructing the subject how to open the primary package.

In specific embodiments, the primary packaging material forms a primary package that identifies a logo and/or includes printed indicia instructing the subject how to use the oral soluble film.

In specific embodiments, the primary packaging material forms a primary package that identifies product serialization.

In specific embodiments, the primary packaging material forms a primary package that identifies a logo of the marketing company.

In specific embodiments, the primary packaging material forms a primary package that identifies a logo of the manufacturing company.

In specific embodiments, the primary packaging material forms a primary package that identifies the drug product.

In specific embodiments, the primary packaging material forms a primary package that identifies the drug substance.

In specific embodiments, the primary packaging material forms a primary package that identifies the strength of the active ingredient.

In specific embodiments, the primary packaging material forms a primary package that identifies the route of administration.

In specific embodiments, the primary packaging material forms a primary package that identifies the dosage form.

In specific embodiments, the primary packaging material forms a primary package that identifies the route of administration.

In specific embodiments, the primary packaging material includes at least one of cellophane, polypropylene, nylon, polyester, vinylidene chloride, vinyl chloride, polycarbonate, low-density polyethylene, high-density polyethylene, linear low-density polyethylene, ionomer, polyvinyl alcohol, ethylene/vinyl acetate copolymer, ethylene/acrylic acid copolymer, ethylene/ethyl acrylate copolymer, polystyrene, and aluminum foil.

In specific embodiments, the primary packaging material includes metalized polyester.

In specific embodiments, a single layer of primary packaging material forms the primary package.

In specific embodiments, multiple layers of primary packaging material form the primary package.

In specific embodiments, multiple layers of primary packaging material form the primary package, wherein at least one layer includes metalized polyester.

In specific embodiments, multiple layers of primary packaging material form the primary package, wherein each layer is independently different from the other layers.

In specific embodiments, multiple layers of primary packaging material form the primary package, wherein any one layer is different from the other layers.

In specific embodiments, the kit includes an enclosure that contains a single dose of the oral soluble film, individually packaged and sealed with a primary packaging material.

In specific embodiments, the kit includes an enclosure that contains (a) a single dose of the oral soluble film, individually packaged and sealed with a primary packaging material, and (b) prescribing information.

In specific embodiments, the kit includes an enclosure that contains multiple doses of the oral soluble film, each individually packaged and sealed with a primary packaging material.

In specific embodiments, the kit includes an enclosure that contains (a) multiple doses of the oral soluble film, each individually packaged and sealed with a primary packaging material, and (b) prescribing information.

In specific embodiments, the enclosure is a box.

In specific embodiments, the enclosure is a bag.

Administration

In specific embodiments, the oral soluble film is administered to treat a disease or disorder ameliorated by sildenafil citrate.

In specific embodiments, the oral soluble film is administered to treat erectile dysfunction (ED) in a male subject.

In specific embodiments, the oral soluble film is administered to treat antidepressant-induced erectile dysfunction in a male subject.

In specific embodiments, the oral soluble film is administered to treat pulmonary arterial hypertension (PAH) in a subject.

In specific embodiments, the method of administration includes at least one of enteral delivery, transmucosal delivery, sublingual delivery, and buccal delivery, of the sildenafil citrate.

In specific embodiments, the method of administration includes enteral delivery of the sildenafil citrate.

In specific embodiments, the method of administration includes transmucosal delivery of the sildenafil citrate.

In specific embodiments, the method of administration includes sublingual delivery of the sildenafil citrate.

In specific embodiments, the method of administration includes buccal delivery of the sildenafil citrate.

In specific embodiments, the method of administration includes oral (P.O.) administration of the oral soluble film.

In specific embodiments, the oral soluble film is administered to a male subject up to 30 minutes before sexual activity.

In specific embodiments, the oral soluble film is administered to a male subject up to 20 minutes before sexual activity.

In specific embodiments, the oral soluble film is administered to a male subject up to 15 minutes before sexual activity.

In specific embodiments, the oral soluble film is administered to a male subject up to 10 minutes before sexual activity.

In specific embodiments, the oral soluble film is placed on the top of the tongue of a subject.

In specific embodiments, the oral soluble film is placed against the inside of the cheek of a subject.

In specific embodiments, the oral soluble film is placed between the cheek and gums of a subject.

In specific embodiments, the oral soluble film is orally administered to a subject in the absence of water or beverage.

In specific embodiments, the oral soluble film is orally administered to a subject with water or beverage.

In specific embodiments, the subject is a male.

In specific embodiments, the subject is a male that is at least 18 years old.

In specific embodiments, the oral soluble film is orally administered to treat erectile dysfunction, and the male subject achieves an erection in 25 minutes.

In specific embodiments, the oral soluble film is orally administered to treat erectile dysfunction (ED), and the male subject achieves an erection in 12-70 minutes.

In specific embodiments, the oral soluble film is administered sublingually, to treat erectile dysfunction (ED), the male subject achieves an erection in 15 minutes, and the erection lasting for 40 minutes.

In specific embodiments, up to two oral soluble films are administered per dose.

In specific embodiments, 1-2 oral soluble films are administered per dose.

In specific embodiments, two oral soluble films are administered per dose.

In specific embodiments, one and a half oral soluble films are administered per dose.

In specific embodiments, one oral soluble film is administered per dose.

In specific embodiments, a portion of an oral soluble film is administered per dose.

In specific embodiments, one-half of an oral soluble film is administered per dose.

In specific embodiments, the maximum recommended dosing frequency is twice per day.

In specific embodiments, the maximum recommended dosing frequency is once per day.

ENUMERATED EMBODIMENTS

Specific enumerated embodiments <1> to <47> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<Embodiment 1> an Oral Soluble Film that Includes:
(a) sildenafil citrate;
(b) binder that includes:
 (i) polyvinyl alcohol (PVA);
 (ii) polyvinyl alcohol (PVA)-polyethylene glycol (PEG) graft copolymer; and
 (iii) silicon dioxide;
(c) filler that includes microcrystalline cellulose (MCC);
(d) flavoring agent that includes peppermint flavoring;
(e) plasticizer that includes glycerin;
(f) sweetening agent that includes sucralose and acesulfame potassium (ACE-K);
(g) coloring agent that includes FD&C Blue 1;
(h) preservative that includes sodium benzoate; and
(i) solvent that includes water.

<Embodiment 2> The oral soluble film of embodiment <1>, configured as a unit dose having a mass of 200±20 mg.

<Embodiment 3> The oral soluble film of any one of embodiments <1> to <2>, having a thickness of 0.35±0.06 mm.

<Embodiment 4> The oral soluble film of any one of embodiments <1> to <3>, having a water content of 4±1.5 wt. %.

<Embodiment 5> The oral soluble film of any one of embodiments <1> to <4>, configured as a unit dose which dissolves within 60 seconds upon contact with an oral mucosal surface.

<Embodiment 6> The oral soluble film of any one of embodiments <1> to <5>, wherein the sildenafil citrate is present in 36±7 wt. % of the oral soluble film.

<Embodiment 7> The oral soluble film of any one of embodiments <1> to <6>, configured as a unit dose and wherein the sildenafil citrate is present in 70.24±7 mg.

<Embodiment 8> The oral soluble film of any one of embodiments <1> to <7>, wherein the binder is present in 30±6 wt. % of the oral soluble film.

<Embodiment 9> The oral soluble film of any one of embodiments <1> to <8>, configured as a unit dose and wherein the binder is present in 58.53±12 mg.

<Embodiment 10> The oral soluble film of any one of embodiments <1> to <9>, wherein the filler is present in 5.45±1 wt. % of the oral soluble film.

<Embodiment 11> The oral soluble film of any one of embodiments <1> to <10>, configured as a unit dose and wherein the filler is present in 10.63±2 mg.

<Embodiment 12> The oral soluble film of any one of embodiments <1> to <11>, wherein the flavoring agent is present in 6.44±1.25 wt. % of the oral soluble film.

<Embodiment 13> The oral soluble film of any one of embodiments <1> to <12>, configured as a unit dose and wherein the flavoring agent is present in 12.56±2.5 mg.

<Embodiment 14> The oral soluble film of any one of embodiments <1> to <13>, wherein the flavoring agent includes natural peppermint flavor.

<Embodiment 15> The oral soluble film of any one of embodiments <1> to <14>, wherein the plasticizer is present in 12±2.5 wt. % of the oral soluble film.

<Embodiment 16> The oral soluble film of any one of embodiments <1> to <15>, configured as a unit dose and wherein the plasticizer is present in 23.41±5 mg.

<Embodiment 17> The oral soluble film of any one of embodiments <1> to <16>, wherein the sweetening agent is present in 10±2 wt. % of the oral soluble film.

<Embodiment 18> The oral soluble film of any one of embodiments <1> to <17>, configured as a unit dose and wherein the sweetening agent is present in 19.5±4 mg.

<Embodiment 19> The oral soluble film of any one of embodiments <1> to <18>, wherein the coloring agent is present in 0.01±0.002 wt. % of the oral soluble film.

<Embodiment 20> The oral soluble film of any one of embodiments <1> to <19>, configured as a unit dose and wherein the coloring agent is present in 0.02±0.004 mg.

<Embodiment 21> The oral soluble film of any one of embodiments <1> to <20>, wherein the preservative is present in 0.10±0.02 wt. % of the oral soluble film.

<Embodiment 22> The oral soluble film of any one of embodiments <1> to <21>, configured as a unit dose and wherein the preservative is present in 0.20±0.04 mg.

<Embodiment 23> An oral soluble film that includes:
 (a) 36±7 wt. % sildenafil citrate;
 (b) 30±6 wt. % binder that includes:
  (i) polyvinyl alcohol (PVA);
  (ii) polyvinyl alcohol (PVA)-polyethylene glycol (PEG) graft copolymer; and
  (iii) silicon dioxide;
 (c) 5.45±1 wt. % filler that includes microcrystalline cellulose (MCC);
 (d) 6.44±1.25 wt. % flavoring agent that includes peppermint flavoring;
 (e) 12±2.5 wt. % plasticizer that includes glycerin;
 (f) 10±2 wt. % sweetening agent that includes sucralose and acesulfame potassium (ACE-K);
 (g) 0.01±0.002 wt. % coloring agent that includes FD&C Blue 1; and
 (h) 0.10±0.02 wt. % preservative that includes sodium benzoate.

<Embodiment 24> An oral soluble film that includes:
 (a) 70.24±7 mg sildenafil citrate;
 (b) 58.53±12 mg binder that includes:
  (i) polyvinyl alcohol (PVA);
  (ii) polyvinyl alcohol (PVA)-polyethylene glycol (PEG) graft copolymer; and
  (iii) silicon dioxide;
 (c) 10.63±2 mg filler that includes microcrystalline cellulose (MCC);
 (d) 12.56±2.5 mg flavoring agent that includes peppermint flavoring;
 (e) 23.41±5 mg plasticizer that includes glycerin;
 (f) 19.5±4 mg sweetening agent that includes sucralose and acesulfame potassium (ACE-K);
 (g) 0.02±0.004 mg coloring agent that includes FD&C Blue 1;
 (h) 0.20±0.04 mg preservative that includes sodium benzoate; and
 (i) 9.76±2.25 mg water;
wherein,
the oral soluble film is configured as a unit dose;
the oral soluble film has a mass of 205±20 mg;
the oral soluble film has a thickness of 0.35±0.06 mm; and
upon contact with an oral mucosal surface, the oral soluble film dissolves within 60 seconds.

<Embodiment 25> The oral soluble film of embodiment <24>, having a mass of 205±15 mg and dissolves within 45 seconds upon contact with an oral mucosal surface.

<Embodiment 26> An oral soluble film that includes:
 (a) 70.24±7 mg sildenafil citrate;
 (b) 58.53±12 mg binder that includes:
  (i) polyvinyl alcohol (PVA);
  (ii) polyvinyl alcohol (PVA)-polyethylene glycol (PEG) graft copolymer; and
  (iii) silicon dioxide;
 (c) 10.63±2 mg filler that includes microcrystalline cellulose (MCC);
 (d) 12.56±2.5 mg flavoring agent that includes peppermint flavoring;
 (e) 23.41±5 mg plasticizer that includes glycerin;
 (f) 19.5±4 mg sweetening agent that includes sucralose and acesulfame potassium (ACE-K);
 (g) 0.02±0.004 mg coloring agent that includes FD&C Blue 1;
 (h) 0.20±0.04 mg preservative that includes sodium benzoate; and
 (i) 9.76±2.25 mg water;
wherein,
the oral soluble film is configured as a unit dose.

<Embodiment 27> An oral soluble film that includes:
 (a) 70.24±7 mg sildenafil citrate;
 (b) 58.53±11.7 mg in the aggregate of:
  (i) polyvinyl alcohol (PVA);
  (ii) polyvinyl alcohol (PVA)-polyethylene glycol (PEG) graft copolymer; and
  (iii) silicon dioxide;
 (c) 10.63±2 mg microcrystalline cellulose (MCC);
 (d) 12.56±2.5 mg peppermint flavoring;
 (e) 23.41±5 mg glycerin;
 (f) 11.7±3 mg sucralose
 (g) 7.8±2.5 mg acesulfame potassium (ACE-K);
 (h) 0.02±0.004 mg FD&C Blue 1;
 (i) 0.20±0.04 mg sodium benzoate; and
 (j) 9.76±2.25 mg water;
wherein,
the oral soluble film is configured as a unit dose;
the oral soluble film has a mass of 204.9±20 mg;
the oral soluble film has a thickness of 0.35±0.06 mm; and
upon contact with an oral mucosal surface, the oral soluble film dissolves within 60 seconds.

<Embodiment 28> A method of treating erectile dysfunction (ED) in a male subject, the method includes orally administering the oral soluble film of any one of embodiments <1> to <27> to a male subject in need thereof.

<Embodiment 29> The method of embodiment <28>, wherein the oral administration includes at least one of enteral delivery of sildenafil, transmucosal delivery of sildenafil, sublingual delivery of sildenafil, and buccal delivery of sildenafil; wherein the sildenafil delivered is the free base or as the citrate salt.

<Embodiment 30> The method of any one of embodiments <28> to <29>, wherein the oral soluble film is administered to a male subject 1 hour before sexual activity.

<Embodiment 31> The method of any one of embodiments <28> to <29>, wherein the oral soluble film is administered to a male subject up to 20 minutes before sexual activity.

<Embodiment 32> The method of any one of embodiments <28> to <29>, wherein the oral soluble film is administered to a male subject 30 minutes to 4 hours before sexual activity.

<Embodiment 33> The method of any one of embodiments <28> to <32>, wherein the oral soluble film is placed on a mucosal surface within the oral cavity of the male subject.

<Embodiment 34> The method of any one of embodiments <28> to <33>, wherein the oral soluble film is placed on the top of the tongue of the male subject.

<Embodiment 35> The method of any one of embodiments <28> to <33>, wherein the oral soluble film is placed against the inside of the cheek of the male subject.

<Embodiment 36> The method of any one of embodiments <28> to <33>, wherein the oral soluble film is placed between the cheek and gums of the male subject.

<Embodiment 37> The method of any one of embodiments <28> to <36>, wherein the oral soluble film is orally administered to the male subject in the absence of water or beverage.

<Embodiment 38> The method of any one of embodiments <28> to <36>, wherein the oral soluble film is orally administered to the male subject with water or beverage.

<Embodiment 39> The method of any one of embodiments <28> to <38>, wherein the male subject achieves an erection within 25 minutes after the oral soluble film is orally administered.

<Embodiment 40> The method of any one of embodiments <28> to <38>, wherein the male subject achieves an erection in 12-70 minutes after the oral soluble film is orally administered.

<Embodiment 41> The method of any one of embodiments <28> to <38>, wherein the oral soluble film is administered sublingually, the male subject achieves an erection within 15 minutes, and the erection lasts for at least 30 minutes.

<Embodiment 42> The method of any one of embodiments <28> to <41>, wherein relative to VIAGRA® oral tablets having an equivalent amount of sildenafil citrate, administration of the oral soluble film results in a lower incidence, severity, and/or duration of adverse reactions, including at least one of headache, flushing, dyspepsia, abnormal vision, nasal congestion, back pain, myalgia, nausea, dizziness, and rash.

<Embodiment 43> The method of any one of embodiments <28> to <42>, wherein upon administration under fasted conditions with water, the oral soluble film exhibits a single-dose administration pharmacokinetic (PK) profile that includes:

| PK parameter | Amount of sildenafil citrate equivalent to 50 mg of sildenafil |
|---|---|
| $C_{MAX}$ (ng/mL) | 396.227 ± 105.035 |
| $AUC_{0 \to t}$ (hr * ng/mL) | 1,426.893 ± 520.565 |
| $AUC_{0 \to inf}$ (hr * ng/mL) | 1,524.433 ± 592.798 |
| $T_{MAX}$ (hr) | 1.088 ± 0.466 |
| $T_{1/2}$ (hr) | 3.783 ± 1.769 |
| $K_{EL}$ (1/hr) | 0.211 ± 0.068 |

<Embodiment 44> The method of any one of embodiments <28> to <42>, wherein upon administration under fasted conditions with no water, the oral soluble film exhibits a single-dose administration pharmacokinetic (PK) profile that includes:

| PK parameter | Amount of sildenafil citrate equivalent to 50 mg of sildenafil |
|---|---|
| $C_{MAX}$ (ng/mL) | 396.227 ± 105.035 |
| $AUC_{0 \to t}$ (hr * ng/mL) | 1,426.893 ± 520.565 |
| $AUC_{0 \to inf}$ (hr * ng/mL) | 1,524.433 ± 592.798 |
| $T_{MAX}$ (hr) | 1.088 ± 0.466 |
| $T_{1/2}$ (hr) | 3.783 ± 1.769 |
| $K_{EL}$ (1/hr) | 0.211 ± 0.068 |

<Embodiment 45> The method of any one of embodiments <28> to <44>, wherein up to two oral soluble films are administered per dose.

<Embodiment 46> The method of any one of embodiments <28> to <44>, having a maximum dosing frequency of once per day.

<Embodiment 47> The method of any one of embodiments <28> to <44>, wherein the male subject is at least 18 years old.

All publications, patents, and patent applications referred to herein are incorporated by reference in their entirety to the same extent as if each individual publication, patent, or patent application was specifically and individually indicated to be incorporated by reference in its entirety.

The following examples are set forth to further illustrate the presently disclosed subject matter (e.g., oral soluble films, methods of using the same, and methods of preparing the same). The below examples, however, should not be construed as limiting in any manner the present invention, as set forth in the claims.

EXAMPLES

Example 1: Oral Soluble Film Containing Sildenafil Citrate

| | FORMULATION 1.01 | | | | | |
|---|---|---|---|---|---|---|
| | | SLURRY | | ORAL SOLUBLE FILM Amount in | | |
| Substance | Quantity dispensed (g) | Amount in slurry (wt. %) | Amount in anhydrous film (wt. %) | Amount in anhydrous film (mg) | 5% hydrated film (wt. %) | Amount in 5% hydrated film (mg) |
| Sildenafil Citrate | 1678.6 | 16.8 | 36.00 | 70.24 | 34.29 | 70.24 |
| Kollicoat ® Protect | 1406.3 | 14.1 | 30.00 | 58.53 | 28.57 | 58.53 |
| Microcrystalline Cellulose - Avicel ® PH-101 | 252.1 | 2.5 | 5.45 | 10.63 | 5.19 | 10.63 |
| Peppermint Flavor | 299.9 | 3.0 | 6.44 | 12.56 | 6.13 | 12.56 |
| Glycerin, 99.7% pure | 558.5 | 5.6 | 12.00 | 23.41 | 11.43 | 23.41 |

FORMULATION 1.01

| Substance | SLURRY Quantity dispensed (g) | SLURRY Amount in slurry (wt. %) | Amount in anhydrous film (wt. %) | ORAL SOLUBLE FILM Amount in anhydrous film (mg) | Amount in 5% hydrated film (wt. %) | Amount in 5% hydrated film (mg) |
|---|---|---|---|---|---|---|
| Sucralose | 280.0 | 2.8 | 6.00 | 11.70 | 5.71 | 11.70 |
| Acesulfame Potassium (ACE-K) | 186.0 | 1.86 | 4.00 | 7.80 | 3.80 | 7.80 |
| FD&C Blue 1 | 0.5 | 0.005 | 0.01 | 0.02 | 0.01 | 0.02 |
| Sodium Benzoate | 5.0 | 0.05 | 0.10 | 0.20 | 0.10 | 0.20 |
| Water | 5328 | 53.3 | NA | NA | 5.00 | 9.76 |
| TOTAL | 10000.0 | 100 | 100 | 195.10 | 100 | 204.86 |

FORMULATION 1.02
Film weight (anhydrous): 209.6 mg; Film weight (10% hydrated): 233 mg

| Material | SLURRY Amount in Slurry (wt. %) | SLURRY Quantity dispensed (g) | ORAL SOLUBLE FILM Amount in 10% hydrated film (wt. %) | ORAL SOLUBLE FILM Amount in 10% hydrated film (mg) |
|---|---|---|---|---|
| Water | 47.83 | 1100 | 10.04 | 23.40 |
| Glycerin | 7.83 | 180 | 13.49 | 31.44 |
| Natural Orange | 4.17 | 96 | 7.20 | 16.77 |
| Vanilla cream | 1.04 | 24 | 1.80 | 4.19 |
| Sucralose | 2.61 | 60 | 4.50 | 10.48 |
| Acesulfame Potassium (ACE-K) | 1.30 | 30 | 2.25 | 5.24 |
| Microciystalline Cellulose | 1.57 | 36 | 2.70 | 6.29 |
| Kollicoat ® Protect | 12.13 | 279 | 20.92 | 48.73 |
| HPMC 2910, 15-18 mPa · s | 4.04 | 93 | 6.97 | 16.24 |
| Sildenafil Citrate | 17.48 | 402 | 30.14 | 70.22 |
| FD&C Red 40 | 0.00 | | | |
| FD&C Yellow 5 | 0.00 | | | |

FORMULATION 1.03
Film weight (anhydrous): 195.1 mg; Film weight (10% hydrated): 217 mg

| Material | SLURRY Amount in Slurry (wt. %) | SLURRY Quantity dispensed (g) | ORAL SOLUBLE FILM Amount in 10% hydrated film (wt. %) | ORAL SOLUBLE FILM Amount in 10% hydrated film (mg) |
|---|---|---|---|---|
| Water | 70.5882 | 240 | 10.09 | 21.90 |
| Glycerin | 1.3235 | 4.5 | 4.05 | 8.78 |
| Honey | 2.6471 | 9 | 8.09 | 17.56 |
| Polysorbate 80 | 1.1765 | 4 | 3.60 | 7.80 |
| Peppermint | 2.0588 | 7 | 6.29 | 13.66 |
| Sucralose | 1.4706 | 5 | 4.50 | 9.76 |
| ACE-K | 0.7353 | 2.5 | 2.25 | 4.88 |
| Pectin | 7.2794 | 24.75 | 22.25 | 48.29 |
| HPMC | 2.1294 | 7.24 | 6.51 | 14.13 |
| Sildenafil Citrate | 10.5882 | 36 | 32.37 | 70.24 |
| FD&C Blue 1 | 0.0029 | 0.01 | 0.01 | 0.02 |

FORMULATION 1.04
Film weight (anhydrous): 195.1 mg; Film weight (10% hydrated): 217 mg

| Material | SLURRY Amount in Slurry (wt. %) | SLURRY Quantity dispensed (g) | ORAL SOLUBLE FILM Amount in 10% hydrated film (wt. %) | ORAL SOLUBLE FILM Amount in 10% hydrated film (mg) |
|---|---|---|---|---|
| Water | 70.5882 | 240 | 10.09 | 21.9 |
| Glycerin | 3.9706 | 13.5 | 12.14 | 26.34 |
| Polysorbate 80 | 1.1765 | 4 | 3.60 | 7.80 |
| Peppermint | 2.0588 | 7 | 6.29 | 13.66 |
| Sucralose | 1.4706 | 5 | 4.50 | 9.76 |
| ACE-K | 0.7353 | 2.5 | 2.25 | 4.88 |
| Pectin | 7.2500 | 24.65 | 22.16 | 48.09 |
| HPMC | 2.1294 | 7.24 | 6.51 | 14.13 |
| Sildenafil Citrate | 10.5882 | 36 | 32.37 | 70.24 |
| FD&C Blue 1 | 0.0029 | 0.01 | 0.01 | 0.02 |
| Na Benzoate | 0.0294 | 0.1 | 0.09 | 0.20 |

FORMULATION 1.05
Film weight (anhydrous): 195.1 mg; Film weight (10% hydrated): 217 mg

| Material | SLURRY Amount in Slurry (wt. %) | SLURRY Quantity dispensed (g) | ORAL SOLUBLE FILM Amount in 10% hydrated film (wt. %) | ORAL SOLUBLE FILM Amount in 10% hydrated film (mg) |
|---|---|---|---|---|
| Water | 70.59 | 240 | 10.09 | 21.90 |
| Glycerin | 2.94 | 10 | 8.99 | 19.51 |
| Polysorbate 80 | 2.65 | 9 | 8.09 | 17.56 |
| Menthol | 0.46 | 1.55 | 1.39 | 3.02 |
| Peppermint | 0.13 | 0.45 | 0.40 | 0.88 |
| Vanilla Cream | 0.59 | 2 | 1.80 | 3.90 |
| Sucralose | 1.76 | 6 | 5.39 | 11.71 |
| ACE-K | 0.88 | 3 | 2.70 | 5.85 |
| Cekol ® 30 | 7.25 | 24.65 | 22.16 | 48.09 |
| HPMC | 2.13 | 7.24 | 6.51 | 14.13 |
| Sildenafil Citrate | 10.59 | 36 | 32.37 | 70.24 |
| FD&C Blue 1 | 0.00 | 0.01 | 0.01 | 0.02 |
| Na Benzoate | 0.03 | 0.1 | 0.09 | 0.20 |

FORMULATION 1.06
Film weight (anhydrous): 195.1 mg; Film weight (10% hydrated): 217 mg

| | SLURRY | | ORAL SOLUBLE FILM | |
|---|---|---|---|---|
| Material | Amount in Slurry (wt. %) | Quantity dispensed (g) | Amount in 10% hydrated film (wt. %) | Amount in 10% hydrated film (mg) |
| Water | 70.59 | 240 | 10.09 | 21.90 |
| Glycerin | 3.24 | 11 | 9.89 | 21.46 |
| Polysorbate 80 | 2.65 | 9 | 8.09 | 17.56 |
| Menthol | 0.43 | 1.45 | 1.30 | 2.83 |
| Spearmint | 0.32 | 1.1 | 0.99 | 2.15 |
| Peppermint | 0.13 | 0.45 | 0.40 | 0.88 |
| Sucralose | 1.76 | 6 | 5.39 | 11.71 |
| ACE-K | 0.88 | 3 | 2.70 | 5.85 |
| Cekol® 30 | 7.25 | 24.65 | 22.16 | 48.09 |
| HPMC | 2.13 | 7.24 | 6.51 | 14.13 |
| Sildenafil Citrate | 10.59 | 36 | 32.37 | 70.24 |
| FD&C Blue 1 | 0.003 | 0.01 | 0.01 | 0.02 |
| Na Benzoate | 0.03 | 0.1 | 0.09 | 0.20 |

FORMULATION 1.07
Film weight (anhydrous): 195.1 mg; Film weight (10% hydrated): 217 mg

| | SLURRY | | ORAL SOLUBLE FILM | |
|---|---|---|---|---|
| Material | Amount in Slurry (wt. %) | Quantity dispensed (g) | Amount in 0% hydrated film (wt. %) | Amount in 10% hydrated film (mg) |
| Water | 70.59 | 240 | 10.09 | 21.90 |
| Glycerin | 2.94 | 10 | 8.99 | 19.51 |
| Polysorbate 80 | 3.53 | 12 | 10.79 | 23.41 |
| Orange | 1.76 | 6 | 5.39 | 11.71 |
| Vanilla Cream | 0.76 | 2.59 | 2.33 | 5.05 |
| Sucralose | 2.06 | 7 | 6.29 | 13.66 |
| ACE-K | 0.88 | 3 | 2.70 | 5.85 |
| Cekol® 30 | 5.29 | 18 | 16.18 | 35.12 |
| HPMC | 1.56 | 5.3 | 4.77 | 10.34 |
| Sildenafil Citrate | 10.59 | 36 | 32.37 | 70.24 |
| FD&C Blue 1 | 0.003 | 0.01 | 0.01 | 0.02 |
| Na Benzoate | 0.03 | 0.1 | 0.09 | 0.20 |

FORMULATION 1.08
Film weight (anhydrous): 195.1 mg; Film weight (10% hydrated): 217 mg

| | SLURRY | | ORAL SOLUBLE FILM | |
|---|---|---|---|---|
| Material | Amount in Slurry (wt. %) | Quantity dispensed (g) | Amount in 10% hydrated film (wt. %) | Amount in 10% hydrated film (mg) |
| Water | 70.59 | 240 | 10.09 | 21.9 |
| Glycerin | 3.50 | 11.91 | 10.71 | 23.24 |
| Polysorbate 80 | 2.60 | 8.84 | 7.95 | 17.25 |
| NaOH | 0.18 | 0.6 | 0.54 | 1.17 |
| Peppermint | 1.72 | 5.84 | 5.25 | 11.39 |
| Sucralose | 2.06 | 7 | 6.29 | 13.66 |
| ACE-K | 1.18 | 4 | 3.60 | 7.80 |
| Cekol® 30 | 5.59 | 19 | 17.08 | 37.07 |
| HPMC | 1.97 | 6.7 | 6.02 | 13.07 |
| Sildenafil Citrate | 10.59 | 36 | 32.37 | 70.24 |
| FD&C Blue 1 | 0.003 | 0.01 | 0.01 | 0.02 |
| Na Benzoate | 0.03 | 0.1 | 0.09 | 0.20 |

FORMULATION 1.09
Film weight (anhydrous): 195.1 mg; Film weight (10% hydrated): 217 mg

| | SLURRY | | ORAL SOLUBLE FILM | |
|---|---|---|---|---|
| Material | Amount in Slurry (wt. %) | Quantity dispensed (g) | Amount in 0% hydrated film (wt. %) | Amount in 10% hydrated film (mg) |
| Water | 70.59 | 240 | 10.09 | 21.90 |
| Glycerin | 3.53 | 12 | 10.79 | 23.41 |
| NaOH | 0.18 | 0.6 | 0.54 | 1.17 |
| Mint | 1.72 | 5.84 | 5.25 | 11.39 |
| Sucralose | 1.76 | 6 | 5.39 | 11.71 |
| ACE-K | 1.18 | 4 | 3.60 | 7.80 |
| Kollicoat® protect | 8.82 | 30 | 26.97 | 58.53 |
| MCC | 1.60 | 5.45 | 4.90 | 10.63 |
| Sildenafil Citrate | 10.59 | 36 | 32.37 | 70.24 |
| FD&C Blue 1 | 0.003 | 0.01 | 0.01 | 0.02 |
| Na Benzoate | 0.03 | 0.1 | 0.09 | 0.20 |

FORMULATION 1.10
Film weight (anhydrous): 195.1 mg; Film weight (10% hydrated): 217 mg

| | SLURRY | ORAL SOLUBLE FILM | | |
|---|---|---|---|---|
| Material | Amount in Slurry (wt. %) | Amount in anhydrous film (wt. %) | Amount in 10% hydrated film (wt. %) | Amount in 10% hydrated film (mg) |
| Water | 54.79 | 0 | 10 | 21.68 |
| Sildenafil citrate | 16.27 | 36.00 | 32.40 | 70.24 |
| Kollicoat® protect | 13.56 | 30.00 | 27.00 | 58.53 |
| MCC | 2.46 | 5.45 | 4.91 | 10.64 |
| Spray mint flavoring | 2.64 | 6.44 | 5.80 | 12.57 |
| Glycerin | 5.42 | 12.00 | 10.80 | 23.41 |
| Sucralose | 2.71 | 6.00 | 5.40 | 11.71 |
| ACE-K | 1.81 | 4.00 | 3.60 | 7.80 |
| FD&C Blue 1 | 0.01 | 0.01 | 0.01 | 0.02 |
| Na Benzoate | 0.05 | 0.10 | 0.09 | 0.20 |

Example 2: Physical Properties and Performance Characteristics

Physical properties and performance characteristics for the oral soluble film of Formulation 1.01 (Example 1) include:
- The anhydrous film weight is 195.1±5 milligrams (mg).
- The 5 wt. % hydrated film weight is 204.9±5 mg.
- The breaking strength of the film is 8-12 Newtons (N).
- The elongation strength of the film is 2-4 millimeters (mm).
- The pH of the film is 4.0-4.5.
- The disintegration time of the film is ~1 minute or less.
- The Loss on Drying (LOD) of the film is 4±3 wt. %.
- The thickness of the film is 0.35±0.06 mm.
- The viscosity of the slurry at 20-30° Celsius is 6,000±1,000 centipoise (cP).
- Load of the active (sildenafil citrate) is 34.2% (in the 5% hydrated film) or 36% (in the anhydrous film).

| Physical or Performance Characteristic | Description of Measurement, Protocol (USP No.), and Equipment |
|---|---|
| Mass/weight of drug product | Gravimetric using calibrated scales |
| Thickness of drug product | Calipers |
| Moisture content of drug | USP <921> |

-continued

| Physical or Performance Characteristic | Description of Measurement, Protocol (USP No.), and Equipment |
|---|---|
| product | Gravimetric, mass loss on drying using a calibrated IR balance |
| Dissolution time of drug product in solution | USP <711> Drug release from the dosage form using USP apparatus 1 (basket) |
| Microbiology | USP <60>, USP <61>, and USP <62> |
| Disintegration time of drug product in mouth | USP <701> Done In-Vitro, approximately 30 sec. to break apart, full disintegration at about 1 min 40 sec. |
| Density of intermediate drug product | Gravimetric using weight/volume of a 22x38 mm film |
| Loss on drying (LOD) of drug product | USP <921> Same as above for moisture content |
| Breaking strength of drug product | Performed via Texture Analyzer, measures the forced required to break the film |
| Elongation strength of drug product | Performed via Texture Analyzer, measures the distanced traveled before breaking the film |
| pH of drug product | Performed via 3-point calibrated pH meter |
| Viscosity of the slurry | Tested using a viscometer with rotor 7 speed 100 rpm |
| Drug Assay | USP <621> HPLC used to measure the amount of API in the slurry (±5%) and the finished good, OSF (±10%) |
| Drug content uniformity of drug product | USP <905> Measure the total drug content of 10 individual films which must pass with an Acceptance Value (AV) of less than 15 |
| Particle-size distribution of sildenafil citrate (drug substance) | D(90) <60 μm, obtained from the API supplier, CoA |
| Impurities and Related Substances | USP <1086> Chromatography method to detect, characterize and quantify potential impurities and related substances from the drug product. |

Example 3: Method of Manufacturing Oral Dissolvable Film

The oral soluble film of Formulation 1.01 (Example 1) was manufactured as described below.

3.1 Dispensing

Dispense the following raw materials in its given amounts in separate containers.

| Ingredient | % w/w | Theoretical (g)/batch |
|---|---|---|
| Water | 53.30% | 5,327.6 |
| Sildenafil Citrate | 16.79% | 1,678.6 |
| Kollicoat ® Protect | 14.08% | 1,406.3 |
| Avicel PH-101 Microcrystalline Cellulose | 2.53% | 252.1 |
| Natural Peppermint Flavor | 3.00% | 299.9 |
| Glycerin 99.7% | 5.59% | 558.5 |
| Sucralose | 2.80% | 280.0 |
| Ace-K | 1.86% | 186.0 |
| FD&C Blue #1 Powder | 0.005% | 0.5 |
| Sodium Benzoate Powder | 0.05% | 5.0 |
| Total | 100.00% | 10,000.00 |

3.2 Blending, Method A
  3.2.1 Add water into a mixing container. To this container, add the glycerin and mix for approximately 10 minutes.
  3.2.2 Weigh and add the following powders together, in the following order:
    1. Kollicoat® Protect
    2. Sildenafil Citrate
    3. Sucralose
    4. Ace-K
    5. Sodium Benzoate
    6. Microcrystalline Cellulose
    7. Peppermint
    8. FD&C Blue
3.3 Blending, Method B
  3.3.1 Add water into a mixing container and begin mixing.
  3.3.2 Weigh and add the following excipients and add into water container, in the following order:
    1. Sildenafil Citrate
    2. Glycerin
    3. Sucralose
    4. Ace-K
    5. Sodium Benzoate
    6. FD&C Blue #1
    7. Microcrystalline Cellulose
    8. Kollicoat® Protect
    9. Peppermint
  3.3.3 Check the temperature, density, and viscosity of the blend against target. Continue mixing and add water if needed.
  3.3.4 Once blend is finished, take sample for % solids by IR and LOD analysis.
3.4 Curing
Cure the slurry on the oven.
  3.4.1 Set the oven with the following parameters.

| Parameter |
|---|
| Pin Gauge |
| Oven Temperature |
| Line Speed |
| Knife web size |

3.4.2 Begin curing process once oven achieved desired temperature.
  3.4.3 Start rewinder at desired line speed.
  3.4.4 Slowly pour slurry into the extruder.
  3.4.5 Record measurements as needed.
  3.4.6 Stored the results in a temperature and humidity-controlled environment in appropriated bags.
3.5 Converting
  3.5.1 Load a bulk roll onto the machine and input the relevant setting for speed, shape, and weight.
  3.5.2 Load the primary packaging material and input the relevant setting for example strength of seal.
  3.5.3 Preform in process checks as necessary to ensure the finished product meet desired specifications.

Example 4: Bioavailable Study

A bioavailability study (under fasting conditions, with water) in healthy adult human male subjects (n=18) was conducted, to compare the sildenafil citrate oral soluble film (EQ 50 mg base) of Formulation 1.01 (Example 1), with that of Viagra® oral tablets (EQ 50 mg base), post single oral administration. Each subject was given water (40 ml) with the sample.

Primary parameters ($C_{max}$, $AUC_{0 \to t}$, and $AUC_{0 \to inf}$) as well as secondary parameters ($T_{max}$, $T_{1/2}$, and $K_{el}$) were measured.

The table below provides the results of the study.

| Bioavailable Study: Pharmacokinetic (PK) Parameters | | | |
|---|---|---|---|
| PK Parameter | Sample (Reference or Test) | Mean | Std. Dev. |
| $C_{MAX}$ (ng/mL) | Viagra ® oral tablets (EQ 50 mg base) | 405.717 | 136.894 |
| | Sildenafil citrate oral soluble film (EQ 50 mg base) | 396.227 | 105.035 |
| $AUC_{0 \to t}$ (hr * ng/mL) | Viagra ® oral tablets (EQ 50 mg base) | 1,237.489 | 339.650 |
| | Sildenafil citrate oral soluble film (EQ 50 mg base) | 1,426.893 | 520.565 |
| $AUC_{0 \to inf}$ (hr * ng/mL) | Viagra ® oral tablets (EQ 50 mg base) | 1,330.010 | 364.587 |
| | Sildenafil citrate oral soluble film (EQ 50 mg base) | 1,524.433 | 592.798 |
| $T_{MAX}$ (hr) | Viagra ® oral tablets (EQ 50 mg base) | 1.083 | 0.636 |
| | Sildenafil citrate oral soluble film (EQ 50 mg base) | 1.088 | 0.466 |
| $T_{1/2}$ (hr) | Viagra ® oral tablets (EQ 50 mg base) | 4.577 | 2.771 |
| | Sildenafil citrate oral soluble film (EQ 50 mg base) | 3.783 | 1.769 |
| $K_{EL}$ (1/hr) | Viagra ® oral tablets (EQ 50 mg base) | 0.188 | 0.074 |
| | Sildenafil citrate oral soluble film (EQ 50 mg base) | 0.211 | 0.068 |

The invention claimed is:

1. An oral soluble film, comprising:
   (a) 36±7 wt. % sildenafil citrate;
   (b) 30±6 wt. % binder comprising:
      (i) polyvinyl alcohol (PVA);
      (ii) polyvinyl alcohol (PVA)-polyethylene glycol (PEG) graft copolymer; and
      (iii) silicon dioxide;
   (c) 5.45±1 wt. % filler comprising microcrystalline cellulose (MCC);
   (d) 6.44±1.25 wt. % flavoring agent comprising peppermint flavoring;
   (e) 12±2.5 wt. % plasticizer comprising glycerin;
   (f) 10±2 wt. % sweetening agent comprising sucralose and acesulfame potassium (ACE-K);
   (g) 0.01±0.002 wt. % coloring agent comprising FD&C Blue 1;
   (h) 0.10±0.02 wt. % preservative comprising sodium benzoate; and
   (i) solvent comprising water.

2. An oral soluble film comprising:
   (a) 70.24±7 mg sildenafil citrate;
   (b) 58.53±12 mg binder comprising:
      (i) polyvinyl alcohol (PVA);
      (ii) polyvinyl alcohol (PVA)-polyethylene glycol (PEG) graft copolymer; and
      (iii) silicon dioxide;
   (c) 10.63±2 mg filler comprising microcrystalline cellulose (MCC);
   (d) 12.56±2.5 mg flavoring agent comprising peppermint flavoring;
   (e) 23.41±5 mg plasticizer comprising glycerin;
   (f) 19.5±4 mg sweetening agent comprising sucralose and acesulfame potassium (ACE-K);
   (g) 0.02±0.004 mg coloring agent comprising FD&C Blue 1;
   (h) 0.20±0.04 mg preservative comprising sodium benzoate; and
   (i) 9.76±2.25 mg water;

wherein,
   the oral soluble film is configured as a unit dose;
   the oral soluble film has a mass of 205±20 mg;
   the oral soluble film has a thickness of 0.35±0.06 mm; and
   upon contact with an oral mucosal surface, the oral soluble film dissolves within 60 seconds.

3. The oral soluble film of claim 2, having a mass of 205±15 mg and which dissolves within 45 seconds upon contact with an oral mucosal surface.

4. A method of treating erectile dysfunction (ED) in a male subject, the method comprising orally administering the oral soluble film of claim 2 to a male subject in need thereof.

5. The method of claim 4, wherein the oral administration comprises at least one of enteral delivery of sildenafil, transmucosal delivery of sildenafil, sublingual delivery of sildenafil, and buccal delivery of sildenafil; wherein the sildenafil is delivered as the free base or as the citrate salt.

6. The method of claim 4, wherein the oral soluble film is administered to a male subject 30 minutes to 4 hours before sexual activity.

7. The method of claim 4, wherein the oral soluble film is placed on the top of the tongue of the male subject.

8. The method of claim 4, wherein the oral soluble film is orally administered to the male subject in the absence of water or beverage.

9. The method of claim 4, wherein upon administration of sildenafil citrate equivalent to 50 mg of sildenafil, under fasted conditions with water, the oral soluble film exhibits a single-dose administration pharmacokinetic (PK) profile that comprises:
   $C_{MAX}$ (ng/mL) of 396.227±105.035;
   $AUC_{0 \to t}$ (hr*ng/mL) of 1,426.893±520.565;
   $AUC_{0 \to inf}$ (hr*ng/mL) of 1,524.433±592.798;
   $T_{MAX}$ (hr) of 1.088±0.466;
   $T_{1/2}$ (hr) of 3.783±1.769; and
   $K_{EL}$ (1/hr) of 0.211±0.068.

10. The method of claim 4, having a maximum dosing frequency of once per day.

11. The method of claim 4, wherein the male subject is at least 18 years old.

12. The oral soluble film of claim 1, configured as a unit dose, wherein the oral soluble film:
   (a) has a mass of 200±20 mg;
   (b) has a thickness of 0.35±0.06 mm;
   (c) has a water content of 4±1.5 wt. %; and
   (d) dissolves within 60 seconds upon contact with an oral mucosal surface.

13. The oral soluble film of claim 1, configured as a unit dose, having a mass of 205±15 mg, and which dissolves within 45 seconds upon contact with an oral mucosal surface.

14. A method of treating erectile dysfunction (ED) in a male subject, the method comprising orally administering the oral soluble film of claim 1, configured as a unit dose, to a male subject in need thereof.

15. The method of claim 14, wherein the oral administration comprises at least one of enteral delivery of sildenafil, transmucosal delivery of sildenafil, sublingual delivery of sildenafil, and buccal delivery of sildenafil; wherein the sildenafil is delivered as the free base or as the citrate salt.

16. The method of claim 14, wherein the oral soluble film is administered to a male subject 30 minutes to 4 hours before sexual activity.

17. The method of claim 14, wherein the oral soluble film is placed on the top of the tongue of the male subject.

18. The method of claim 14, wherein the oral soluble film is orally administered to the male subject in the absence of water or beverage.

19. The method of claim 14, wherein upon administration of sildenafil citrate equivalent to 50 mg of sildenafil, under fasted conditions with water, the oral soluble film exhibits a single-dose administration pharmacokinetic (PK) profile that comprises:

$C_{MAX}$ (ng/mL) of 396.227±105.035;
$AUC_{0 \to t}$ (hr*ng/mL) of 1,426.893±520.565;
$AUC_{0 \to inf}$ (hr*ng/mL) of 1,524.433±592.798;
$T_{MAX}$ (hr) of 1.088±0.466;
$T_{1/2}$ (hr) of 3.783±1.769; and
$K_{EL}$ (1/hr) of 0.211±0.068.

20. The method of claim 14, having a maximum dosing frequency of once per day.

21. The method of claim 14, wherein the male subject is at least 18 years old.

22. The oral soluble film of claim 1, configured as a bulk roll.

23. The oral soluble film of claim 1, having a water content of 4±1.5 wt. %.

24. The oral soluble film of claim 1, which is manufactured from non-micronized sildenafil citrate having the following particle size distribution (PSD):

the percentage of particles smaller than 2 μm is 10%;
the percentage of particles smaller than 5 μm is 50%; and
the percentage of particles smaller than 35 μm is 90%.

25. The oral soluble film of claim 2, wherein the variation of sildenafil citrate between two equally sized unit dosages is less than 5 wt. %.

\* \* \* \* \*